(12) United States Patent
Bar-Or et al.

(10) Patent No.: US 11,026,940 B2
(45) Date of Patent: *Jun. 8, 2021

(54) COMPOSITIONS FOR THE MOBILIZATION, HOMING, EXPANSION AND DIFFERENTIATION OF STEM CELLS AND METHODS OF USING THE SAME

(71) Applicant: Ampio Pharmaceuticals, Inc., Englewood, CO (US)

(72) Inventors: David Bar-Or, Englewood, CO (US); Greg Thomas, Highlands Ranch, CO (US)

(73) Assignee: Ampio Pharmaceuticals, Inc., Englewood, CO (US)

( * ) Notice: Subject to any disclaimer, the term of this patent is extended or adjusted under 35 U.S.C. 154(b) by 17 days.

This patent is subject to a terminal disclaimer.

(21) Appl. No.: 15/723,687

(22) Filed: Oct. 3, 2017

(65) Prior Publication Data

US 2018/0153880 A1  Jun. 7, 2018

Related U.S. Application Data

(63) Continuation of application No. 14/216,430, filed on Mar. 17, 2014, now Pat. No. 9,808,454.

(60) Provisional application No. 61/939,625, filed on Feb. 13, 2014, provisional application No. 61/923,314, filed on Jan. 3, 2014, provisional application No. 61/897,449, filed on Oct. 30, 2013, provisional application No. 61/832,713, filed on Jun. 7, 2013, provisional application No. 61/791,623, filed on Mar. 15, 2013.

(51) Int. Cl.
| | |
|---|---|
| *A61K 31/495* | (2006.01) |
| *A61K 31/405* | (2006.01) |
| *A61K 31/20* | (2006.01) |
| *A61K 35/28* | (2015.01) |
| *C12N 5/0775* | (2010.01) |
| *A61K 35/32* | (2015.01) |

(52) U.S. Cl.
CPC ............ *A61K 31/495* (2013.01); *A61K 31/20* (2013.01); *A61K 31/405* (2013.01); *A61K 35/28* (2013.01); *C12N 5/0663* (2013.01); *A61K 35/32* (2013.01); *C12N 2501/999* (2013.01)

(58) Field of Classification Search
CPC .... A61K 31/495; A61K 31/405; A61K 31/20; A61K 35/28; A61K 35/32; C12N 5/0663; C12N 2501/999; A61P 43/00; A61P 29/00; A61P 25/00; A61P 19/04; A61P 19/02; A61P 19/00
See application file for complete search history.

(56) References Cited

U.S. PATENT DOCUMENTS

| | | |
|---|---|---|
| 3,763,091 A | 10/1973 | Crescenzi et al. |
| 3,772,265 A | 11/1973 | Isowa et al. |
| 3,928,330 A | 12/1975 | Ramey et al. |
| 3,941,790 A | 3/1976 | Creighton |
| 3,976,773 A | 8/1976 | Curran |
| 4,006,261 A | 2/1977 | Pickenhagen et al. |
| 4,088,649 A | 5/1978 | Smith et al. |
| 4,205,057 A | 5/1980 | Whitaker |
| 4,289,759 A | 9/1981 | Heavner et al. |
| 4,312,987 A | 1/1982 | Beck |
| 4,331,595 A | 5/1982 | Heavner et al. |
| 4,661,500 A | 4/1987 | Rozencwaig |
| 4,694,061 A | 9/1987 | Pfeifer |
| 4,694,081 A | 9/1987 | Miller et al. |
| 4,771,056 A | 9/1988 | Rozencwaig |
| 4,806,538 A | 2/1989 | Shimazaki et al. |
| 4,886,796 A | 12/1989 | Eichner et al. |
| 4,940,709 A | 7/1990 | Shimazaki et al. |
| 4,992,552 A | 2/1991 | Hubbs et al. |
| 5,047,401 A | 9/1991 | Lipsky et al. |
| 5,144,073 A | 9/1992 | Hubbs |
| 5,238,938 A | 8/1993 | Tone et al. |
| 5,352,461 A | 10/1994 | Feldstein et al. |
| 5,358,938 A | 10/1994 | Cai et al. |
| 5,358,953 A | 10/1994 | Alker et al. |
| 5,418,218 A | 5/1995 | Wilber |
| 5,434,151 A | 7/1995 | Cai et al. |
| 5,463,083 A | 10/1995 | Biftu et al. |
| 5,503,852 A | 4/1996 | Steiner et al. |
| 5,512,544 A | 4/1996 | Wallach et al. |
| 5,538,993 A | 7/1996 | Mechoulam et al. |
| 5,543,402 A | 8/1996 | Bosies et al. |
| 5,543,503 A | 8/1996 | Chuntharapai et al. |
| 5,545,404 A | 8/1996 | Page |
| 5,550,132 A | 8/1996 | Benson et al. |
| 5,561,115 A | 10/1996 | Tenold |
| 5,578,323 A | 11/1996 | Milstein et al. |
| 5,589,501 A | 12/1996 | Carrera et al. |
| 5,648,486 A | 7/1997 | Cai et al. |
| 5,665,714 A | 9/1997 | Paltauf et al. |
| 5,693,338 A | 12/1997 | Milstein |
| 5,700,804 A | 12/1997 | Collins et al. |

(Continued)

FOREIGN PATENT DOCUMENTS

| | | |
|---|---|---|
| CN | 1120439 | 4/1996 |
| CN | 101914490 | 12/2010 |

(Continued)

OTHER PUBLICATIONS

Chase et al. (2010, Stem Cell Res. Therapy, vol. 1(8), pp. 1-11) (Year: 2010).*

(Continued)

*Primary Examiner* — Thaian N. Ton
(74) *Attorney, Agent, or Firm* — Sheridan Ross P.C.

(57) ABSTRACT

The invention provides compositions that increase the mobilization, homing, expansion, and/or differentiation of stem cells and methods of using the same for the treatment of mammals.

6 Claims, 13 Drawing Sheets

(56) References Cited

U.S. PATENT DOCUMENTS

| | | |
|---|---|---|
| 5,703,093 A | 12/1997 | Cai et al. |
| 5,741,809 A | 4/1998 | Biftu et al. |
| 5,750,530 A | 5/1998 | Bryans et al. |
| 5,750,565 A | 5/1998 | Cai et al. |
| 5,776,892 A | 7/1998 | Counts et al. |
| 5,780,503 A | 7/1998 | Biftu et al. |
| 5,792,776 A | 8/1998 | Biftu et al. |
| 5,811,241 A | 9/1998 | Goodfellow et al. |
| 5,817,751 A | 10/1998 | Szardenings et al. |
| 5,834,032 A | 11/1998 | Song |
| 5,843,950 A | 12/1998 | Tasaka et al. |
| 5,856,323 A | 1/1999 | Cai et al. |
| 5,877,174 A | 3/1999 | Ono et al. |
| 5,883,227 A | 3/1999 | Kline et al. |
| 5,886,152 A | 3/1999 | Nakatani et al. |
| 5,902,812 A | 5/1999 | Brocchini et al. |
| 5,919,785 A | 7/1999 | Dinsmore et al. |
| 5,932,112 A | 8/1999 | Browning, Jr. |
| 5,932,579 A | 8/1999 | Campbell et al. |
| 5,976,569 A | 11/1999 | Milstein |
| 5,985,581 A | 11/1999 | Nixon et al. |
| 5,990,112 A | 11/1999 | Campbell et al. |
| 6,034,057 A | 3/2000 | Dutta |
| 6,034,221 A | 3/2000 | Berezenko et al. |
| 6,060,452 A | 5/2000 | Green et al. |
| 6,090,780 A | 7/2000 | Prasad |
| 6,096,737 A | 8/2000 | Loder |
| 6,099,856 A | 8/2000 | Milstein et al. |
| 6,107,050 A | 8/2000 | Alkon et al. |
| 6,180,616 B1 | 1/2001 | Fukunaga |
| 6,222,029 B1 | 4/2001 | Edwards et al. |
| 6,248,363 B1 | 6/2001 | Patel et al. |
| 6,262,119 B1 | 7/2001 | Ferrante et al. |
| 6,265,535 B1 | 7/2001 | Greene et al. |
| 6,331,318 B1 | 12/2001 | Milstein et al. |
| 6,358,957 B1 | 3/2002 | Fukumoto et al. |
| 6,395,774 B1 | 5/2002 | Milstein |
| 6,441,172 B1 | 8/2002 | Nefzi et al. |
| 6,461,875 B1 | 10/2002 | Bar-Or et al. |
| 6,475,743 B1 | 11/2002 | Bar-Or et al. |
| 6,492,179 B1 | 12/2002 | Bar-Or et al. |
| 6,531,505 B2 | 3/2003 | Xu et al. |
| 6,541,224 B2 | 4/2003 | Yu et al. |
| 6,555,543 B2 | 4/2003 | Bar-Or et al. |
| 6,635,649 B2 | 10/2003 | Teng et al. |
| 6,677,473 B1 | 1/2004 | Madison et al. |
| 6,689,765 B2 | 2/2004 | Baroudy et al. |
| 6,815,214 B2 | 11/2004 | Boyce et al. |
| 6,930,112 B2 | 8/2005 | Weaver et al. |
| 6,967,202 B2 | 11/2005 | Rao et al. |
| 7,026,322 B2 | 4/2006 | Hayashi et al. |
| 7,175,844 B2 | 2/2007 | King |
| 7,276,534 B2 | 10/2007 | Milstein |
| 7,288,545 B2 | 10/2007 | Teng et al. |
| 7,332,153 B2 | 2/2008 | Bhatia et al. |
| 7,378,403 B2 | 5/2008 | Kozikowski et al. |
| 7,575,929 B2 | 8/2009 | Bar-Or et al. |
| 7,732,403 B2 | 6/2010 | Bar-Or et al. |
| 7,919,497 B2 | 4/2011 | Palladino et al. |
| 8,030,488 B2 | 10/2011 | Sviridov et al. |
| 8,067,425 B2 | 11/2011 | Brimble et al. |
| 8,183,209 B2 * | 5/2012 | Bar-Or ................ A61K 31/495 514/21.1 |
| 8,198,407 B1 | 6/2012 | Burton et al. |
| 8,217,047 B2 | 7/2012 | Bar-Or |
| 8,268,830 B2 | 9/2012 | Bar-Or et al. |
| 8,314,106 B2 | 11/2012 | Kraft |
| 8,324,167 B2 | 12/2012 | Bar-Or et al. |
| 8,383,124 B2 | 2/2013 | Zheng |
| 8,440,696 B2 | 5/2013 | Bar-Or et al. |
| 8,455,517 B2 | 6/2013 | Bar-Or et al. |
| 8,507,496 B2 | 8/2013 | Bar-Or |
| 8,513,196 B2 | 8/2013 | Bar-Or et al. |
| 8,551,953 B2 | 10/2013 | Bar-Or et al. |
| 8,841,307 B2 | 9/2014 | Bar-Or et al. |
| 8,871,772 B2 | 10/2014 | Bar-Or |
| 8,916,568 B2 | 12/2014 | Bar-Or et al. |
| 8,962,568 B2 | 2/2015 | Bar-Or et al. |
| 8,969,308 B2 | 3/2015 | Bar-Or et al. |
| 8,980,834 B2 | 3/2015 | Bar-Or et al. |
| 9,034,878 B2 | 5/2015 | Bar-Or |
| 9,060,968 B2 | 6/2015 | Bar-Or et al. |
| 9,522,893 B2 | 12/2016 | Bar-Or |
| 9,561,226 B2 | 2/2017 | Bar-Or et al. |
| 9,623,072 B2 | 4/2017 | Bar-Or et al. |
| 9,808,454 B2 | 11/2017 | Bar-Or et al. |
| 2003/0119750 A1 | 6/2003 | Demuth et al. |
| 2003/0153575 A1 | 8/2003 | Orme et al. |
| 2003/0157030 A1 | 8/2003 | Davis et al. |
| 2003/0187226 A1 | 10/2003 | Goddey et al. |
| 2003/0203915 A1 | 10/2003 | Fang et al. |
| 2004/0024180 A1 | 2/2004 | Drauz et al. |
| 2004/0038865 A1 | 2/2004 | Gelber et al. |
| 2004/0063654 A1 | 4/2004 | Davis et al. |
| 2005/0096323 A1 | 5/2005 | Cheng et al. |
| 2005/0249681 A1 | 11/2005 | Heidenfelder et al. |
| 2007/0060508 A1 | 3/2007 | Haberl et al. |
| 2007/0208087 A1 | 9/2007 | Sanders et al. |
| 2008/0009507 A1 | 1/2008 | Cosford et al. |
| 2008/0017576 A1 | 1/2008 | Belfort et al. |
| 2008/0260838 A1 | 10/2008 | Hokenson et al. |
| 2009/0038416 A1 | 2/2009 | Bonner |
| 2010/0042206 A1 | 2/2010 | Yadav et al. |
| 2010/0120056 A1 | 5/2010 | Bar-Or et al. |
| 2010/0144611 A1 | 6/2010 | Bar-Or et al. |
| 2010/0190696 A1 | 7/2010 | Bar-Or et al. |
| 2012/0058934 A1 | 3/2012 | Bar-Or |
| 2012/0094918 A1 | 4/2012 | Bar-Or et al. |
| 2012/0220530 A1 | 8/2012 | Plumridge et al. |
| 2013/0079284 A1 | 3/2013 | Bar-Or et al. |
| 2014/0294738 A1 | 10/2014 | Bar-Or |
| 2014/0302114 A1 | 10/2014 | Bar-Or |
| 2015/0366932 A1 | 12/2015 | Bar-Or |
| 2016/0015705 A1 | 1/2016 | Bar-Or et al. |
| 2016/0045493 A1 | 2/2016 | Bar-Or |
| 2016/0367644 A1 | 12/2016 | Bar-Or et al. |

FOREIGN PATENT DOCUMENTS

| | | |
|---|---|---|
| CS | 254868 | 6/1987 |
| CZ | 2827.94 | 4/1996 |
| CZ | 280726 | 4/1996 |
| CZ | 2000-2680 | 7/2000 |
| CZ | 2000-2681 | 7/2000 |
| DE | 19937721 | 2/2001 |
| EP | 0043219 | 1/1982 |
| EP | 0214557 | 3/1987 |
| EP | 0216746 | 4/1987 |
| EP | 0220958 | 5/1987 |
| EP | 0493812 | 7/1992 |
| EP | 0557388 | 9/1993 |
| EP | 0610943 | 8/1994 |
| EP | 0655060 | 5/1995 |
| EP | 0835660 | 4/1998 |
| EP | 0939124 | 9/1999 |
| EP | 1445323 | 8/2004 |
| FR | 2717484 | 9/1995 |
| GB | 2263109 | 7/1993 |
| GB | 2372740 | 9/2002 |
| JP | S52-25019 | 2/1977 |
| JP | S57-32272 | 2/1982 |
| JP | S59-73574 | 4/1984 |
| JP | S61-112060 | 5/1986 |
| JP | S62-036331 | 2/1987 |
| JP | S63-290868 | 11/1988 |
| JP | H01-013075 | 1/1989 |
| JP | 3176478 | 7/1991 |
| JP | H05-163148 | 6/1993 |
| JP | H07-247474 | 9/1995 |
| JP | H08-277203 | 10/1996 |
| JP | H10-226615 | 8/1998 |
| JP | H10-245315 | 9/1998 |
| JP | H11-504509 | 4/1999 |
| JP | 2000-327575 | 11/2000 |

(56) References Cited

FOREIGN PATENT DOCUMENTS

| | | |
|---|---|---|
| JP | 2001-055340 | 2/2001 |
| JP | 2008-505084 | 2/2008 |
| JP | 2009-508658 | 3/2009 |
| JP | 2010-508971 | 3/2010 |
| JP | 2011-507609 | 3/2011 |
| NZ | 218088 | 1/1989 |
| NZ | 335544 | 8/2001 |
| RU | 2112242 | 5/1998 |
| RU | 2125728 | 1/1999 |
| RU | 2128840 | 4/1999 |
| WO | WO 91/14378 | 10/1991 |
| WO | WO 93/08815 | 5/1993 |
| WO | WO 94/04512 | 3/1994 |
| WO | WO 94/04513 | 3/1994 |
| WO | WO 94/04537 | 3/1994 |
| WO | WO 94/20063 | 9/1994 |
| WO | WO 95/03054 | 2/1995 |
| WO | WO 95/18610 | 7/1995 |
| WO | WO 96/00212 | 1/1996 |
| WO | WO 96/00391 | 1/1996 |
| WO | WO 96/10396 | 4/1996 |
| WO | WO 96/14317 | 5/1996 |
| WO | WO 96/32478 | 10/1996 |
| WO | WO 97/12625 | 4/1997 |
| WO | WO 97/36888 | 10/1997 |
| WO | WO 97/38011 | 10/1997 |
| WO | WO 97/48685 | 12/1997 |
| WO | WO 98/09968 | 3/1998 |
| WO | WO 98/40748 | 9/1998 |
| WO | WO 99/40931 | 8/1999 |
| WO | WO 99/49865 | 10/1999 |
| WO | WO 99/51256 | 10/1999 |
| WO | WO 99/51720 | 10/1999 |
| WO | WO 00/20454 | 4/2000 |
| WO | WO 00/20840 | 4/2000 |
| WO | WO 00/22439 | 4/2000 |
| WO | WO 00/43000 | 7/2000 |
| WO | WO 00/057187 | 9/2000 |
| WO | WO 01/34586 | 5/2001 |
| WO | WO 01/64241 | 9/2001 |
| WO | WO 01/91713 | 12/2001 |
| WO | WO 02/011676 | 2/2002 |
| WO | WO 02/012201 | 2/2002 |
| WO | WO 02/059604 | 8/2002 |
| WO | WO 02/062797 | 8/2002 |
| WO | WO 02/083667 | 10/2002 |
| WO | WO 02/089738 | 11/2002 |
| WO | WO 03/032809 | 4/2003 |
| WO | WO 03/045395 | 6/2003 |
| WO | WO 2004/005292 | 1/2004 |
| WO | WO 2004/034060 | 4/2004 |
| WO | WO 2004/048345 | 6/2004 |
| WO | WO 2004/054498 | 7/2004 |
| WO | WO 2005/011699 | 2/2005 |
| WO | WO 2006/023943 | 3/2006 |
| WO | WO 2007/098500 | 8/2007 |
| WO | WO 2007/121411 | 10/2007 |
| WO | WO 2007/149730 | 12/2007 |
| WO | WO 2008/008357 | 1/2008 |
| WO | WO 2009/009793 | 1/2009 |
| WO | WO 2009/032651 | 3/2009 |
| WO | WO 2009/042193 | 4/2009 |
| WO | WO 2010/102148 | 9/2010 |
| WO | WO 2012/033789 | 3/2012 |
| WO | WO 2012/045094 | 4/2012 |
| WO | WO 2012/174472 | 12/2012 |

OTHER PUBLICATIONS

Ampio Pharmaceuticals, Inc, Sep. 25, 2012, pp. 1-14 (Year: 2012).*
Tirumalai et al., 2003, Mol. Cell. Proteomics, vol. 2(10), pp. 1096-1103 (Year: 2003).*
Francis et al. (2010, Cytotechnology, vol. 62, pp. 1-16) (Year: 2010).*
Official Action for Australian Patent Application No. 2014232728 dated Feb. 23, 2017, 5 pages.
Official Action (with English translation) for Israeli Patent Application No. 240473 dated May 13, 2018, 12 pages.
Official Action (with English translation) for Japanese Patent Application No. 2016-503416 dated Jun. 19, 2018, 9 pages.
"CENTRICON Centrifugal Filter Devices User Guide," Millipore Corp., Mar. 2005, 23 pages.
Cytokines and Autoimmune Diseases, edited by Kuchroo, et al., 2002, Humana Press Inc., Totowa, NJ, pp. 3-23, 389-406.
Cytokines and Autoimmune Diseases, edited by Kuchroo, et al., 2002, Humana Press Inc., Totowa, NJ, pp. 5, 11, and 391.
Database WPI Section Ch, Week 199844 Derwent Publications Ltd., London, GB; Class B03, AN 1998-515050 XP002369751 & JP 10 226615 A (Pola Chem Ind Inc) Aug. 25, 1998 (Aug. 25, 1998).
"Diabetic Retinopathy—What you should know," National Institutes of Health, 2003, NIH Publication No. 06-2171, 24 pages.
"Disposable PD-10 Desalting Columns," GE Healthcare Life Sciences, downloaded Nov. 1, 2011, 2 pages.
"Desalting and buffer exchange with Sephadex® G-25," Amersham Biosciences, downloaded from www.gelifesciences.com on Jan. 8, 2013, 8 pages.
"Human Albumin," Sigma downloaded from www.sigmaaldrich.com on Jan. 8, 2013, 1 page.
Online Medical Dictionary definition of albumin, medical-dictionary.thefreedictionary.com/albumin, downloaded Nov. 1, 2011, 4 pages.
The Cytokine Handbook, edited by Thomson and Lotze, 4th edition, 2003 Academic Press, vol. I, London, UK, pp. 169, 186, 187, 467, 570, 571, 838, 839, 1189-1193, 1197-1200.
The Cytokine Handbook, edited by Thomson and Lotze, 4th edition, 2003 Academic Press, vol. II, London, UK, pp. 838-860 and 1189-1211.
The Cytokine Handbook, edited by Thomson and Lotze, 4th edition, 2003 Academic Press, vol. I, London, UK, pp. 167-199, 456-474, 567-601.
The Dictionary of Immunology, Fourth Edition, Edited by Herbert et al., 1995, pp. 51-52 and 69.
"Tryprostatin A, Aspergillus fumigates," available at www.emdbiosciences.com/Products/ProductDisplay.asp?catno=649305&, printed on Jun. 21, 2006, 1 page.
Abraha et al., "C-terminal inhibition of tau assembly in vitro and in Alzheimer's disease," Journal of Cell Science, 2000, vol. 113, pp. 3737-3745.
Acharya et al., "Solid-phase synthesis of substituted imidazoline-tethered 2,3-diketopiperazines, cyclic ureas, and cyclic thioureas," J Comb Chem, Nov.-Dec. 2001, vol. 3(6), pp. 612-623.
Adorini, L., "Selective immunointervention in autoimmune diseases: lessons from multiple sclerosis," J Chemother, Jun. 2001, vol. 13(3), pp. 219-234 (Abstract Only Provided).
Akiyama et al., "Inflammation and Alzheimer's disease," Neurobiol Aging, 2000, vol. 21, pp. 383-421.
Albert et al., "ABT-491, a highly potent and selective PAF antagonist, inhibits nasal vascular permeability associated with experimental allergic rhinitis in Brown Norway rats," Inflamm. Res., 1997, Supplement 2, pp. S133-S134.
Alvarez et al., "Isolation and Structure Elucidation of Two New Calpain Inhibitors from Streptomyces Griseus," J. Antibiotics, Nov. 1994, vol. 47(11), pp. 1195-1201.
Andreasen et al., "Cerebrospinal fluid beta-amyloid (1-42) in Alzheimer disease: differences between early- and late-onset Alzheimer disease and stability during the course of disease," Arch. Neurol., Jun. 1999, vol. 56(6), pp. 673-680.
Aoki et al., "In vitro and in vivo differentiation of human embryonic stem cells into retina-like organs and comparison with that from mouse pluripotent epiblast stem cells," Developmental Dynamics, 2009, vol. 238, Iss. 9, pp. 2266-2279.
Arbabi et al., "Priming Interleukin 8 Production: Role of Platelet-Activating Factor and p38," Arch Surg., Dec. 1999, vol. 134(12), pp. 1348-1353.
Ashwood et al. "Is autism an autoimmune disease?" Autoimmunity Reviews, Nov. 2004, vol. 3, No. 7-8, pp. 557-562.

(56) References Cited

OTHER PUBLICATIONS

Au et al., "Effect of PDE4 Inhibitors on Zymosan-Induced IL-8 Release From Human Neutrophils: Synergism with Prostanoids and Salbutamol," Br. J. Pharmacol, 1998, vol. 123, pp. 1260-1266.

Baba et al., "Constitutively Active ß-Catenin Confers Multilineage Differentiation Potential on Lymphoid and Myeloid Progenitors," Immunity, 2005, vol. 23, Iss. 6, pp. 599-609.

Bagaria et al., "Cyclo(L-leucyl-alpha,beta-dehydrophenylalanine): the first diketopiperazine containing an alpha,beta-dehydrophenylalanine residue," Acta Crystallogr C., Mar. 2005, vol. 61(Pt 3), pp. 174-176, Epub Feb. 28, 2005.

Baig et al., "High Performance Liquid Chromatography as a Tool in the Definition of Abnormalities in Monamine and Tryptophan Metabolites in Cerebrospinal Fluid from Patients with Neurological Disorders," Biomed Chromatogr 1991, 5(3):108-112 (Abstract Only Provided).

Balk, "Lesson 24, vol. 12—ARDS: Pathophysiology of SIRS and MODS" www.chestnet.org/education/pccu/vol12/ lesson24.html, pp. 1-19, printed Jul. 20, 2000.

Banks et al., "Radioactively Iodinated Cyclo(His-Pro) Crosses the Blood-Brain Barrier and Reverses Ethanol-Induced Narcosis," Am J Physiol, May 1993, vol. 264(5 Pt. 1), pp. E723-E729 (Abstract Only Provided).

Bar-Or et al. "Commercial human albumin preparations for clinical use are immunosuppressive in vitro," Critical Care Medicine, Jun. 2006, vol. 34, No. 6, pp. 1707-1712.

Bar-Or et al., "An Analog of the Human Albumin N-Terminus (Asp-Ala-His-Lys) Prevents Formation of Copper-Induced Reactive Oxygen Species," Biochemical and Biophysical Research Communications, 2001, vol. 284(3), pp. 856-862.

Bar-Or et al., "Potential Plasma Surrogate Biomakers for CNS Demyelinating Processes," 19th Congress of the European Committee for Treatment and Research in Multiple Sclerosis Meeting; Sep. 17-20, 2003; 2 pp. (Abstract first distributed at the meeting; attached is poster presented at meeting).

Barrow et al., WIN 64821, a New Competitive Antagonist to Substance P, Isolated from an Aspergillus Species: Structure Determination and Solution Conformation, J. Org. Chem., 1993, vol. 58, pp. 6016-6021.

Battersby et al., "Diketopiperazine Formation and N-Terminal Degradation in Recombinant Human Growth Hormone," Int. J. Pept. Protein Res, Sep. 1994, vol. 44(3), pp. 215-222 (Abstract Only Provided).

Berman et al., "Psoriasis," PubMed Health, reviewed Nov. 22, 2011, available at www.ncbi.nlm.nih.gov/pubmedhealth/PMH0001470/?report=printable.

Berry et al., "Inhibition of Tau Polymerization by its Carboxy-Terminal Caspase Cleavage Fragment," Biochemistry, 2003, vol. 42, pp. 8325-8331.

Bhargava et al., "Inhibition of Neuroleptic-Induced Dopamine Receptor Supersensitivity by Cyclo (Leu-Gly)," Pharmacol Biochem Behav, Nov. 1980, vol. 13(5), pp. 633-636 (Abstract Only Provided).

Bhargava, "Antagonism of ketamine-induced anesthesia and hypothermia by thyrotropin releasing hormone and cyclo (His-Pro)," Neuropharmacology, 1981, vol. 20(7), pp. 699-702.

Bhargava, "Inhibition of abstinence syndrome in opiate dependent mice by cyclo (His-Pro)," Life Sci, 1981, vol. 28(11), pp. 1261-1267.

Bhargava, "The effect of melanotrophin release inhibiting factor (MIF) and cyclo (Leu-Gly) on the tolerance to morphine-induced antinociception in the rat: a dose-response study," Br J Pharmacol, Apr. 1981, vol. 72(4) (Abstract Only Provided).

Bhargava, "The effects of thyrotropin releasing hormone and histidyl-proline diketopiperazine on delta-9-tetrahydrocannabinol-induced hypothermia," Life Sci, 1980, vol. 26(11), pp. 845-850.

Bielekova et al., "Development of biomarkers in multiple sclerosis," Brain, Jul. 2004, vol. 127(Pt 7), pp. 1463-1478, Epub Jun. 4, 2004.

Binisti et al., "Structure-Activity Relationships in Platelet Activating Factor," J. Lipid Mediat. Cell Signal, Jan. 1997, vol. 15(2), pp. 125-144 (Abstract Only Provided).

Blazickova et al., "Immunomodulatory Characteristics of Synthetic Cyclic Dipeptides," Int. J. Immunotherapy, 1994, vol. 10(3), pp. 89-93.

Borthwick, "2,5-Diketopiperazines: Synthesis, Reactions, Medicinal Chemistry, and Bioactive Natural Products," Chemical Reviews, 2012, vol. 112, Iss. 7, pp. 3641-3716.

Bowden et al., "Re-evaluation of histidyl-proline diketopiperazine [cyclo (His-Pro)] effects on food intake in the rate," Pharmacol. Biochem. Behav., Feb. 1988, vol. 29(2), pp. 357-363 (Abstract Only Provided).

Brauns et al., "Selected cyclic dipeptides inhibit cancer cell growth and induce apoptosis in HT-29 colon cancer cells," Anticancer Research, 2004, vol. 24, pp. 1713-1720.

Bressan et al., "Coordination chemistry of peptides. Part II. Crystal structure of cyclo-L-methionylglycine and studies of metal complexation," Int J Pept Protein Res, Apr. 1982, vol. 19(4) (Abstract Only Provided).

Bresser et al., "T-Cell Activation in the Lungs of Patients With Systemic Sclerosis and Its Relation With Pulmonary Fibrosis," Chest, Jul. 2001, 6 pages.

Brevini et al., "No shortcuts to pig embryonic stem cells," Theriogenology, 2010, vol. 74, Iss. 4, pp. 544-550.

Brittberg et al., "Treatment of Deep Cartilage Defects in the Knee with Autologous Chondrocyte Transplantation," The New England Journal of Medicine, 1994, vol. 331, No. 14, pp. 889-895.

Brown et al., "Anti-VEGF Agents in the Treatment of Neovascular Age-related Macular Degeneration: Applying Clinical Trial Results to the Treatment of Everyday Patients," American Journal of Opthalmology, 2007, vol. 144, Iss. 4, pp. 627-637.

Bunn, "Early detection of lung cancer using serum RNA or DNA markers: ready for "prime time" or for validation?," J Clin Oncol., Nov. 1, 2003, vol. 21(21), pp. 3891-3893.

Caballero et al., "Brief synthesis of the cell cycle inhibitor tryprostatin B and its alanine analogue," Fourth International Electronic conference of Synthetic Organic Chemistry (ECXOC-4), Sep. 1-13, 2000, 4 pages, available at pages.unibas.ch/mdpi/eecxoc-4/c0023/c0023.htm.

Caballero et al., "Brief total synthesis of the cell cycle inhibitor tryprostatin B and related preparation of its alanine analogue," J Org Chem, Sep. 5, 2003, vol. 68(18) (Abstract Only Provided).

Carlton et al., "Attenuation of alcohol-induced hypothermia by cycle (His-Pro) and its analogs," Neuropeptides, Jun. 1995, vol. 28(6), pp. 351-355 (Abstract Only Provided).

Chan, "Chapter 9: Transplant Rejection and Its Treatment," Atlas of Diseases of the Kidney, vol. 5, (Ed.Henrich et al.), Wiley-Blackwell, 1999, pp. 9.1-9.13.

Chan et al., "Site-Specific N-Terminal Auto-Degradation of Human Serum Albumin," Eur. J. Biochem., 1995, vol. 227, pp. 524-528.

Chen et al., "Up-regulation of Platelet-activating Factor Receptors in Lung and Alveolar Macrophages in the Bleomycin-Hamster Model of Pulmonary Fibrosis," J. Pharmacol. Exp. Ther., 1997, vol. 280(3), pp. 1219-1227.

Cho et al., "Contribution of Natural Inhibitors to the Understanding of the PI3K/PDK1/PKB Pathway in the Insulin-mediated Intracellular Signaling Cascade," Int. J. Mol. Sci., 2008, vol. 9, pp. 2217-2230.

Chute, "Stem cell homing," Current Opinion in Hematology, 2006, vol. 13, Iss. 6, pp. 399-406.

Ciarkowski et al., "Conformation of cyclo-(D-phenylalanyl-trans-4-fluoro-D-prolyl)," Int. J. Pept. Protein Res., vol. 36, Sep. 1990, pp. 285-291.

Clark et al., "Roquefortine E, a Diketopiperazine from an Australian Isolate of Gymnoascus reessii," J. Nat. Prod., 2005, vol. 68(11), p. 1661-1664 (Abstract Only Provided).

Cody et al., "The design of potent and selective inhibitors of thrombin utilizing a piperazinedione template: part 2," Bioorg Med Chem Lett, Sep. 6, 1999, vol. 9(17), pp. 2503-2508.

(56) References Cited

OTHER PUBLICATIONS

Coggins et al., "High Affinity Specific Binding of the Thyrotrophin Releasing Hormone Metabolite Histidylproline to Rat Brain Membranes," Neuropeptides, Jan. 1987, vol. 9(1), pp. 83-91 (Abstract Only Provided).
Collins et al., "Ex vivo culture systems for hematopoietic cells," Current Opinion in Biotechnology, 1996, vol. 7, Iss. 2, pp. 223-230. Abstract Only.
Cong et al., "Histone Deacetylation is Involved in the Transcriptional Repression of hTERT in Normal Human Cells," The Journal of Biological Chemistry, 2000, vol. 275, No. 46, pp. 35665-35668.
Costa et al., "Aggregation of features of the metabolic syndrome is associated with increased prevalence of chronic complications in Type 2 diabetes," Diabetic Medicine, 2004, vol. 21, Iss. 3, 252-255.
Couladouros et al., "Solid-phase total synthesis of (-)-Phenylhistine and (-)-Aurantiamine. Synthesis of a diverse dehydro-2,5-diketopiperazine library. Part II," Mol Divers., 2005, vol. 9(1-3), pp. 111-121.
Crowe et al., "The N Terminal Region of Human Tau is Present in Alzheimer's Disease Protein A68 and is Incorporated into Paired Helical Filaments," American Journal of Pathology, 1991, vol. 139(6), pp. 1463-1470.
Cruse et al., "Illustrated Dictionary of Immunology" Second Edition, 2003, pp. 192, 260, 530-531.
Cui et al., "Novel Mammalian Cell Cycle Inhibitors, Tryprostatins A, B and Other Diketopiperazines Produced by Aspergillus fumigatus II. Physico-chemical properties and Structures," The Journal of Antibiotics, Jun. 1996, pp. 534-540.
D'Alagni et al. "Effect of Urea on the Optical Rotatory Dispersion of Diketopiperazines of l-Serine, l-Alanine, l-Lysine, l-Valine, and l-Valylglycine." The Journal of Biological Chemistry, Nov. 10, 1969, vol. 244, No. 21, pp. 5843-5848.
D'Amour et al., "Production of pancreatic hormone-expressing endocrine cells from human embryonic stem cells," Nature Biotechnology, 2006, vol. 24, No. 11, pp. 1392-1401.
Davidson et al., "Autoimmune Diseases," N. Engl. J. Med, 2001, vol. 345(5), pp. 340-350.
De Felice et al., "Histone Deacetylase Inhibitor Valproic Acid Enhances the Cytokine-Induced Expansion of Human Hematopoietic Stem Cells," Cancer Research, 2005, vol. 65, Iss. 4, pp. 1505-1513.
De La Cruz et al, "Effect of WEB 2086-BS, an antagonist of platelet-activating factor receptors, on retinal vascularity in diabetic rats," European Journal of Pharmacology, 1998, vol. 360, Iss. 1, pp. 37-42.
Degrassi et al., "Plant Growth-Promoting Pseudomonas putida WCS358 Produces and Secretes Four Cyclic Dipeptides: Cross-Talk with Quorum Sensing Bacterial Sensors," Current Microbiology, 2002, vol. 45, pp. 250-254.
Del Fresno et al. "Solid-phase synthesis of diketopiperazines, useful scaffolds for combinatorial chemistry," Tetrahedron Letters, 1998, vol. 39, Iss. 17, pp. 2639-2642.
Denault et al., "Transcriptional activation of the interleukin-8 gene by platelet-activating factor in human peripheral blood monocytes," Immunology, 1997, vol. 91, pp. 297-302.
Diamanti et al., "Distribution and Characterization of Cyclo (His-Pro)-like Immunoreactivity in the Human Gastrointestinal Tract," Neuropeptides, Mar. 1985, vol. 6(1):21-5 (Abstract Only Provided).
Dirr, K. et al., "The transformation of arginine into citrulline," Z. Physiol. Chem., 1935, vol. 237, pp. 121-130.
Drukker e al., "Characterization of the expression of MHC proteins in human embryonic stem cells," Proceedings of the National Academy of Sciences of the United States of America, 2002, vol. 99, No. 15, pp. 9864-9869.
Duntas et al., "A Fast Protein Liquid Chromatography (FPLC) Method for Study of Thyrotropin-releasing Hormone (TRH) and its metabolite Histidyl-Proline Diketopiperazine (CHP) in Human Blood: Degradation in Liver and Pancreatic Diseases," Neuropeptides, 1993, vol. 25(6), pp. 357-361 (Abstract Only Provided).
Ekser et al., "Clinical xenotransplantation: the next medical revolution?," The Lancet, 2012, vol. 379, No. 9816, pp. 672-683.

Esposito et al., "The Solution Structure of the C-Terminal Segment of Tau Protein," Journal of Peptide Science, 2000, vol. 6, pp. 550-559.
Evans et al. "Metabolic effects of platelet-activating factor in rats in vivo: Stimulation of hepatic glycogenolysis and lipogenesis." Biochemical Journal, Jul. 1990, vol. 269, No. 1, pp. 269-272.
Faden et al., "Neuroprotective and nootropic actions of a novel cyclized dipeptide after controlled cortical impact injury in mice." J. Cerebral Blood Flow & Metabolism, 2003, vol. 23, pp. 355-363.
Faden et al., "Novel diketopiperazine enhances motor and cognitive recovery after traumatic brain injury in rats and shows neuroprotection in vitro and in vivo," J. Cerebral Blood Flow & Metabolism, 2003, vol. 23, pp. 342-354.
Faden et al., "Novel neuroprotective Tripeptides and Dipeptides," Ann. N.Y. Acad. Sci, 2005, vol. 1053, pp. 472-481.
Faden et al., "Novel small peptides with neuroprotective and nootropic properties," J. Alzheimer's Dis, 2004, vol. 6, pp. S93-S97.
Faden et al., "Novel TRH analog improves motor and cognitive recovery after traumatic brain injury in rodents," Am J Physiol, Oct. 1999, vol. 277(4 Pt 2), pp. R1196-R1204.
Falorni et al. "Chiral ligands containing heteroatoms. 11. Optically active 2-hydroxymethyl piperazines as catalysts in the enantioselective addition of diethylzinc to benzaldehyde," Tetrahedron: Asymmetry, 1993, vol. 4, Iss. 11, pp. 2389-2398.
Falorni et al. "Chiral ligands containing heteroatoms. 11. Optically active 2-hydroxymethyl piperazines as catalysts in the enantioselective addition of diethylzinc to benzaldehyde," Tetrahedron: Asymmetry, 1993, vol. 4, Iss. 11, pp. 2389-2398. (Abstract and Graphic only).
Fdhila et al., "dd-diketopiperazines: antibiotics active against Vibrio anguillarum isolated form marine bacteria associated with cultures of Pecten maximus" J Nat Prod, Oct. 2003, vol. 66(10) (Abstract Only Provided).
Fischer, "Diketopiperazines in Peptide and Combinatorial Chemistry," Journal of Peptide Science, 2003, vol. 9, pp. 9-35.
Folkes et al., "Synthesis and in vitro evaluation of a series of diketopiperazine inhibitors of plasminogen activator inhibitor-1," Bioorg Med Chem Lett, Oct. 2001, vol. 11(19), pp. 2589-2592 (Abstract Only Provided).
Fragner et al., "A New Biological Contribution of Cyclo(His-Pro) to the Peripheral Inhibition of Pancreatic Secretion," Am J Physiol, Dec. 1997, vol. 273(6 Pt. 1), pp. E1127-E1132 (Abstract Only Provided).
Gamblin et al., "Tau Polymerization: Role of the Amino Terminus," Biochemistry, 2003, vol. 42(7), pp. 2252-2257.
Garcia-Sierra et al., "Conformational Changes and Truncation of Tau Protein during Tangle Evolution in Alzheimer's Disease," Journal of Alzheimer's Disease, 2003, vol. 5, pp. 65-77.
Gomez et al., "Low-Dose Dopamine Agonist Administration Blocks Vascular Endothelial Growth Factor (VEGF)-Mediated Vascular Hyperpermeability without Altering VEGF Receptor 2-Dependent Luteal Angiogenesis in a Rat Ovarian Hyperstimulation Model," Endocrinology, 2006, vol. 147, No. 11, pp. 5400-5411.
Goolcharran et al., "Comparison of the Rates of Deamidation, Diketopiperazine Formation and Oxidation in Recombinant Human Vascular Endothelial Growth Factor and Model Peptides," AAPS PharmSci, 2000 vol. 2(1), p. E5 (Abstract Only Provided).
Gorbitz "Crystal and Molecular Structure of cyclo-L-Aspartyl-L-alanyl (3,6-Dioxo-5-methyl-2-piperazineacetic acid)" Acta Chemica Scandinavica B, 1987, vol. 41, pp. 83-86.
Gorbitz, "Crystal and molecular structures of the isomeric dipeptides alpha-L-aspartyl-L-alanine and beta-L-aspartyl-L-alanine," Acta Chem Scand B., vol. 41(9), Oct. 1987, pp. 679-685.
Gordon et al, "Reductive Alkylation on a Solid Phase: Synthesis of a Piperazinedione Combinatorial Library," Bioorganic & Medicinal Chemistry Letters, 1995, vol. 5, No. 1, p. 47-50.
Gotoh et al., "Cross-linking of integrins induces tyrosine phosphorylation of the proto-oncogene product Vav and the protein tyrosine kinase Syk in human factor-dependent myeloid cells," Cell Growth & Differentiation, 1997, vol. 8, Iss. 6, pp. 721-729.

(56) References Cited

OTHER PUBLICATIONS

Gountopoulou et al. "TNFα is a potent inducer of platelet-activating factor synthesis in adipocytes but not in preadipocytes. Differential regulation by PI3K." Cytokine, Jan. 2008, vol. 41, No. 2 p. 174-181, (Abstract Only).
Granero-Moltó et al., "Regenerative Effects of Transplanted Mesenchymal Stem Cells in Fracture Healing," Stem Cells, 2009, vol. 27, Iss. 8, pp. 1887-1898.
Graz et al "Cyclic Dipeptides in the Induction of Maturation for Cancer Therapy," J. Pharm. Pharmacol., 2000, vol. 52, pp. 75-82.
Graz et al., "Mechanism of a anti-fungal action of selected cyclic dipeptides," Pharmazie, Nov. 2001, vol. 56(11), pp. 900-901.
Gross et al., "Regulation of Interleukin-8 Production in a Human Colon Epithelial Cell Line (HT-29)," Gastroenterology, 1995, vol. 108, pp. 653-661.
Grubek-Jaworska et al., "CD4/CD8 lymphocytes in BALF during the efferent phase of lung delayed-type hypersensitivity reaction induced by single antigen inhalation," Med Sci Monit, Sep.-Oct. 2001, vol. 7(5), pp. 878-883 (Abstract Only Provided).
Gu et al., "Diketopiperazine Formation, Hydrolysis, and Epimerization of the New Dipeptide Angiotensin-Converting Enzyme Inhibitor RS-10085," Pharm Res, 1987, vol. 4(5), pp. 392-397 (Abstract Only Provided).
Gudasheva et al., "Anxiolytic activity of endogenous nootropic dipeptide cycloprolylglycine in elevated plus-maze test," Bull Exp Biol Med, May 2001, vol. 131(5) (Abstract Only Provided).
Gudasheva et al., "Identification of a novel endogenous memory facilitating cyclic dipeptide cyclo-prolylglycine in rat brain," FEBS Lett, Aug. 5, 1996, vol. 391(1-2) (Abstract Only Provided).
Guerra et al., "PEGylation Prevents the N-Terminal Degradation of Megakaryocyte Growth and Development Factor," Pharm Res, 1998, vol. 15(12), pp. 1822-1827 (Abstract Only Provided).
Gustafson, "Adipose Tissue, Inflammation and Atherosclerosis," J. Atheroscler. Thromb., Apr. 30, 2010, vol. 17(4), pp. 332-341.
Hansel et al. "Metabolic Syndrome is Associated with Elevated Oxidative Stress and Dysfunctional Dense High-Density Lipoprotein Particles Displaying Impaired Antioxidative Activity." The Journal of Clinical Endocrinology & Metabolism, Oct. 2004, vol. 89, No. 10, pp. 4963-4971.
Harada et al., "Essential involvement of interleukin-8 (IL-8) in acute inflammation," Journal of Leukocyte Biology, 1994, vol. 56, Iss. 5, pp. 559-564.
Hasegawa et al., "Protein Sequence and Mass Spectrometric Analysis of Tau in the Alzheimer's Disease Brain," Journal of Biological Chemistry, 1992, vol. 267(24), pp. 17047-17054.
Hayashi et al., "Synthetic Hexa- and Heptapeptides That Inhibit IL-8 from Binding to and Activating Human Blood Neutrophils1," J. Immunol., 1995, vol. 154, pp. 814-824.
He et al., "Evidence for a Role of Platelet-Activating Factor (PAF) in the Pathogenesis of Age-Related Macular Degeneration (AMD)", Investigative Ophthalmology & Visual Science, 2007, vol. 48, Iss. 13, 2 pages. (Abstract only).
He et al., "Wnt Signaling in Stem Cells and Non-Small-Cell Lung Cancer," Clinical Lung Cancer, 2005, vol. 7, Iss. 1, pp. 54-60.
Heng et al. "Transplanted human embryonic stem cells as biological 'catalysts' for tissue repair and regeneration," Medical Hypotheses, 2005, vol. 64, Iss. 6, pp. 1085-1088.
Hilton et al., "Food Contains the Bioactive Peptide, Cyclo(His-Pro)," J. Clin Endocrinol Metab, Aug. 1992, vol. 75(2), pp. 375-378 (Abstract Only Provided).
Hilton et al., "Identification and Characterization of Cyclo (His-Pro)-Like Immunoreactivity in Amniotic Fluid," Peptides, Mar.-Apr. 1989, vol. 10(2), pp. 299-301 (Abstract Only Provided).
Hilton et al., "Radioimmunoassay of Cyclo(His-Pro) in Unextracted Human Plasma: Report of a Normal Range and Definition of Factors Critical for Successful Assay," Neuropeptides, 1989, vol. 13(1), pp. 65-70 (Abstract Only Provided).
Hilton et al., "Relationship between Plasma Cyclo (His-Pro), a Neuropeptide Common to Processed Protein-Rich Food, C-Peptide/Insulin Molar Ratio in Obese Women," Nutr Neurosci, 2001, vol. 4(6), pp. 469-474 (Abstract Only Provided).
Hlinak et al., "Effect of alaptide, its analogues and oxiracetam on memory for an elevated plus-maze in mice," European Journal of Pharmacology, 1996, vol. 314, pp. 1-7.
Hoffman et al., "An Enzymatically Stable Peptide with activity in the Central Nervous System: Its Penetration through the Blood-CSF Barrier," Brain Res, Feb. 11, 1977, vol. 122(1), pp. 87-94 (Abstract Only Provided).
Holden et al., "Quorum-sensing cross talk: isolation and chemical characterization of cyclic dipeptides from Pseudomonas aeruginosa and other Gram-negative bacteria," Moleclur Microbiology, 1999, vol. 33(6), pp. 1254-1266.
Hollyfield et al., "Oxidative damage-induced inflammation initiates age-related macular degeneration," Nature Medicine, 2008, vol. 14, No. 2, pp. 194-198.
Hong et al., "Inhibitory effect against Akt of cyclic dipeptides isolated from *Bacillus* sp" J. Microbiol. Biotechnol., 18, 682-685 (2008).
Hou et al., "The Histone Deacetylase Inhibitor Trichostatin A Derepresses the Telomerase Reverse Transcriptase (hTERT) Gene in Human Cells," Experimental Cell Research, 2002, vol. 274, Iss. 1, pp. 25-34.
Houston et al., "The cyclic dipeptide CI-4 [cyclo-(I-Arg-d-Pro)] inhibits family 18 chitinases by structural mimicry of a reaction intermediate," Biochem J., Nov. 15, 2002, vol. 368(Pt 1) (Abstract Only Provided).
Horwitz et al., "Piperazinedione plus total body irradiation: an alternative preparative regimen for allogeneic bone marrow transplantation in advanced phases of chronic myelogenous leukemia," Bone Marrow Transplantation, 1989, vol. 4, Iss. 1, pp. 101-105.
Howitz et al., "Small molecule activators of sirtuins extend *Saccharomyces cerevisiae* lifespan," Nature, 2003, vol. 425, No. 6954, pp. 191-196.
Hwang et al., "Effects of cyclo (his-pro) plus zinc on glucose metabolism in genetically diabetic obse mice," Diabetes Obes. Metab., Sep. 2003, vol. 5(5), pp. 317-324 (Abstract Only Provided).
Iriuchijima et al., "Thyrotripin-Releasing Hormone and Cyclo (His-Pro)-Like Immunoreactivities in the Cerebrospinal Fluids of 'Normal' Infants and Adults, and Patients with Various Neuropsychiatric and Neurologic Disorders," Life Sci. 1987, 41(22):2419-2428, Abstract only, from PubMed-PMID:2891013.
Ishibashi et al., "A Mechanism for Bitter Taste Sensibility in Peptides," Agric. Biol. Chem., 1988, vol. 52(3), pp. 819-827.
Ishibashi et al., "Bitterness of Leucine-Containing Peptides," Agric. Biol. Chem., 1987, vol. 51 (9), pp. 2389-2394.
Ishii, et al. "Incidence of brain tumors in rats fed aspartame," Toxicology Letters, 1981, vol. 7, pp. 433-437.
Ivanovic et al., "Hypoxia maintains and interleukin-3 reduces the pre-colony-forming cell potential of dividing CD34+ murine bone marrow cells," Experimental Hematology, 2002, vol. 30, Iss. 1, pp. 67-73.
Iyer et al. "Inflammatory lipid mediators in adipocyte function and obesity." Nature Reviews Endocrinology, Feb. 2010, vol. 6, pp. 71-82.
Jackson et al., "Amyotrophic Lateral Sclerosis: Thryrotropin-releasing hormone and histidyl proline diketopiperazine in the spinal cord and cerebrospinal fluid," Neurology, 1986, vol. 36(9), pp. 1218-1223.
Jamie et al., "The effect of the isomers of cyclo(Trp-Pro) on heart and ion-channel activity," J Pharm Pharmacol, Dec. 2002, vol. 54(12) (Abstract Only Provided).
Jara et al., "Elevated serum levels of cyclo (His-Pro), and endogenous inhibitor ofpituitary prolactin secretion, in systemic lupus erythematosus patients," Lupus, 1997, vol. 6(3) (Abstract Only Provided).
Jaspan et al., "Study of Passage of Peptides Across the Blood-Brain Barrier: Biological Effects of Cyclo(His-Pro) After Intravenous and Oral Administration," Annals of the New York Academy of Science, 1994, vol. 739, pp. 101-107 (Abstract Only Provided).
Jiang et al. "Asymmetric Reformastky reaction catalyzed by amino acid derivatives," Huaxue Tongbao CKNI, 2001, vol. 10, pp. 637-640 (English Abstract).

(56) References Cited

OTHER PUBLICATIONS

Jiang et al., "AKT signaling in regulating angiogenesis," Current Cancer Drug Targets, 2008, vol. 8, pp. 19-26.

Jicha et al., "Sequence Requirements for Formation of Conformational Variants of Tau Similar to Those Found in Alzheimer's Disease," Journal of Neuroscience Research, 1999, vol. 55, pp. 713-723.

Jung et al., "Ex Vivo Expansion of Human Mesenchymal Stem Cells in Defined Serum-Free Media," Stem Cells International, 2012, Article ID 123030, 21 pages.

Kaakkola et al., "Effects of two diketopiperazines, cyclo (His-Pro) and cyclo (Asp-Phe), on striatal dopamine: A microdialysis study," Brain Research Bulletin, 1993, vol. 32(6), pp. 667-672.

Kanzaki et al., "Enzymatic synthesis of dehydro cyclo(His-Phe)s, analogs of the potent cell cycle inhibitor, dehydrophenylahistin, and their inhibitory activities toward cell division," Biosci Biotechnol Biochem, Nov. 2004, vol. 68(11), pp. 2341-2345 (Abstract Only Provided).

Kasperska-Zajac et al. "Platelet Activating Factor as a Mediator and Therapeutic Approach in Bronchial Asthma." Inflammation, Apr. 2008, vol. 31, No. 2, pp. 112-120.

Kikwai et al, "Stability and degradation profiles of Spantide II in aqueous solutions," Eur J Pharm Sci, Feb. 2006, vol. 27(2-3), pp. 158-166, Epub Nov. 2, 2005. (Abstract Only Provided).

Kilian et al., "Biological activity of selected tyrosine-containing 2,5-diketopiperazines," Pharmazie, Apr. 2005, vol. 60(4), pp. 305-309 (Abstract Only Provided).

Kilian et al., "The effect of the isomer of cyclo(Trp-Pro) on heart and ion-channel activity," J. Pharm. Pharmacol., Dec. 2002, vol. 54(12), pp. 1659-1665 (Abstract Only Provided).

Kobayashi et al., "Neuropeptide Y and histidyl-proline diketopiperazine," Rinsho-Kensa, Japan, Sep. 1987, vol. 21, No. 9, pp. 984-991.

Kopple et al. "Conformation of Cyclo-(I-Threonine)2 and Cyclo-(I-Allothreonine)2 : A Proton and Carbon N.m.r. Study." International Journal of Peptide Protein Research, Jul. 1981, vol. 18, No. 1, pp. 33-40.

Koskinen, "Effect of Low Intravenous Doses of TRH, Acid-TRH and Cyclo (His-Pro) on Cerebral and Peripheral Blood Flows," British Journal of Pharmacology, 1986, vol. 87(3), pp. 509-519 (Abstract Only Provided).

Kow et al., "The Effects of the TRH Metabolite Cyclo(His-Pro) and Its Analogs on Feeding," Pharmacology, Biochemistry & Behavior, 1991, vol. 38, pp. 359-364.

Kuenz et al., "Plasma levels of soluble adhesion molecules sPECAM-1, sP-selectin and sE-selectin are associated with relapsing-remitting disease course of multiple sclerosis," J. Neuroimmunol, Oct. 2005, vol. 167(1-2), pp. 143-149.

Kulikov et al., "Review: The Bioregulatory Role of Platelet-Activating Factor in Intracellular Processes and Cell—Cell Interactions," 1997, www.protein.bio.msu.su/biokhimiya/contents/v63/full/63010057.html, pp. 1-13.

Kullenberg et al., "Intraarticular Corticosteroid Injection: Pain Relief in Osteoarthritis of the Hip?," Journal of Rheumatology, 2004, vol. 31, No. 11, pp. 2265-2268.

Kurahashi et al., "Histydyl-Proline Diketopiperazine (HPD), A Metabolite of Thyrotropin-Releasing Hormone (TRH), Improves the Ataxic Gait in 3-Acetylpyridine (3-AP) Treated Rats," No To Shinkei, Sep. 1986, vol. 38(9), pp. 893-898 (Abstract Only Provided).

Larsen et al. "Kinetics of degradation and oil solubility of ester prodrugs of a model dipeptide (Gly-Phe)," Eur J Pharm Sci, Aug. 2004, vol. 22(5), pp. 399-408 (Abstract Only Provided).

Le Blanc et al. "Treatment of severe acute graft-versus-host disease with third party haploidentical mesenchymal stem cells," The Lancet, 2004, vol. 363, Iss. 9419, pp. 1439-1441.

Lechan et al., "Thyrotropin Releasing Hormone but not Histidyl-Proline Diketopiperazine is Depleted from Rat Spinal Cord Following 5,7-Dihydroxytryptamine Treatment," Brain Research, 1985, vol. 326(1), pp. 152-155 (Abstract Only Provided).

Lechin et al., "Plasma Neurotransmitters and Cortisol in Chronic Illness: Role of Stress," J Medicine, 1994, vol. 25(3-4), pp. 181-192 (Abstract Only Provided).

Leduque et al., "Histidyl-Proline Diketopiperazine (His-Pro DKP) Immunoreactivity is Present in the Glucagon-Containing Cells of the Human Fetal Pancreas," J Clin Invest, 1987, 79(3):875-880 (Abstract Only Provided).

Lse et al., "Characterization of an Elastase Inhibitor Produced by Streptomyces lavendulae SMF11," Journal of Microbiology and Biotechnology, 2000, vol. 10, No. 1, pp. 81-85.

Lee et al., "Cyclo (Leu-Gly attenuates the striatal dopaminergic supersensitivity induced by chronic morphine," Alcohol Drugs Res, 1987, vol. 7(1) (Abstract Only Provided).

Lehninger et al., "Amino Acids and Peptides," Chapter 5 of Principles of Biochemistry, 1993, 2nd edition, pp. 111-133.

Lewis et al., "Hydrogen Peroxide Stimulates the Synthesis of Platelet-activating Factor by Endothelium and Induces Endothelial Cell-dependent Neutrophil Adhesion," The Journal of Clinical Investigation, 1988, vol. 82, Iss. 6, pp. 2045-2055.

Li et al., "Effects of Administration Route on Migration and Distribution of Neural Progenitor Cells Transplanted into Rats with Focal Cerebral Ischemia, an MRI Study," Journal of Cerebral Blood Flow & Metabolism, 2010, vol. 30, No. 3, pp. 653-662.

Lin et al., "Coagulation dysregulation as a barrier to xenotransplantation in the primate," Transplant Immunology, 2009, vol. 21, Iss. 2, pp. 75-80.

Lindsley et al., "Allosteric Akt (PKB) inhibitors: discovery and SAR of isozyme selective inhibitors," Bioorganic & Medicinal Chemistry Letters, 2005, vol. 15, Iss. 3, pp. 791-764.

Lindner et al., "[Effects of cyclic adenosine-3',5'-monophosphate and cyclo{Lys-Pro}.HCl neuronotrophic factors in tissue culture]," J Hirnforsch, 1987, vol. 28(3) (Abstract Only Provided).

Liu et al., "Hydroxyprolylserine derivatives JBP923 and JBP485 exhibit the antihepatitis activities after gastrointestinal absorption in rats," J Pharmacol Exp Ther, Aug. 2000, vol. 294(2) (Abstract Only Provided).

Luca et al., "Determination of serotonin content and ceruloplasmin activity, of blood and CSF amino acid level in multiple sclerosis," Neurol Psychiatr (Bucur), 1986, vol. 24(3), pp. 153-159.

Lucietto et al., "The biological activity of the histidine-containing diketopiperazines cyclo (His-Ala) and cyclo (His-Gly)," Peptides, Nov. 2006, vol. 27(11), pp. 2706-2714, Epub Jun. 21, 2006 (Abstract Only Provided).

Lupia et al., "Role of tumor necrosis factor-α and platelet-activating factor in neoangiogenesis induced by synovial fluids of patients with rheumatoid arthritis," European Journal of Immunology, 1996, vol. 26, Iss. 8, pp. 1690-1694.

Ma et al., "Platelet-Activating Factor (PAF) Induces Corneal Neovascularization and Upregulates VEGF Expression in Endothelial Cells," Investigative Ophthalmology & Visual Science, 2004, vol. 45, No. 9, pp. 2915-2921.

Matejschuk et al., "Production of human albumin solution: a continually developing colloid," British Journal of Anaesthesia, 2000, vol. 85, Iss. 6, pp. 887-895.

Mayer, "Immunology—Chapter Four," Immunoglobulins—Structure and Function, online at pathmicro.med.sc.edu/mayer/IgStruct2000.htm, University of South Carolina School of Medicine, Nov. 6, 2009, 8 pages.

Mazza et al., "Potential energy calculations on phenylalanine rotamers in different boat forms of proline-containing cyclic dipeptides," Int. J. Pept. Protein Res., vol. 31, Feb. 1988, pp. 157-163.

McAdams et al., "Hematopoietic cell culture therapies (Part I): cell culture considerations," Trends in Biotechnology, 1996, vol. 14, Iss. 9, pp. 341-349.

McCain et al., "Endorphinergic modulation of immune function: potent action of the dipeptide glycyl-L-glutamine," Life Science, 1987, vol. 41, pp. 169-176.

McCain et al., "Modulation of Human T-Cell Suppressor Activity by Beta Endorphin and Glycyl-L-Glutamine," Int. J. Immunopharmoc, 1986, vol. 8(4), pp. 443-446.

(56) References Cited

OTHER PUBLICATIONS

McCleland et al., "An investigation into the biological activity of the selected histidine-containing diketopieperazines cyclo(His-Phe) and cyclo(His-Tyr)," Journal of Pharmacy and Pharmacology, Sep. 2004, vol. 56(9), pp. 1143-1153.
Meester et al., "In Vivo Inhibition of Dipeptidyl Peptidase IV Activity by Pro-Pro-diphenyl-phosphonate (Prodipine)," Biochemical Pharmacology, 1997, vol. 54, pp. 173-179.
Meltzer, "Efficacy and patient satisfaction with cromolyn sodium nasal solution in the treatment of seasonal allergic rhinitis: a placebo-controlled study," Clinical Therapeutics, 2002, vol. 24, Iss. 6, pp. 942-952.
Mentlein et al., "Dipeptidyl-Peptidase IV Hydrolyses Gastric Inhibitory Polypeptide, Glucagon-Like Peptide-1(7-36)amide, Peptide Histidine Methionine and is Responsible for their Degradation in Human Serum," European Journal of Biochemistry, 1993, vol. 214(3), pp. 829-835 (Abstract Only Provided).
Mesh, "Autoimmune Diseases," internet document www.ncbi.nlm.nih.gov/sites/entrez, accessed Oct. 31, 2007, 2 pages.
Michell et al., "Biomarkers and Parkinson's Disease," Brain, Aug. 2004, vol. 127, pp. 1693-1705.
Migliaccio et al., "Chapter 6: Serum-Deprived Cultures of Primary Hematopoietic Cells," Culture of Hematopoietic Cells, Ed. Freshney, Wiley-Liss, NY, 1994, pp. 81-98.
Miller et al., "Peptide Inhibitor of Interleukin-8 (IL-8) Reduces Staphylococcal Enterotoxin-A (SEA) Induced Neutrophil Trafficking to the Lung," Inflamm. Res., 1996, vol. 45, pp. 393-397.
Milne, et al. "The biological activity of selected cyclic dipeptides," J. Pharm. Pharmacol., 1998, vol. 50, pp. 1331-1337.
Minelli et al., "Phosphoproteomic analysis of the effect of cyclo-[His-Pro] dipeptide on PC12 cells." Peptides, Jan. 2006;27(1):105-13. Epub Aug. 30, 2005., Abstract only PMID: 16137790.
Mitsuma et al., "Radioimmunoassay for Thyrotropin-Releasing Hormone Precursor Peptide, Lys-Arg-Gln-His-Pro-Gly-Arg-Arg," Exp Clin Endocrinology, 1989, vol. 93(1), pp. 53-60 (Abstract Only Provided).
Mizuma et al., "Concentration-Dependent Preferences of Absorptive and Excretive Transport Cause Atypical Intestinal Absorption of Cyclic Phenylalanylserine: Small Intestine Acts as an Interface Between the Body and Ingested Compounds," Research Communications in Molecular Pathology and Pharmacology, 2002, vol. 111, pp. 199-209.
Mizuma et al., "Intestinal Absorption of Stable Cyclic Glycylphenylalanine: Comparison with the Linear Form," J. Pharm. Pharmacol., 1997, vol. 49, pp. 1067-1071.
Molodavkin et al., "[Effect of the novel dipeptide nootropic agent noopept and its metabolite cyclo-L-prolylglycine on the transcallosal evoked potential in the rat brain]," Eksp Klin Farmakol, Mar.-Apr. 2002, vol. 65(2) (Abstract Only Provided).
Monaco et al., "Plasma and cerebrospinal fluid tryptophan in Multiple Sclerosis and Degenerative Diseases," J Neurol Neurosurg Psychiatry, 1979, vol. 42(7), pp. 640-641 (Abstract Only Provided).
Montine et al., "Cerebrospinal Fluid Ab42, Tau, and F2-Isoprostane Concentrations in Patients with Alzheimer Disease, Other Dementias, and in Age-Matched Controls," Acrch Pathol Lab. Med, Apr. 2001, vol. 125, pp. 510-512.
Mori et al., "Alteration by Liquid Protein Diet of TRH and Cyclo(His-Pro) in the Young Rat Brain," Res. Commun Chem Pathol Pharmacol, 1985, vol. 47(1), pp. 157-160 (Abstract Only Provided).
Mori et al., "Brain TRH and Cyclo (His-Pro) and Brain Protein in the Newborn Rat are Altered by Maternal Liquid Protein Feeding," Life Sci, 1983, vol. 32(14), pp. 1607-1612 (Abstract Only Provided).
Mori et al., "Distribution of histidyl-proline diketopiperazine [cyclo (His-Pro)] and thyrotropin-releasing hormone (TRH) in the primate central nervous system," Brain Res, 1982, vol. 245(1), pp. 183-186.
Mori et al., "Histidyl-Proline Diketopiperazine Cyclo (His-Pro): Identification and Characterization in Rat Pancreatic Islets," Biochem Biophys Res Commun, 1983, vol. 115(1), pp. 281-286 (Abstract Only Provided).
Mori et al., "Histidyl-Proline Diketopiperazine cyclo (His-pro): measurement by radioimmunoassay in human blood in normal subject and in patients with hyper- and hypothyroidism," Biochem Biophys Res Commun, 1982, vol. 109(2), pp. 541-547.
Mori et al., "Regional Dissociation of Histidyl-Proline Diketopiperazine (Cyclo-(His-Pro)) and Thyrotropin-Releasing Hormone (TRH) in the Rat Brain," Brain Research, 1982, vol. 231(2), pp. 451-453 (Abstract Only Provided).
Mori et al., "Specific Radioimmunoassay of Cyclo (His-Pro), a Biologically Active Metabolite of Thyrotropin-Releasing Hormone," Endocrinology, 1981, vol. 108(5), pp. 1995-1997 (Abstract Only Provided).
Mori et al., ["TRH and Cyclo (His-Pro) Concentrations in the Young Rat Brain are Altered by a Liquid Protein Diet]," [Article in Japanese], Nippon Naibunpi Gakkai Zasshi, 1987, vol. 63(7), pp. 846-852 (English Abstract Only).
Morley et al., "Histidyl-proline diketopiperazine decreases food intake in rats," Brain Research, 1981, vol. 210, Iss. 1-2, pp. 475-478.
Morley et al., "Neuropeptides and appetite: contribution of neuropharmacological modeling," Fed. Proc., Nov. 1984, vol. 43(14), pp. 2903-2907 (Abstract Only Provided).
Moss et al. "Th1/Th2 cells in inflammatory disease states: therapeutic implications," Expert Opinion on Biological Therapy, Dec. 2004, vol. 4, No. 12, pp. 1887-1896.
Moss et al., "Kinetics and Mechanism of the Facile Cyclization of Histidyl-Prolineamide to Cyclo (His-Pro) in Aqueous Solution and the Competitive Influence of Human Plasma," J Pharm Pharmacol, 1990, vol. 42(1), pp. 7-12 (Abstract Only Provided).
Mukhopadhyay et al., "Histone deacetylation is directly involved in desilencing the expression of the catalytic subunit of telomerase in normal lung fibroblast," Journal of Cellular and Molecular Medicine, 2005, vol. 9, Iss. 3, pp. 662-669.
Muñoz et al., "Conventional pluripotency markers are unspecific for bovine embryonic-derived cell-lines," Theriogenology, 2008, vol. 69, Iss. 9, pp. 1159-1164.
Murray et al., "Role of α-Synuclein Carboxy-Terminus on Fibril Formation in Vitro," Biochemistry, 2003, vol. 42, pp. 8530-8540.
Nakamura et al., "T-cell mediated inflammatory pathway in osteoarthritis," Osteoarthritis & Cartilage, 1999, vol. 7, pp. 401-402.
Neustadt, "Intra-articular injections for osteoarthritis of the knee," Cleveland Clinic J. Med., 2006, vol. 73(10), pp. 897-911.
Nicholson et al., "NPI-2358 is a tubulin-depolymerizing agent: in-vitro evidence for activity as a tumor vascular-disrupting agent," Anticancer Drugs, Jan. 2006, vol. 17(1), pp. 25-31 (Abstract Only Provided).
Nicolson, "Metabolic syndrome and mitochondrial function: Molecular replacement and antioxidant supplements to prevent membrane peroxidation and restore mitochondrial function," Journal of Cellular Biochemistry, 2007, vol. 100, Iss. 6, pp. 1352-1369.
Nitecki et al., "A Simple Route to Sterically Pure Kiketopiperazines" J. Org. Chem., 1968, vol. 33(2), pp. 864-866.
Noggle et al., "Chapter 9: In vivo Differentiation of Human Embryonic Stem Cells," Human Embryonic Stem Cells: The Practical Handbook, Ed. Sullivan et al., 2007, John. Wiley & Sons, Ltd., pp. 124-147.
O'Connor et al., "Post-proline dipeptidyl-aminopeptidase from synaptosomal membranes of guinea-pig brain," European Journal of Biochemistry, 1986, vol. 154, Iss. 2, pp. 329-335.
Ostrovskaia et al., "Multicomponent antithrombotic effect of the neuroprotective prolyl dipeptide GVS-111 and its major metabolite cyclo-L-prolylglycine," Eksp Klin Farmakol, Mar.-Apr. 2002, vol. 65(2) (Abstract Only Provided).
Otani et al., "Bone marrow-derived stem cells target retinal astrocytes and can promote or inhibit retinal angiogenesis," Nature Medicine, 2002, vol. 8, No. 9, pp. 1004-1010.
Oztuna et al., "Intra-articular Injection of Tenoxicam in Osteoarthritic Knee Joints With Effusion," Orthopedics, 2007, vol. 30, Iss. 12, pp. 1039-1042.
Palace et al. "Epilepsy: an autoimmune disease?" Journal of Neurology, Neurosurgery & Psychiatry, Dec. 2000, vol. 69, No. 6, pp. 711-714.

(56) References Cited

OTHER PUBLICATIONS

Palacios et al., "Tenidap Decreases IL-8 and Monocyte Chemotactic Peptide-1 (MCP-1) mRNA Expression in the Synovial Tissue of Rabbits with Antigen Arthritis and in Cultured Synovial Cells," Clin. Exp. Immunol., 1998, vol. 111, pp. 588-596.

Pandey et al., "Synthetic Peptides Corresponding to a Repetitive Sequence of Malarial Histidine Rich Protein Bind Haem and Inhibit Haemozoin Formation in vitro," Mol Biochem Parasitol, 1997, vol. 90(1), pp. 281-287 (Abstract Only Provided).

Paris et al., "Equine embryos and embryonic stem cells: Defining reliable markers of pluripotency," Theriogenology, 2010, vol. 74, Iss. 4, pp. 516-524.

Parker et al., "Evidence for the Presence of Immunoreactive Histidyl-Proline Diketopiperazine [Cyclo (His-Pro)] in the Adult Human Brain," Peptides, Nov.-Dec. 1983, vol. 4(6), pp. 879-881 (Abstract Only Provided).

Parr et al., "Bone marrow-derived mesenchymal stromal cells for the repair of central nervous system injury," Bone Marrow Transplantation, 2007, vol. 40, Iss. 7, pp. 609-619.

Potgens et al., "Covalent dimerization of vascular permeability factor/vascular endothelial growth factor is essential for its biological activity. Evidence from Cys to Ser mutations," The Journal of Biological Chemistry, 1994, vol. 269, Iss. 52, pp. 32879-32885.

Pekary et al., "In vitro Production of a TRH-Homologous Peptide and His-Pro Diketopiperazine by Human Semen," J Androl, 1985, vol. 6(6), pp. 379-385 (Abstract Only Provided).

Potocka et al., "Pharmacokinetic characterization of the novel pulmonary delivery excipient fumaryl diketopiperazine," J. Diabetes Sci. Technol., Sep. 2010, vol. 4(5), pp. 1164-1173 (Abstract Only Provided).

Prakash et al., "Synthesis and Biological Activity of Novel Neuroprotective Diketopiperazines," Bioorganic & Medicinal Chemistry, Sep. 2002, vol. 10(9), pp. 3043-3048.

Prasad et al., "Distribution and Characterization of Cyclo (His-Pro)-Like Immunoreactivity in Human Cerebrospinal Fluid," Biochem Biophys Res Commun, 1986, vol. 136(2), pp. 835-842 (Abstract Only Provided).

Prasad et al., "Distribution and Metabolism of Cyclo (His-Pro): A New Member of the Neuropeptide Family," Peptides, May-Jun. 1982, vol. 3(3), pp. 591-598 (Abstract Only Provided).

Prasad et al., "Increased cerebrospinal fluid cyclo(His-Pro) content in schizophrenia," Neuropeptides, Nov. 1991, vol. 20(3), pp. 187-190.

Prasad et al., "Isolation of cyclo(His-Pro)-like immunoreactivity from Human Urine and Demonstration of its Immunologic, Pharmacologic, and Physico-chemical Identity with the Synthetic Peptide," Biochemistry Int, 1990, vol. 21(3), pp. 425-434 (Abstract Only Provided).

Prasad et al., "Thermoregulation in rats: opposing effects of thyrotropin releasing hormone and its metabolite histidyl-proline diketopiperazine," Biochem Biophys Res. Commun., 1978, vol. 85(4), pp. 1582-187.

Prasad, "Bioactive Cyclic Dipeptides," Peptides, 1995, vol. 16(1), pp. 151-164.

Purves et al. (Eds), Neuroscience, 2001, Sinauer Associates, Inc., 2nd Edition, pp. 75, 367, 400 and 403.

Purves et al., Life: the Science of Biology, 3rd Ed. (1992), p. 376.

Rainbow et al., "Distribution, survival and biological effects in mice of a behaviorally active, enzymatically stable peptide: pharmacokinetics of cyclo(Leu-Gly) and puromycin-induced amnesia," Pharmacol Biochem Behav, May 1979, vol. 10(5), pp. 787-793.

Rainger et al., "Endothelial-Borne Platelet-Activating Factor and Interleukin-8 Rapidly Immobilize Rolling Neutrophils," Am. J. Physiol., 272(Heart Circ. Physiol. 41):H114-H122 (1997).

Rainsford et al., "Effects of 5-Lipoxygenase Inhibitors on Interleukin Production by Human Synovial Tissues in Organ Culture: Comparison with Interleukin-1-Synthesis Inhibitors," J. Pharm. Pharmacol., 48:46-52 (1996).

Ramírez et al., "Platelet Activating Factor Modulates Microvascular Permeability through Nitric Oxide Synthesis," Microvascular Research, 1995, vol. 50, Iss. 2, pp. 223-234.

Reubsaet et al., "Qualitative and Quantitative Aspects of the Degradation of Several Tripeptides Derived from the Antitumor Peptide Antagonist [Arg(6), D-Trp(7,9), MePhe(8)] Substance P[6-11]," J Pharm Biomed Anal 1999, 19(3-4):2.

Rinaldi et al. "Immunological markers in multiple sclerosis: tackling the missing elements," Neurol. Sci., Dec. 2005, vol. 26 Suppl. 4, pp. S215-S217.

Rosenthal et al., "Effects of Arachidonic Acid and Cyclo (His-Pro) on Zinc Transport Across Small Intestine and Muscle Tissues," Life Sci, 2001, vol. 70(3), pp. 337-348 (Abstract Only Provided).

Roth et al., "Platelet-Activating Factor Exerts Mitogenic Activity and Stimulates Expression of Interleukin 6 and Interleukin 8 in Human Lung Fibroblasts via Binding to its Functional Receptor," J. Exp. Med., 1996, vol. 184, pp. 191-201.

Rother et al., "Challenges facing islet transplantation for the treatment of type 1 diabetes mellitus," The Journal of Clinical Investigation, 2004, vol. 114, No. 7, pp. 877-883.

Sakkas et al., "T Cells and T-Cell Cytokine Transcripts in the Synovial Membrane in Patients with Osteoarthritis", Clinical and Diagnostic Laboratory Immunology, Jul. 1998, vol. 5, No. 4, pp. 430-437.

Sakurada et al., "Antinociceptive activities of synthetic dipeptides in mice." J. Pharm. Pharmacol., 1982, vol. 34, pp. 750-751.

Sakuta et al., "Dual Regulatory Effects of Interferon-α, -β, and -γ on Interleukin-8 Gene Expression by Human Gingival Fibroblasts in Culture Upon Stimulation with Lipopolysaccharide from Prevotella Intermedia, Interleukin-1α, or Tumor Necrosis Factor-α," J. Dent Res., 1998, vol. 77(8), pp. 1597-1605.

Samanta et al., "Crystal Structure of Human Plasma Platelet-activating Factor Acetylhydrolase," J. Biol. Chem., vol. 283(46), Nov. 14, 2008, pp. 31617-31624.

Sammes, "Naturally Occurring 2,5-Dioxopiperazines and Related Compounds," Fortschr. Chem. Org. Naturst., 1975, vol. 32, pp. 51-118.

Sandstrom et al., "Serum-free media for cultures of primitive and mature hematopoietic cells," Biotechnology and Bioengineering, 1994, vol. 43, Iss. 8, pp. 706-733.

Sano et al. "Process Research and Development of L-Alanyl-L-Glutamine, a Component of Parenteral Nutrition," Organic Process Research & Development, 2000, vol. 4, pp. 147-152.

Sato et al., "Comparison of the antiociceptive effect between the cyclic dipeptide cyclo[Tyr(Et)-homoarginine] and the linear dipeptide Boc-Tyr(Et)-homoarginine-Ome in rats.," Jpn J Pharmacol, Jan. 1984, vol. 34(1) (Abstract Only Provided).

Sato et al., "Maintenance of pluripotency in human and mouse embryonic stem cells through activation of Wnt signaling by a pharmacological GSK-3-specific inhibitor," Nature Medicine, 2004, vol. 10, No. 1, pp. 55-63.

Scharpe et al., "Peptide Truncation by Dipeptidyl Peptidase IV: A New Pathway for Drug Discovery," Verh K. Acad Geneeskd Belg. 2001, vol. 63(1), pp. 5-32 (Abstract Only Provided).

Schlingemann et al., "Role of vascular permeability factor/vascular endothelial growth factor in eye disease," Brit. J. Ophthalmology, vol. 81, 1997, pp. 501-512.

Sepetov et al., "Rearrangement, Racemization and Decomposition of Peptides in Aqueous Solution," Peptide Research, 1991, vol. 4(5), pp. 308-313 (Abstract Only Provided).

Seredenin et al. "Endogenous dipeptide cycloprolylglycine shows selective anxiolytic activity in animals with manifest fear reaction," Bull Exp Biol Med; Apr. 2002; vol. 1333(4) (Abstract Only Provided).

Shaw et al., "Future of early detection of lung cancer: the role of mouse models." Clin Cancer Res., Jul. 1; 11(13 Pt 2): 4999s-5003s, 2005.

Shimazaki et al., "Diketopiperazine Derivatives, a New Series of Platelet-Activating Factor Inhibitors," Chem. Pharm. Bull., 1987, vol. 35(8), pp. 3527-3530.

Shimazaki et al., "Diketopiperazines as a New Class of Platelet-Activating Factor Inhibitors," J. Med. Chem., 1987, vol. 30, pp. 1706-1709.

Shimazaki et al., "PAF Inhibitory Activity of Diketopiperazines: Structure-Activity Relationships," Lipids, 1991, vol. 26(12), pp. 1175-1178.

(56) References Cited

OTHER PUBLICATIONS

Shimi et al., "Isolation of Cairomycins A and C," Antimicrobial Agents and Chemotherapy, Jun. 1981, vol. 19(6), pp. 941-944.
Shimonkevitz et al., "A Diketopiperazine Fragment of Human Serum Albumin Modulates T-Lymphocyte Cytokine Production Through Rap1," Journal of Trauma, Injury, Infection, and Critical Care, 2008, vol. 64, No. 1, pp. 35-41.
Shukla et al., "Role of Endogenous Cyclo(His-Pro) in Cold-Induced Hypothermia in the Desert Rat (*Mastomys natalensis*)," Peptides; 1994; 15(8):1471-4 (Abstract Only Provided).
Shutov et al., "[Diagnostic Significance of the type of In Vitro Interaction between Blood Lymphocytes and Serotonin in Multiple Sclerosis]," [Article in Russian], Zh Nevrol Psikhiatr Im S S Korsakova, 2002, vol. 102(4), pp. 35-38 (Abstract Only Provided).
Skates et al., "Molecular markers for early detection of renal carcinoma: investigative approach," Clin Cancer Res, Sep. 2004, vol. 10(18 Pt 2), pp. 6296S-6301S.
Slater, "Gas-liquid chromatography of 2,5-diketopiperazines as their trifluoroacetyl derivatives," Journal of Chromatography A, 1972, vol. 64, Iss. 1, pp. 166-169.
Smith et al., "Lesson 10, vol. 12—Asthma: Evolving Anti-Inflammatory Therapy," www.chestnet.org/education/pccu/vol12/ lesson10.html, pp. 1-8, printed Jul. 20, 2000.
Smith et al., "Recent developments in drug therapy for multiple sclerosis," Mult. Scler., 1999, vol. 5, pp. 110-120.
Smith et al., "Solid-phase synthesis of a library of piperazinediones and diazepinediones via Kaiser oxime resin." Bioorg. Med. Chem., 1998, vol. 8, pp. 2369-2374.
Lollid et al. "Is celiac disease an autoimmune disorder?" Current Opinion in Immunology, Dec. 2005, vol. 17, No. 6, pp. 595-600.
Sollis "Short and novel stereospecific synthesis of trisubstituted 2,5-diketopiperazines," J Org Chem, Jun. 2005, vol. 70(12), pp. 4735-4740 (Abstract Only Provided).
Song et al., "Body weight reduction in rats by oral treatment with zinc plus cyclo-(His-Pro)," Br. J. Pharmacol., Sep. 2009, vol. 158(2), pp. 442-450, Epub May 5, 2009 (Abstract Only Provided).
Song et al., "Raw vegetable food containing high cyclo (his-pro) improved insulin sensitivity and body weight control," Metabolism, Nov. 2005, vol. 54(11), pp. 1480-1489 (Abstract Only Provided).
Song et al., "Synergistic Antidiabetic Activities of Zinc, Cyclo (His-Pro), and Arachidonic Acid," Metabolism 2001 50(1):53-59 (Abstract Only Provided).
Stark et al., "Structures, sensory activity, and dose/response functions of 2,5-diketopiperazines in roasted cocoa nibs (*Theobroma cacao*)." J Agric Food Chem., Sep. 7, 2005, vol. 53(18), pp. 7222-7231 (Abstract Only Provided) PMID: 16131134.
Steiner et al., "Histidyl Proline Diketopiperazine (Cyclo [His-Pro]) in Eating Disorders," Neuropeptides, Oct. 1989, vol. 14(3), pp. 185-189 (Abstract Only Provided).
Strom et al., "Lactobacillus plantarum MiLAB 393 produces the antifungal cyclic dipeptides cyclo(L-Phe-L-Pro) and cyclo(L-Phe-trans-4-OH-L-Pro) and 3-phenyllactic acid.," Appl Environ Microbiol, Sep. 2002, vol. 68(9) (Abstract Only Provided).
Suguna et al., "Crystal structures of diketopiperazines containing α-aminoisobutyric acid: Cyclo(Aib-Aib) and cyclo(Aib-L-lle)," Biopolymers, 1982, vol. 21, Iss. 9, pp. 1847-1855.
Sun et al., "Rho and ROCK Signaling in VEGF-Induced Microvascular Endothelial Hyperpermeability," Microcirculation, 2006, vol. 13, Iss. 3, pp. 237-247.
Suzuki et al., "Effect of cyclic dipeptides containing histidine on pentobarbital narcosis," J. Pharm. Dyn., May 1981, vol. 4(5), pp. 377-379.
't Hart et al., "Evaluating the validity of animal models for research into therapies for immune-based disorders," DDT, 2004, vol. 9(12), pp. 517-524.
Takahara et al., "Detection in Human Serum by Radioimmunoassay of Histidyl-Proline Diketopiperazine, a Metabolite of Thyrotropin-Releasing Hormone," J Clinical Endocrinology, 1983, vol. 56(2), pp. 312-319 (Abstract Only Provided).
Tascioglu et al., "Efficacy of intra-articular sodium hyaluronate in the treatment of knee osteoarthritis," Clinical Rheumatology, 2003, vol. 22, Iss. 2, pp. 112-117.
Teitel et al., "Rheumatoid arthritis," PubMed Health, reviewed Feb. 2, 2012, available at www.ncbi.nlm.nih.gov/pubmedhealth/ PMH0001467/?report=printable, 8 pages.
Teitel et al., "Scleroderma," PubMed Health, reviewed Feb. 2, 2012, available at www.ncbi.nlm.nih.gov/pubmedhealth/PMH0001465/? report=printable, 7 pages.
Teitel et al., "Systemic lupus erythematosus," PubMed Health, reviewed Feb. 2, 2012, available at www.ncbi.nlm.nih.gov/ pubmedhealth/PMH0001471/?report=printable, 9 pages.
Unal et al., "Cyclo(Gly-Gln) inhibits the cardiorespiratory depression produced by beta-endorphin and morphine," Brain Research, 1997, vol. 747(1), pp. 52-59.
Vara et al., "PI3K/Akt signalling pathway and cancer," Cancer Treatment Reviews, 2004, vol. 30, pp. 193-204.
Varughese et al., "Crystal structure and conformation of cyclo-L-cystine," Int. J. Pept. Protein Res., vol. 18, Jul. 1981, pp. 88-102.
Vogel et al., "Disseminated tumor cells—Their detection and significance for prognosis of gastrointestinal and pancreatic carcinomas," Virchows Arch, 2001, vol. 439, pp. 109-117.
Walter et al., "Neurohypophyseal hormones, analogs, and fragments: their effect on puromycin-induced amnesia," Proc. Natl. Acad. Sci., Oct. 1975, vol. 72(10), pp. 4180-4184.
Walter et al., "The Cyclized C-Terminal Dipeptide of Arginine Vasopressin: Metabolic Stability and Antagonism of Puromycin-Induced Amnesia," Hormones and Behavior, 1982, vol. 16; p. 234-244.
Wang et al., "A facile pathway to synthesize diketopiperazine derivatives," Tetrahedron Lett, 2002, vol. 43, pp. 865-867.
Wang et al., "Novel inhibitors of plasminogen activator inhibitor-1: development of new templates from diketopiperazines," Bioorg Med Chem Lett, Sep. 2002, vol. 12(17), pp. 2367-2370 (Abstract Only Provided).
Watterson et al., "Viscosupplementation: Therapeutic Mechanisms and Clinical Potential in Osteoarthritis of the Knee," Journal of the American Academy of Orthopaedic Surgeons, 2000, vol. 8, No. 5, pp. 277-284. Abstract Only.
Weng et al., "Novel CCK-B receptor agonists: diketopiperazine analogues derived for CCK4 bioactive conformation," Regul Pept, Aug. 1996; vol. 65(1) (Abstract Only Provided).
Wennemers et al., "Diketopiperazine Receptors: A Novel Class of Highly Selective Receptors for Binding Small Peptides," Chem. Eur. J., 2001, vol. 7, No. 15, pp. 3342-3347.
Weszl et al., "Freeze-Dried Human Serum Albumin Improves the Adherence and Proliferation of Mesenchymal Stem Cells on Mineralized Human Bone Allografts," Journal of Orthopaedic Research, 2012, vol. 30, Iss. 3, pp. 489-496.
Wilber et al., "Endogenous histidyl-proline diketopiperazine [cyclo (His-Pro)]: a potential satiety neuropeptide in normal and genetically obese rodents," Trans Assoc Am Physicians, 1983, vol. 96, pp. 131-136.
Wilber et al., "Histidyl-proline diketopiperazine: a potent and chronic appetite-inhibiting neuropeptide," Trans Assoc. Am Physicians, 1986, vol. 99, pp. 245-249.
Wilkes et al. "Patient Survival after Human Albumin Administration: A Meta-Analysis of Randomized, Controlled Trials." Annals of Internal Medicine, Aug. 2001, vol. 135, No. 3, pp. 149-164.
Wisniewski et al., "Relationship between serum cyclo (His-Pro) concentrations and the nutritional status of HIV-infected patients," South Med. J., Mar. 1994, vol. 87(3), pp. 348-351 (Abstract Only Provided).
Woehlecke et al., "Reversal of breast cancer resistance protein-mediated drug resistance by tryprostatin A.," Int J Cancer; Dec. 2003, vol. 107(5) (Abstract Only Provided).
Wolf et al., "Identification of Cyclo(His-Pro)-Like Immunoreactivity in Human Follicular Fluid: Correlation with Steroid and Peptide Hormones," J Soc Gynecol Investigation, 1994, vol. 1(3), pp. 220-224 (Abstract Only Provided).
Wretlind, "The Availability of the Isopropyl Ester of L- and D-Phenylalanine and 3,6-Dibenzyl-2,5-Diketopiperazine form Growth in Rats," Acta phys. Scandinav, May 1953, vol. 30, pp. 97-104.

(56) References Cited

OTHER PUBLICATIONS

Wu et al., "Embryonic stem cell transplantation: potential applicability in cell replacement therapy and regenerative medicine," Frontiers in Bioscience, 2007, vol. 12, Iss. 12, pp. 4525-4535.
Wyatt et al., "2,5-Diketopiperazines as potent and selective oxytocin antagonists 1: Identification, stereochemistry and initial SAR," Bioorg Med Chem Lett., May 16, 2005, vol. 15(10), pp. 2579-2582 (Abstract Only Provided) PMID: 15863320.
Yamada et al., "Abundance of Cyclo (His-Pro)-like Immunoreactivity in the Brain of TRH-Deficient Mice," Endocrinology, Jan. 1999, vol. 140(1), pp. 538-541 (Abstract Only Provided).
Yanagisawa et al., "The Subcellular and Organ Distribution and Natural Form of Histidyl-Proline Diketopiperazine in Rat Brain Determined by a Specific Radioimmunoassay," J Biol Chem, Nov. 10, 1980, vol. 255(21), pp. 10290-10294 (Abstract Only Provided).
Yang et al., "Increased hepatic platelet activating factor (PAF) and PAF receptors in carbon tetrachloride induced liver cirrhosis." Gut, Jan. 2004, vol. 53, No. 6, pp. 877-883.
Yasukawa, "Inflammation in age-related macular degeneration: pathological or physiological?", Expert Review of Ophthalmology, 2009, vol. 4, Iss. 2, pp. 107-112.
Yi Es, "Hypersensitivity pneumonitis," Crit Rev Clin Lab Sci., Nov. 2002, vol. 39(6), pp. 581-629.
Yoshida et al., "PAF Inhibitors of Microbial Origin," Prog. Biochem. Pharmacol., 1988, vol. 22, pp. 68-80.
Youngblood et al., "Bovine Serum Albumin-GABA-His-Pro-NH2: an Immunogen for Production of Higher Affinity Antisera for TRH," J Neursci Methods, 1983, vol. 9(4), pp. 367-373 (Abstract Only Provided).
Zander et al., "Allogeneic bone marrow transplantation for acute leukemia refractory to induction chemotherapy," Cancer, 1985, vol. 56, Iss. 6, pp. 1374-1379.
Zeng et al., "Synthesis of a small library of diketopiperazines as potential inhibitors of calpain," Bioorg Med Chem Lett, Jun. 2005, vol. 15(12), pp. 3034-3038.
Zieve, "Multiple sclerosis," PubMed Health, reviewed Sep. 26, 2011, available at www.ncbi.nlm.nih.gov/pubmedhealth/PMH0001747/?report=printable, 10 pages.
Ziong et al., "Chemical Constituents from Phytolacca polyandra" Yunnan Zhiwu Yanjiu, 2002, vol. 24, No. 3, pp. 401-405. (English abstract).
Zulewski et al., "Multipotential Nestin-Positive Stem Cells Isolated From Adult Pancreatic Islets Differentiate Ex Vivo Into Pancreatic Endocrine, Exocrine, and Hepatic Phenotypes," Diabetes, 2001, vol. 50, No. 3, pp. 521-533.
International Search Report and Written Opinion for International (PCT) Patent Application No. PCT/US14/30538 dated Oct. 30, 2014, 12 pages.
International Preliminary Report on Patentability for International (PCT) Patent Application No. PCT/US14/30538 dated Sep. 24, 2015, 9 pages.
Official Action (English translation) for Chinese Patent Application No. 201480015832.9 dated Dec. 1, 2016, 8 pages.
Official Action (English translation) for Chinese Patent Application No. 201480015832.9 dated Jul. 31, 2017, 8 pages.
Extended European Search Report for European Patent Application No. 14763038.8 dated Jul. 28, 2016, 7 pages.
Official Action (with English translation) for Japanese Patent Application No. 2016-503416 dated Aug. 29, 2017, 5 pages.
Official Action for U.S. Appl. No. 14/216,430 dated Jul. 24, 2015, 6 pages.
Official Action for U.S. Appl. No. 14/216,430 dated Feb. 2, 2016, 21 pages.
Official Action for U.S. Appl. No. 14/216,430 dated Nov. 2, 2016, 13 pages.
Notice of Allowance for U.S. Appl. No. 14/216,430 dated Aug. 2, 2017, 9 pages.
Official Action (with English translation) for Japanese Patent Application No. 2016-503416 dated Apr. 2, 2019 [received Apr. 3, 2019], 5 pages.
Davatchi et al., "Mesenchymal stem cell therapy for knee osteoarthritis. Preliminary report of four patients," International Journal of Rheumatic Diseases, 2011, vol. 14, Iss. 2, pp. 211-215.
Official Action for Australian Patent Application No. 2014232728 dated Feb. 4, 2019, 5 pages.
Notice of Acceptance for Australian Patent Application No. 2014232728 dated Feb. 12, 2019, 4 pages.
Official Action (English translation) for Chinese Patent Application No. 201480015832.9 dated Nov. 26, 2018, 8 pages.
Official Action for European Patent Application No. 14763038.8 dated Oct. 1, 2018, 5 pages.
Notice of Allowance (with English translation) for Chinese Patent Application No. 201480015832.9 dated Dec. 4, 2020, 5 pages.
Ryser et al, "Serum albumin strongly influences SDF-1 dependent migration", International Journal of Hematology, 2009, vol. 89, Iss. 3, pp. 269-275.
Official Action for Canadian Patent Application No. 2,906,864 dated Feb. 18, 2020, 4 pages.
Official Action (English translation) for Chinese Patent Application No. 201480015832.9 dated Aug. 5, 2019, 5 pages.
Official Action (English translation) for Chinese Patent Application No. 201480015832.9 dated Jan. 16, 2020, 5 pages.
Notice of Intention to Grant for European Patent Application No. 14763038.8 dated Dec. 20, 2019, 7 pages.
Official Action for Indian Patent Application No. 8903/DELNP/2015 dated Nov. 29, 2019, 6 pages.
Notice of Allowance (with English translation) for Japanese Patent Application No. 2016-503416 dated Aug. 20, 2019, 2 pages.
Official Action for New Zealand Patent Application No. 712630 dated Jul. 6, 2020, 6 pages.
Official Action for Canadian Patent Application No. 2,906,864 dated Feb. 4, 2021, 4 pages.
Official Action for New Zealand Patent Application No. 712630 dated Mar. 5, 2021, 4 pages.

\* cited by examiner

Saline Control

1µM Dexamethasone

50 µM DADKP

Ampion

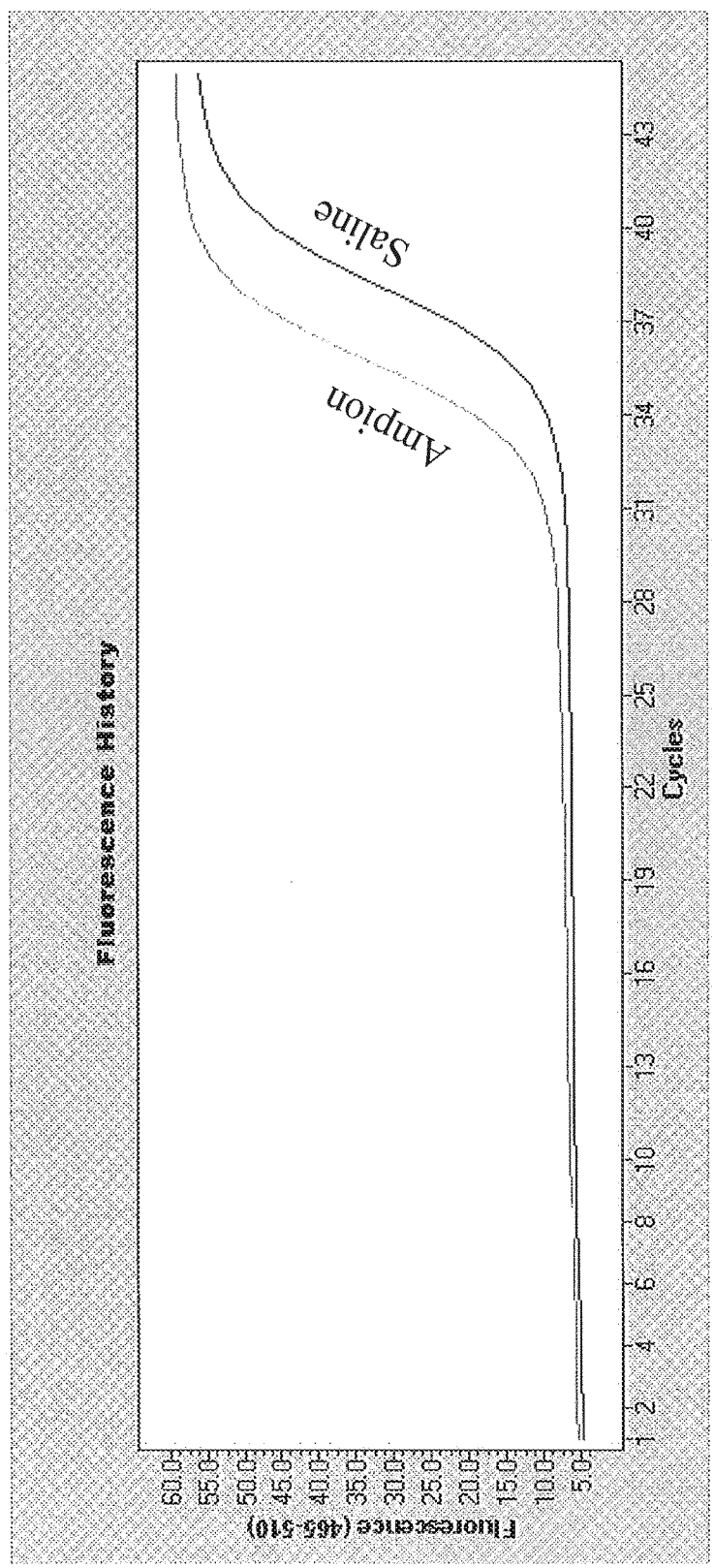

COMPOSITIONS FOR THE MOBILIZATION, HOMING, EXPANSION AND DIFFERENTIATION OF STEM CELLS AND METHODS OF USING THE SAME

CROSS REFERENCE TO RELATED APPLICATION

This application is a continuation of U.S. patent application Ser. No. 14/216,430, filed Mar. 17, 2014, now U.S. Pat. No. 9,808,454, issued on Nov. 7, 2017; which claims the benefit of priority under 35 U.S.C. § 119(e) to U.S. Provisional Patent Application Ser. No. 61/791,623, filed Mar. 15, 2013; U.S. Provisional Patent Application Ser. No. 61/832,713, filed Jun. 7, 2013; and U.S. Provisional Patent Application Ser. No. 61/897,449, filed Oct. 30, 2013; the disclosure of each of which is incorporated herein by reference. This application also claims the benefit of priority under 35 U.S.C. § 119(e) to U.S. Provisional Patent Application Ser. No. 61/923,314, filed Jan. 3, 2014; and U.S. Provisional Patent Application Ser. No. 61/939,625, filed Feb. 13, 2014.

TECHNICAL FIELD

This invention relates to the field of stem cell technology. More particularly, the invention describes compositions for the mobilization, homing, expansion and/or differentiation of stem cells and methods of using the same.

BACKGROUND

Stem cells have the ability to divide for indefinite periods in culture and to become a wide variety of specialized cell and tissue types, which can then be used for basic research, drug discovery, and treatment (or prevention) of many diseases. Stem cells are typically divided into two main groups: adult stem cells and embryonic stem cells.

Adult stem cells are undifferentiated but are present in differentiated tissues, and are capable of differentiation into the cell types from which tissue the adult stem cell originated. Adult stem cells have been derived from various sources, such as the nervous system, bone marrow; adipose tissue, dermis, pancreas and liver. Stem cells have also been isolated from umbilical cord and placenta. It is believed that stem cells of the adult type are also found in smooth muscle tissue, striated muscle tissue, cardiac muscle tissue, bone tissue, bone spongy tissue, cartilage tissue, pancreatic ductal tissue, spleen tissue, thymus tissue, tonsil tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue (including retinal tissue), lung tissue, testicular tissue, ovarian tissue, prostate tissue, connective tissue, endocrine tissue, and mesentery tissue.

Embryonic stem cells are undifferentiated cells derived from the embryo. Typically, these cells are extracted from the inner cell mass of a blastocyte and when cultured under the unique conditions, either alone or in combination with a variety of feeder cells, the embryonic stem cells maintain euploid karyotype, do not undergo senescence, and retain the ability to differentiate into cells of the endodermal, ectodermal, and mesodermal lineages.

Mesenchymal stem cells (MSCs) refer to cells that have the potential to self-renew and are capable of differentiating into multiple mesenchymal lineages. These cells may have the capacity to give rise to other germ layer cell types such as neuronal cells. The major source of MSCs is isolation from bone marrow and other tissues, such as adipose tissue. Due to their scarcity in adult tissues, MSCs are normally isolated only in small numbers, however, they have an extensive capacity for proliferation and can be readily expanded in culture to generate clinically-relevant numbers of cells through multiple passages. These cells have been shown to support tissue repair and regeneration, making them a promising tool for various therapeutic applications.

One of the earliest clinical uses of stem cells was for performing bone marrow transplants in patients with hematological malignancies in which hematopoietic stem cells derived from the donor bone marrow were administered into the recipient subsequent to treating the recipient with a dose of radiation and/or chemotherapy in order to ablate not only the hematological malignancy but also non-malignant hematopoiesis. The administration of non-malignant hematopoietic stem cells results in donor-specific hematopoiesis, and in some patients, cure of the malignancy. This was first described in 1957 in patients with acute leukemia following myeloablation. Stem cells have also been utilized as an autologous bone marrow transplant in patients administered high doses of chemotherapy and/or radiation therapy for the treatment of solid tumors, in order to restore bone marrow. The use of autologous hematopoietic cell transplants combined with high dose chemo/radiotherapy for solid tumors has been extensively investigated for breast, colon, lung, nasopharyngeal cancer, and other types of cancers.

The clinical use of autologous stem cells has also been performed for a variety of autoimmune indications, including rheumatoid arthritis, multiple sclerosis, systemic lupus erythromatosis, and systemic sclerosis.

The importance of technologies utilized to expand stem cells, both of adult and/or embryonic derivation is illustrated by the clinical uses of these cells in treatment of a wide range of diseases. The cell culture systems used in these treatments (e.g., liquid static culture, semi-solid culture and long term bone marrow culture) appears to have their own unique requirements which must be met before one can culture stem cells of human or other mammalian species. To date, however, a common requirement and disadvantage of stem cell culture systems has been the requirement for undefined components contained in animal sera (e.g., fetal bovine serum or horse serum) for optimal growth or expansion of stem cells.

The use of serum in the culture of hematopoietic cells is disadvantageous for several reasons. Serum is a major source of undefined differentiation factors and thus tends to promote hematopoietic cell differentiation, rather than expansion. The efficiency of serum varies between lots of serum. Some lots of serum have been found to be toxic to cells. Moreover, serum may be contaminated with infectious agents such as mycoplasma, bacteriophage, and viruses. These problems cause inconsistencies in the growth-supporting properties of the medium, making standardization of stem cell production processes difficult and making the interpretation of experiments carried out in serum-containing media difficult. Thus, the use of serum represents a major obstacle for the clinical implementation of stem cell-related therapies.

As a result, researchers have attempted to replace animal sera or conditioned media with serum-free culture media of varying degrees of chemical definition. These attempts have met with varying degrees of success, depending upon the identity of the cell type one is trying to expand. The development of serum-free media has been reviewed (Sandstrom, E. E. et al., Biotech. & Bioengin. 43:706-733 (1994); Collins, P. C. et al., Curr. Opin. Biotech. 7:223-230 (1996); McAdams, T. A. et al., TIBTECH 14:341-349 (1996)). A more attractive alternative would be a defined serum-free medium. Therefore, it is desirable to develop defined serum-free media and methods for (i) isolating stem cells and (ii) expanding these cells for an extended period of time through multiple passages while maintaining their multi-lineage differentiation potential. The creation of defined serum-free media and methods should provide a robust platform that will help to enable the clinical implementation of stem cell-based therapies.

SUMMARY OF INVENTION

One embodiment of the present invention is a method to cause an effect selected from the group consisting of stem cell mobilization, stem cell homing, stem cell expansion, and stem cell differentiation in a subject. The method includes administering DA-DKP to a subject in need thereof. In this embodiment and in all other embodiments described herein, the DA-DKP can be administered in various formulations, can be administered by various routes of administration and be produced by various methods. For example, the DA-DKP can be administered as a pharmaceutical composition that includes DA-DKP. Such pharmaceutical compositions can also include N-acetyl tryptophan, caprylate and/or caprylic acid. Such pharmaceutical compositions can include a fraction of human serum albumin, wherein substantially all of the albumin has been removed from the fraction or can include a low molecular weight fraction of human serum albumin, such as a less than 5000 molecular weight fraction. Such fractions of human serum albumin can be produced by filtration. Also, the pharmaceutical composition can be prepared by heating human serum albumin under conditions effective to cause the formation of DA-DKP or by a process including contacting human serum albumin with an enzyme that cleaves the two N-terminal amino acids of human albumin under conditions effective to produce DA-DKP. The DA-DKP can be a synthetic DA-DKP.

In all embodiments of the present invention, the DA-DKP can be administered locally to the subject. For example, the site of local administration can be selected from a joint, a surgical site, a site of a segmented skeletal gap or non-union fracture, a wound, an ulcer, and an inflammatory skin rash. Also, the DA-DKP can be administered as a parenteral formulation, can be administered systemically to the subject or can be administered as an oral dosage formulation. Further, the DA-DKP can be formulated as part of, or on an implantable device, such as one selected from a sponge, biocompatible polymer, bioerodible polymer, putty, gel, bone matrix, artificial bone matrix, bolt, screw, endotracheal tube, stent, contact lense, pacemaker, central IV tube, foley catheter, and intracranial device.

In all embodiments of the present invention, administration of DA-DKP can increase production of CXCR4, decrease production of CXCL12, increase production of MMP14 or MMP13, increase production of aggrecan, increase production of SDF1, increase production of collagen 2A1 or any combination of the foregoing. Also, administration of DA-DKP can decrease production of a protein selected from the group consisting of MAPK-activated protein kinase 3, beta-adrenergic receptor kinase 1, ADAM metallopeptidase with thrombodpondin type I motif, MAPK-activated protein kinase 2, C-Src kinase, Macrophage Scavenger Receptor, Noggin, Tyrosine kinase Bruton, Glycogen synthase kinase-3 alpha/beta, Glycogen synthase kinase-3 alpha/beta, HSP 90 alpha/beta, HSP 90 alpha/beta, Phosphoinositide-3-kinase, catalytic subunit alpha, and Eukaryotic translation initiation factor 4A, Fibroblast Growth Factor 17 and combinations thereof. Further, administration of DA-DKP can decrease production of a protein selected from MAPK-activated protein kinase 3, Noggin, Phosphoinositide-3-kinase, catalytic subunit alpha, and combinations thereof. Administration of DA-DKP can also increase production of a protein selected from Clusterin (Apolipoprotein J), Prothrombin, C1QBP (Hyaluronan binding protein 1), TNFSF 15 (VEGF inhibitor), Mammaglobin 2, MIP3b (CCL 19), MCP 1 (CCL 2), PTHrP, Spondin 1, Elafin (elastase inhibitor), IL 11, NPS-PLA2, CFC 1 (cryptic protein), Testican 1 (SPOCK 1), Angiogenin, URB, MMP-3, IP10 (cxcl 10), BSSP 4, IL 8 (cxcl 8), RSPO2, Cystatin C, bFGF, Factor H, Coagulation Factor IX, SDF-1 (cxcl 12), CATC (Dipeptidyl peptidase 1), PIGR, Ck-b-8-1 (MPIF 1 splice variant), Cls, EMR2, ART, DPP 2, SAA, TIMP-1, Semaphorin 3A, and combinations thereof. Administration of DA-DKP can also increase production of a protein selected from Clusterin (Apolipoprotein J), C1QBP (Hyaluronan binding protein 1), MCP 1 (CCL 2), PTHrP, Elafin (elastase inhibitor), IL 11, MMP-3, bFGF, SAA, TIMP-1, Semaphorin 3A, and combinations thereof. Administration of DA-DKP can also decrease production of a protein selected from MAPK-activated protein kinase 3, Noggin, Phosphoinositide-3-kinase, catalytic subunit alpha, and combinations thereof and increase production of a protein selected from the group consisting of Clusterin (Apolipoprotein J), C1QBP (Hyaluronan binding protein 1), MCP 1 (CCL 2), PTHrP, Elafin (elastase inhibitor), IL 11, MMP-3, bFGF, SAA, TIMP-1, Semaphorin 3A, and combinations thereof. Further, administration of DA-DKP can down regulates Akt pathways in the subject.

Another embodiment of the present invention is a method of stimulating chondrogenesis in a subject by administering a pharmaceutical composition that includes DA-DKP and optionally, a component selected from N-acetyl tryptophan, caprylate, caprylic acid, and combinations thereof to a subject in need thereof. In this embodiment, chondrogenesis can be stimulated in a stem cell, such as a stem cell selected from a progenitor cell and mesenchymal stem call (MSC). In this embodiment, the stimulation of chondrogenesis can promote cartilage, bone, and/or ligament repair or induce repair or regeneration of chondral tissue, in the subject. Further, the chondrogenesis can treat or ameliorate a chondrogenic disease in the subject, and the chondrogenic disease can be a congenital cartilage disease, degenerative or fibrotic joint, rheumatoid arthritis or osteoarthritis. In this embodiment, the chondrogenesis can treat or repair a condition selected from a cartilage defect, a skeletal defect, or a fracture arising from trauma or surgery. Also, the DA-DKP administration can stimulate the formation of new bone or cartilage tissue.

In the method of stimulating chondrogenesis, the administration can include stimulating stem cells ex vivo and then administering the stimulated stem cells to the subject. For example, the stem cells can be stimulated ex vivo by culturing a population of stem cells of chondrocyte lineage with DA-DKP, or composition comprising a DA-DKP, for a time sufficient to stimulate chondrogenesis, and the step of administering includes implanting the stimulated cells into a desired site in the subject. In this embodiment, the chondrogenesis can result in increased production of collagen, type 2A1 collagen, type 1A1 collagen, or a 2-fold, 4-fold, 10-fold, 20-fold, or 25-fold increase in the production of collagen.

Further embodiments of the present invention include use of DA-DKP or a composition including DA-DKP in the preparation of a medicament for the stimulation of chondrogenesis in a mammal, and use of DA-DKP or a composition including DA-DKP for the stimulation of chondrogenesis in a mammal.

Another embodiment of the invention is a method of stimulating development of nervous tissue in a subject by administering a pharmaceutical composition that includes DA-DKP and optionally, a component selected from N-acetyl tryptophan, caprylate, caprylic acid, and combinations thereof to a subject in need thereof. In this embodiment, the development of nervous tissue can be stimulated in a stem cell, such as aprogenitor cell or mesenchymal stem call (MSC). The stimulation of development of nervous tissue can promote brain, spinal cord, and/or peripheral nerve repair or induce repair or regeneration of neurons, neuroglia, and/or astrocytes in the subject. The development of nervous tissue can treat or ameliorate a disease of the central nervous system and/or a disease of the peripheral nervous system in the subject, such as a neurodegenerative disease. Also, the development of nervous tissue can treat or repair a condition selected from an injury arising from trauma or surgery.

In the method of stimulating development of nervous tissue, the administration can include stimulating stem cells ex vivo and then administering the stimulated stem cells to the subject. For example, the stem cells can be stimulated ex vivo by culturing a population of stem cells of neuron, neuroglia, and/or astrocyte lineage with DA-DKP, or composition that includes DA-DKP, for a time sufficient to stimulate development of nervous tissue, and the step of administering includes implanting the stimulated cells into a desired site in the subject.

Further embodiments of the present invention include the use of DA-DKP or a composition that includes DA-DKP in the preparation of a medicament for the stimulation of development of nervous tissue in a subject, and use of DA-DKP or a composition that includes DA-DKP for the stimulation of development of nervous tissue in a subject.

A further embodiment of the invention is a method of stimulating development of tissue in a subject by administering DA-DKP to a subject in need thereof. In this embodiment, the tissue can be selected from nervous system tissue, adipose tissue, liver tissue, smooth muscle tissue, striated muscle tissue, cardiac muscle tissue, bone tissue, bone spongy tissue, cartilage tissue, pancreatic ductal tissue, spleen tissue, thymus tissue, tonsil tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue.

Further embodiments of the invention are a serum-free, eukaryotic cell culture media supplement that includes DA-DKP, wherein a cell culture medium supplemented with said supplement is capable of supporting the expansion of stem cells, and a composition that includes stem cells in a serum-free media supplemented with the media supplement.

Another embodiment of the invention is a method of expanding stem cells, that includes contacting the stem cells with DA-DKP, and culturing the stem cells under conditions suitable to facilitate the expansion of the stem cells.

A further embodiment of the invention is method of providing stem cells to a mammal, by contacting stem cells with DA-DKP, cultivating the stem cells under conditions suitable to facilitate the expansion of the cells; and introducing the expanded cells into a subject.

A still further embodiment of the invention is a method of causing stem cells to differentiate into a particular type of cell by contacting stem cells with DA-DKP, cultivating the stem cells under conditions suitable to facilitate the expansion of the stem cells, and adding one or more differentiation factors or changing culturing conditions to induce differentiation of the stem cells to form a different type of cell.

Another embodiment of the invention is a method of providing differentiated stem cells, to a subject. The method includes contacting stem cells with DA-DKP, cultivating the stem cells under conditions suitable to facilitate the expansion of the stem cells, and adding one or more differentiation factors or changing culturing conditions to induce differentiation of cells to form a different type of cell. The method further includes introducing the differentiated cells into the subject.

This Summary of Invention is neither intended nor should it be construed as being representative of the full extent and scope of the present invention. Moreover, references made herein to "the present invention," or aspects thereof, should be understood to mean certain embodiments of the present invention and should not necessarily be construed as limiting all embodiments to a particular description. The present invention is set forth in various levels of detail in the Summary of Invention as well as in the attached drawings and the Detailed Description and no limitation as to the scope of the present invention is intended by either the inclusion or non-inclusion of elements, components, etc. in this Summary of Invention. Additional aspects of the present invention will become more readily apparent from the Detailed Description, particularly when taken together with the drawings.

BRIEF DESCRIPTION OF DRAWINGS

FIG. 4 illustrates the increase in production of CXCR4 by mesenchymal stem cells grown in 3D culture by Ampion™ compared to saline.

DETAILED DESCRIPTION

Figure 1:
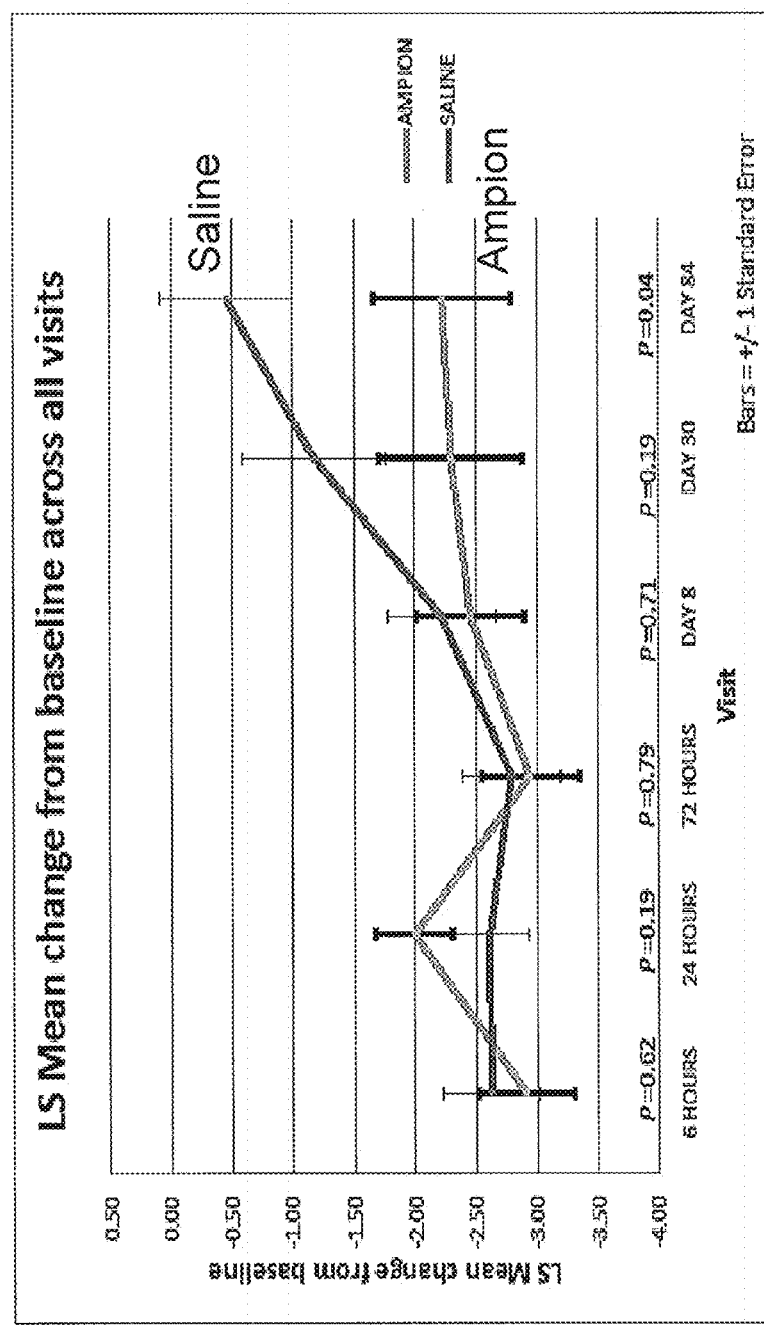
FIG. 1 illustrates the mean change in pain scores for osteoarthritis patients receiving Ampion™ compared to patients receiving saline.
Figure 2A:
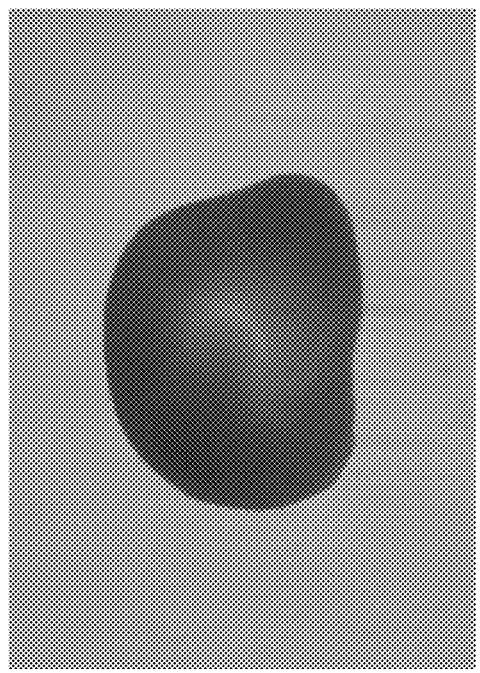
FIGS. 2A, 2B, 2C and 2D are photographs of cell aggregates from stem cells treated with saline (FIG. 2A), dexamethasone (FIG. 2B), DA-DKP (FIG. 2C) and Ampion™ (FIG. 2D).
Figure 2B:
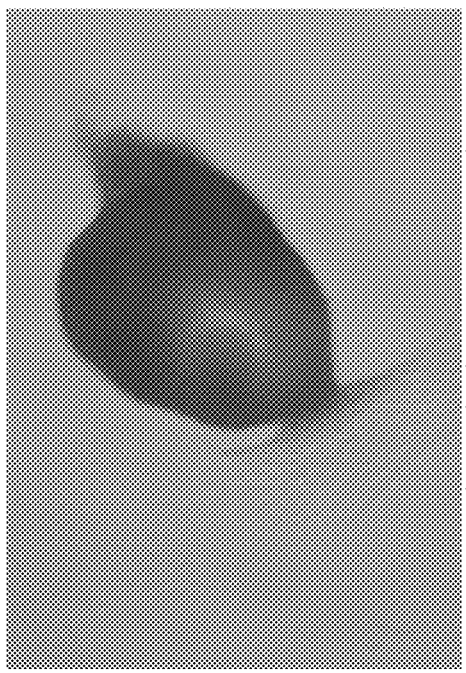
Figure 2C:
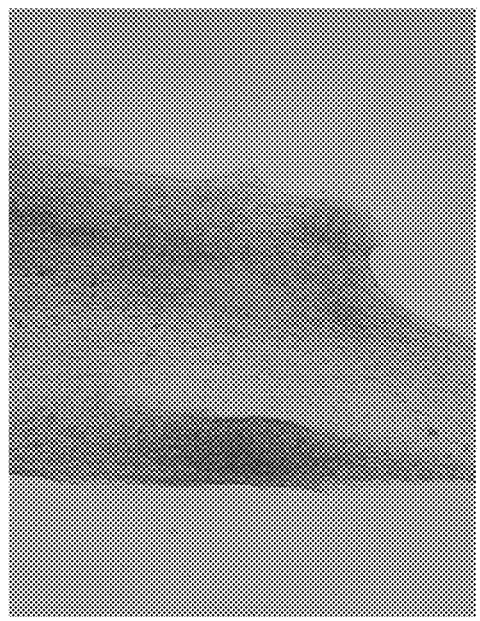
Figure 2D:
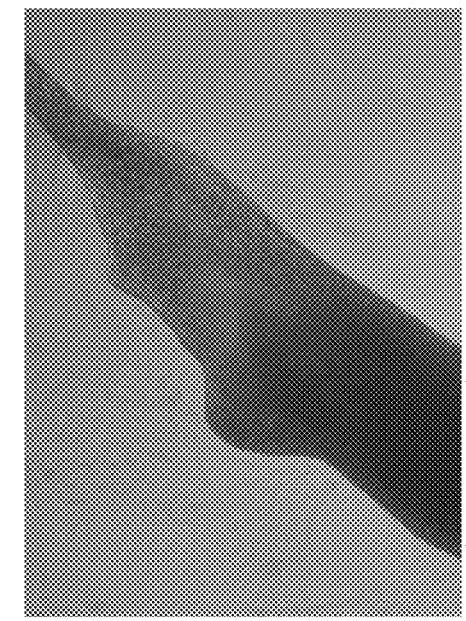

The present invention is drawn to methods for causing stem cell mobilization, homing, and/or differentiation in a subject in need thereof. The present invention is further directed to compositions that safely and effectively promote expansion of stem cells and methods of using such compositions and expanded cells in the treatment of disease states amenable to treatment with stem cells.

Definitions

The term "albumin substitute" refers to any compound which may be used in place of human serum albumin in the compositions of the invention to give substantially similar or better results as human serum albumin. Preferably, the albumin is of human origin. Most preferably, the albumin is human serum albumin.

The term "expand" or "expansion" refers to the growth and division, and not the differentiation, of stem cells in culture. The term "differentiation" refers to the development of a cell of a particular type into a cell of another type. The development of a pluripotent hematopoietic stem cell into a myeloid precursor is an example of differentiation. Likewise, the development of precursor cell into another type of cell is an example of differentiation.

The term "stem cell" generally refers to any cells that have the ability to divide for indefinite periods of time and to give rise to specialized cells. Within the definition of "stem cell" is included the following: a) totipotent cells such as an embryonic stem cell, an extra-embryonic stem cell, a cloned stem cell, a parthenogenesis derived cell, a cell reprogrammed to possess totipotent properties, or a primordial germ cell; b) pluripotent cell such as a hematopoietic stem cell, an adipose derived stem cell, a mesenchymal stem cell, a cord blood stem cell, a placentally derived stem cell, an exfoliated tooth derived stem cells, a hair follicle stem cell or a neural stem cell; and c) a tissue specific progenitor cell such as a precursor cell for the neuronal, hepatic, nephrogenic, adipogenic, osteoblastic, osteoclastic, alveolar, cardiac, intestinal, or endothelial lineage. The cells can be derived, for example, from tissues such as pancreatic tissue, liver tissue, smooth muscle tissue, striated muscle tissue, cardiac muscle tissue, bone tissue, bone marrow tissue, bone spongy tissue, cartilage tissue, liver tissue, pancreas tissue, pancreatic ductal tissue, spleen tissue, thymus tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue (including retinal tissue), lung tissue, testicular tissue, ovarian tissue, prostate tissue, connective tissue, endocrine tissue, and mesentery tissue. Specific stem cells are described below in the section entitled Ex Vivo Treatment Methods.

The term "totipotent cells" refers to mammalian cells that have the potential to become any cell type in the adult body and any cell type of the extraembryonic membranes (e.g., placenta). Totipotent cells are the fertilized egg and approximately the first 4 cells produced by its cleavage.

The term "pluripotent stem cells" refers to true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, EC cells are usually aneuploid.

The term "multipotent stem cells" refers to true stem cells that can only differentiate into a limited number of types. For example, the bone marrow contains multipotent stem cells that give rise to all the cells of the blood but may not be able to differentiate into other cells types.

The term "mesenchymal stem cells" refers to multipotent stromal cells that can differentiate into a variety of cell types, including osteoblasts, chondrocytes, and adipocytes (fat cells).

The term "hematopoietic stem cell" or "HSC" refers to a stem cell that is capable of differentiating into both myeloid lineages (i.e. monocytes, macrophages, neutrophils, basophils, eosinophils, erythrocytes, megakaryocytes/platelets and some dendritic cells) and lymphoid lineages (i.e. T-cells, B-cells, NK-cells, and some dendritic cells).

The term "ingredient" refers to any compound, whether of chemical or biological origin, that can be used in cell culture media to maintain or promote the growth or proliferation of cells. The terms "component," "nutrient" and "ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain growth of cells ex vivo can be selected by those of skill in the art, in accordance with the particular need.

By "cell culture" is meant cells or tissues that are maintained, cultured or grown in an artificial, in vitro environment.

The term "culture vessel" refers to glass containers, plastic containers, or other containers of various sizes that can provide an aseptic environment for growing cells. For example, flasks, single or multiwell plates, single or multiwell dishes, or multiwell microplates can be used. Further, a bioreactor can be used to culture cells.

The terms "cell culture medium," "culture medium" and "medium formulation" refer to a nutritive solution for culturing or growing cells.

The term "contacting" refers to the mixing, adding, seeding, or stirring of one or more cells with one or more compounds, solutions, media, etc.

A "serum-free" medium is a medium that contains no complete serum (e.g., human serum, fetal bovine serum, horse serum, goat serum, etc.).

The term "buffering agent" refers to an agent which acts to stabilize the hydrogen ion concentration and therefore the pH of a solution by neutralizing, within limits, both acids and bases. Suitable buffering agents which can be used in the supplement and the medium of the present invention include N-[2-hydroxyethyl]piperazine-N'-[2-ethanesulfonic acid] (HEPES), β-glycerol-phosphate, and bicarbonate buffer.

The term "subject" refers to any animal, including mammals, birds, reptiles and amphibians and in preferred embodiments to mammals, including humans, companion animals, food production animals and wild animals.

Compositions

The present invention provides compositions that are useful in methods of the present invention, such methods including in vivo methods for causing stem cell mobilization, homing and/or differentiation in a subject by administration of such compositions and ex vivo methods of expanding stem cells, providing stem cells to a subject, causing stem cells to differentiate, Thus, such compositions are useful in administration to a subject and indirect contact with stem cells or as an additive or supplement to cell culture medium. The compositions of the present invention are particularly suited for supporting the expansion of mesenchymal stem cells (MSCs). Such cells include but are not limited to, chondrocytes, osteoclasts, osteoblasts, and epithelial cells of skin and vascular tissue. The compositions of the present invention is also suited for supporting the expansion of both primary and immortalized cells of most or all embryonic origin (e.g., ectodermal derivatives, mesodermal derivatives, and endodermal derivatives). These cells include cells of the central and peripheral nervous system (neurons, glial cells, and astrocytes), epithelial cells (sensory epithelial cells, epidermal cells (skin, mammary, hair, nails, pituitary gland, sebaceous gland)), connective tissue cells (cartilage, bone, striated and smooth muscle, hematopoietic cells, lymphoid cells, kidney, gonadal cells, adrenal cells) and parenchymal cells of the liver, pancreas, thyroid, thymus, as well as epithelial linings of the urinary bladder, urethra, tympanic cavity, and eustachian tube. These cells can be of human or other mammalian or eukaryotic origin.

Compositions of the invention include. aspartyl-alanyl diketopiperazine (i. e., "Asp-Ala DKP or "DA-DKP"). Diketopiperazines (DKP) are a class of cyclic organic compounds that result from peptide bonds between two amino acids to form a lactam. They are the smallest possible cyclic peptides. The invention also provides for a pharmaceutical product comprising a DA-DKP composition.

Methods of making diketopiperazines, such as DA-DKP, are well known in the art, and these methods may be employed to synthesize the diketopiperazines of the invention. See, e.g., U.S. Pat. Nos. 4,694,081, 5,817,751, 5,990,112, 5,932,579 and 6,555,543, US Patent Application Publication Number 2004/0024180, PCT applications WO 96/00391 and WO 97/48685, and Smith et al., Bioorg. Med. Chem. Letters, 8, 2369-2374 (1998), the complete disclosures of which are incorporated herein by reference.

For instance, diketopiperazines, such as DA-DKP, can be prepared by first synthesizing dipeptides. The dipeptides can be synthesized by methods well known in the art using L-amino acids, D-amino acids or a combination of D- and L-amino acids. For example, solid-phase peptide synthetic methods can be used. Of course, dipeptides are also available commercially from numerous sources, including DMI Synthesis Ltd., Cardiff, UK (custom synthesis), Sigma-Aldrich, St. Louis, Mo. (primarily custom synthesis), Phoenix Pharmaceuticals, Inc., Belmont, Calif. (custom synthesis), Fisher Scientific (custom synthesis) and Advanced ChemTech, Louisville, Ky.

Once the dipeptide is synthesized or purchased, it is cyclized to form a diketopiperazine. This can be accomplished by a variety of techniques. For example, U.S. Patent Application Publication Number 2004/0024180 describes a method of cyclizing dipeptides. Briefly, the dipeptide is heated in an organic solvent while removing water by distillation. Preferably, the organic solvent is a low-boiling azeotrope with water, such as acetonitrile, allyl alcohol, benzene, benzyl alcohol, n-butanol, 2-butanol, t-butanol, acetic acid butylester, carbon tetrachloride, chlorobenzene chloroform, cyclohexane, 1,2-dichlorethane, diethylacetal, dimethylacetal, acetic acid ethylester, heptane, methyl-isobutylketone, 3-pentanol, toluene and xylene. The temperature depends on the reaction speed at which the cyclization takes place and on the type of azeotropic agent used. The reaction is preferably carried out at 50-200° C., more preferably 80-150° C. The pH range in which cyclization takes place can be easily determined by the person skilled in the art. It will advantageously be 2-9, preferably 3-7.

When one of the amino acids of the dipeptide has, or is derivatized to have, a carboxyl group on its side chain (e.g., aspartic acid), the dipeptide is preferably cyclized as described in U.S. Pat. No. 6,555,543. Briefly, the dipeptide, with the side-chain carboxyl still protected, is heated under neutral conditions. Typically, the dipeptide will be heated at from about 80° C. to about 180° C., preferably at about 120° C. The solvent will be a neutral solvent. For instance, the solvent may comprise an alcohol (such as butanol, methanol, ethanol, and higher alcohols, but not phenol) and an azeotropic co-solvent (such as toluene, benzene, or xylene). Preferably, the alcohol is butan-2-ol, and the azeotropic co-solvent is toluene. The heating is continued until the reaction is complete, and such times can be determined empirically. Typically, the dipeptide will be cyclized by refluxing it for about 8-24 hours, preferably about 18 hours. Finally, the protecting group is removed from the diketopiperazine. In doing so, the use of strong acids (mineral acids, such as sulfuric or hydrochloric acids), strong bases (alkaline bases, such as potassium hydroxide or sodium hydroxide), and strong reducing agents (e.g., lithium aluminum hydride) should be avoided, in order to maintain the chirality of the final compound.

Dipeptides made on solid phase resins can be cyclized and released from the resin in one step. See, e.g., U.S. Pat. No. 5,817,751. For instance, the resin having an N-alkylated dipeptide attached is suspended in toluene or toluene/ethanol in the presence of acetic acid (e.g., 1%) or triethylamine (e.g., 4%). Typically, basic cyclization conditions are preferred for their faster cyclization times.

Other methods of cyclizing dipeptides and of making diketopiperazines are known in the art and can be used in the preparation of diketopiperazines useful in the practice of the invention. See, e.g., those references listed above. In addition, many diketopiperazines suitable for use in the present invention can be made as described below from proteins and peptides. Further, diketopiperazines for use in the practice of the invention can be obtained commercially from, e.g., DMI Synthesis Ltd., Cardiff, UK (custom synthesis).

The DA-DKP composition and/or products of the present invention can be prepared from solutions containing DA-DKP, including from the commercially-available pharmaceutical compositions comprising albumin, such as human serum albumin. It has been found that DA-DKP is present in some commercially-available intravenous pharmaceutical compositions containing albumin. The DA-DKP present in these pharmaceutical preparations is formed by the heating steps often used in the manufacture of these pharmaceutical compositions. The heating results in cleavage and cyclization of the two N-terminal amino acids of the proteins to form DA-DKP.

Accordingly, DA-DKP can be prepared by heating solutions of albumin as well as other proteins and peptides. For example, a solution of albumin in phosphate buffer at neutral pH is prepared. Preferably, the solution is a concentrated solution (e.g., about 100-500 mM) to achieve protonation of the N-terminal amino acid. The solution is heated at 60° C. for from about 2 hours to several days, preferably about 4 days, to cause formation of DA-DKP. Denaturation of the protein should, preferably, be avoided. This can be accomplished by using shorter times and/or by adding caprylic acid or N-acetyl tryptophan at about 0.02 M for each.

DA-DKP can also be prepared by contacting a solution of albumin with an enzyme that can cleave the two N-terminal amino acids from the protein or peptide (e.g., dipeptidyl peptidases, particularly DPP IV). Suitable dipeptidyl peptidases are available commercially from, e.g., Sigma. The reaction should be conducted at pH 6-8, preferably in a buffer, such as phosphate buffer, at a temperature high enough to speed the reaction but not so high that the protein is denatured (e.g., 37° C.).

Preparation of the DA-DKP compositions can be by well known methods, such as ultrafiltration, chromatography (e.g., size-exclusion chromatography), affinity chromatography (e.g., using a column of beads having attached thereto an antibody or antibodies directed to the desired diketopiperazine(s) or an antibody or antibodies directed to the truncated protein or peptide), anion exchange or cation exchange, sucrose gradient centrifugation, chromatography, salt precipitation, or sonication, that will remove some or all of the albumin in the solution. The resultant DA-DKP-containing composition and/or product can be used and incorporated into pharmaceutical compositions as described above.

In a specific embodiment, a composition of the invention is prepared by treating an albumin-containing feed stream by tangential flow filtration. As used herein, the term "tangential flow" refers to the direction of flow of the albumin-containing feed stream relative to the filtration media. This flow direction may be either tangential (also commonly referred to as "cross flow"), or "normal flow", or a combination of both. Tangential flow refers to an albumin-containing feed stream characterized by most of the stream flowing across the filtration media surface, whereas normal flow refers to a stream characterized by most of the stream flowing through the filtration media, at a 90° angle relative to the filtration media surface.

In another embodiment, a composition of the invention is produced by treating an albumin-containing feed stream by chromatography. Reference herein to chromatography is to the mechanical and/or physical operation of separating one fraction of the albumin-containing feed stream from the remaining fraction by use of a pressure drop across a stationary phase. The term "mechanical chromatography" as used herein refers to, but is not limited to, size exclusion chromatography. The term "physical chromatography" as used herein refers to, but is not limited to, affinity chromatography, ion exchange chromatography, fast protein liquid chromatography and immunoaffinity chromatography.

The stationary phase of a chromatography step, may include, but is not limited to, resins (i.e. polystyrene, polystyrene divinylbenzene and polyacrylamide), ion exchange resins (i.e. sulfonated, quaternary ammonium, carboxylate and diethyl ammounium functional groups), cross-linked agarose, cross-linked dextrans, phosphocellulose, porous glass and silica, alumina and zirconia matrices. Further, the stationary phase may be immobilized on a solid support particle, or on the inner wall of a cylinder, either by physical attraction, chemical bonding, and or by in situ polymerization after coating. The immobilized stationary phase may coat the outer surfaces of the particles and cylinder, and/or fill any available pores within the solid particles. The stationary phase may be functionalized with biospecific ligands which include, but is not limited to, antibodies, protein receptors, steroid hormones, vitamins and enzyme inhibitors.

Using an ultrafiltration separation method, a human serum albumin composition can be passed over an ultrafiltration membrane having a molecular weight cut-off that retains the albumin while the DA-DKP passes into the resulting filtrate or fraction. This filtrate may comprise components having molecular weights less than about 50 kDA, less than about 40 kDa, less than 30 kDa, less than about 20 kDa, less than about 10 kDa, less than about 5 kDa, less than about 3 kDa. Preferably, the filtrate comprises components having molecular weights less than about 5 Da (also referred to as "<5000 MW"). This <5000 MW fraction or filtrate contains DA-DKP which is formed after the dipeptide aspartate-alanine is cleaved from albumin and subsequently cyclized into the diketopiperazine.

Physiologically-acceptable salts of the DA-DKP of the invention may also be used in the practice of the invention. Physiologically-acceptable salts include conventional non-toxic salts, such as salts derived from inorganic acids (such as hydrochloric, hydrobromic, sulfuric, phosphoric, nitric, and the like), organic acids (such as acetic, propionic, succinic, glycolic, stearic, lactic, malic, tartaric, citric, glutamic, aspartic, benzoic, salicylic, oxalic, ascorbic acid, and the like) or bases (such as the hydroxide, carbonate or bicarbonate of a pharmaceutically-acceptable metal cation or organic cations derived from N,N-dibenzylethylenediamine, D-glucosamine, or ethylenediamine). The salts are prepared in a conventional manner, e.g., by neutralizing the free base form of the compound with an acid.

The composition of the present invention can be a pharmaceutical solution having a DA-DKP concentration range with a lower endpoint of about 10 µM, about 20 µM, about 30 µM, about 40 µM, about 50 µM, about 60 µM, about 70 µM, about 80 µM, about 90 µM, about 100 µM, about 110 µM, about 120 µM, about 130 µM, about 140 µM, about 150 µM, about 160 µM, about 170 µM, about 180 µM, about 190 µM, about 200 µM, about 210 µM, about 220 µM, about 230 µM, about 240 µM, about 240, about 250 µM, about 260 µM, about 270 µM, about 280 µM, about 290 µM, about 300 µM, about 310 µM, about 320 µM, about 330 µM, about 340 µM, about 350 µM, about 360 µM, about 370 µM, about 380 µM, about 390 µM, or about 400 µM. The composition of the present invention may be a pharmaceutical solution having a DA-DKP concentration range with an upper endpoint of about 600 µM, about 580 µM, about 570 µM, about 560 µM, about 550 µM, about 540 µM, about 530 µM, about 520 µM, about 510 µM, about 500 µM, about 490 µM, about 480 µM, about 470 µM, about 460 µM, about 450 µM, about 440 µM, about 430 µM, about 420 µM, about 410 µM, about 400 µM, about 390 µM, about 380 µM, about 370 µM, about 360 µM, about 350, about 340 µM, about 330 µM, about 320 µM, about 310 µM, about 300 µM, about 290 µM, about 280, about 270 µM, about 260 µM, about 250 µM, about 240 µM, about 230 µM, about 220 µM, about 210 µM, or about 200 µM.

An effective amount of DA-DKP in the composition of the present invention for treating conditions described herein can be a range with a lower endpoint of about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 110 µg, about 120 µg, about 130 µg, about 140 µg, about 150

µg, about 160 µg, about 170 µg, about 180 µg, about 190 µg, about 200 µg, about 210 µg, about 220 µg, about 230 µg, about 240 µg, about 250 µg, about 260 µg, about 270 µg, about 280 µg, about 290 µg, about 300 µg, about 310 µg, about 320 µg, about 330 µg, about 340 µg, about 350 µg, about 360 µg, about 370 µg, about 380 µg, about 390 µg, about 400 µg, about 425 µg, about 450 µg, about 475 µg or about 500 µg. In addition, an effective amount of DA-DKP in the composition of the present invention for treating conditions described herein can be a range with upper endpoint of about 500 µg, about 490 µg, about 480 µg, about 470 µg, about 460 µg, about 450 µg, about 440 µg, about 430 µg, about 420 µg, about 410 µg, about 400 µg, about 390 µg, about 380 µg, about 370 µg, about 360 µg, about 350 µg, about 340 µg, about 330 µg, about 320 µg, about 310 µg, about 300 µg, about 290 µg, about 280 µg, about 270 µg, about 260 µg, about 250 µg, about 240 µg, about 230 µg, about 220 µg, about 210 µg, about 200 µg, about 190 µg, about 180 µg, about 170 µg, about 160 µg, about 150 µg, about 140 µg, about 130 µg, about 120 µg, about 110 µg, about 100 µg, about 90 µg, about 80 µg, about 70 µg, about 60 µg, about 50 µg, about 40 µg, about 30 µg, or about 20 µg.

Dosage forms for the topical or transdermal administration of compounds of the invention include powders, sprays, ointments, pastes, creams, lotions, gels, solutions, patches, and drops. The active ingredient may be mixed under sterile conditions with a pharmaceutically-acceptable carrier, and with any buffers, or propellants which may be required.

The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Kits comprising the pharmaceutical products of the present invention are also provided. The kits can comprise a DA-DKP composition formulated for administration by injection. The DA-DKP can be prepared as described herein, such as by removing albumin from a solution of a human albumin composition. The kits may contain unit-dose or multi-dose sealed containers, for example, ampoules and vials, and may be stored in a lyophilized condition requiring only the addition of the sterile liquid carrier, for example water for injection, immediately prior to use. The kits may also be stored in a condition, wherein the contents are ready for direct use or injection.

While it is possible for a compound of the present invention to be administered alone, it is preferable to administer the compound as a pharmaceutical formulation (composition). The pharmaceutical compositions of the invention comprise a compound or compounds of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the animal. Pharmaceutically-acceptable carriers are well known in the art. Regardless of the route of administration selected, the compounds of the present invention are formulated into pharmaceutically-acceptable dosage forms by conventional methods known to those of skill in the art. See, e.g., Remington's Pharmaceutical Sciences.

The composition of the present invention may further comprise N-acetyl-tryptophan (NAT), caprylic acid, caprylate or combinations thereof. Preferably, the composition may comprise NAT. Compositions of the present invention having NAT, caprylic acid, caprylate or combinations thereof may be a pharmaceutical composition having a NAT, caprylic acid, caprylate or combinations thereof in a concentration range with a lower endpoint of about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, or about 20 mM. In addition, compositions of the present invention having NAT, caprylic acid, caprylate or combinations thereof may be a pharmaceutical composition having a NAT, caprylic acid, caprylate or combinations thereof in a concentration range with an upper endpoint of about 40 mM, about 39 mM, about 38 mM, about 37 mM, about 36 mM, about 35 mM, about 34 mM, about 33 mM, about 32 mM, about 31 mM, about 30 mM, about 29 mM, about 28 mM, about 27 mM, about 26 mM, about 25 mM, about 24 mM, about 23 mM, about 22, or about 21 mM. Preferably, the concentration range is about 4 mM to about 20 mM.

In addition, the composition of the present invention may also comprise a second drug such as an analgesic (such as lidocaine or paracetoamol), an anti-inflammatory (such as bethamethasone, non-steroid anti-inflammatory drugs (NSAIDs), acetaminophen, ibuprofen, naproxen), and/or other suitable drugs.

Instead of purifying the DA-DKP, pharmaceutical compositions comprising albumin found in the mammalian recipient of the treatments of this disclosure can be administered to stimulate stem cell expansion in the mammal. Although compositions comprising these proteins and/or peptides which are currently available commercially can be used if they contain diketopiperazines, especially DA-DKP, it is preferred to treat the albumin as described above to increase the content of the DA-DKP before administration of the improved compositions. The mammal is preferably a human, and the proteins and/or peptides are preferably human proteins and/or peptides. Parenteral routes of administration are preferred.

Using the compositions or cell culture media supplemented with the compositions of the present invention, the growth, expansion, and differentiation of stem cells can be regulated by the addition of defined growth factors or other cytokines. Such influence over stem cells in typical serum-containing culture is not possible as undefined components in serum obscure the cellular responses to defined factors. Thus, using the compositions of the present invention, stem cells can be expanded and differentiated in suspension culture and in the absence of stromal cells, collagen, or support matrices.

The supplement and compositions or cell culture media supplemented with the compositions of the present invention provide for the growth and expansion of both pluripotent stem cell populations and differentiated progeny.

The compositions or cell culture media supplemented with the compositions of the present invention can be used to culture stem cells derived from a number of animals, including human, monkey, ape, mouse, rat, hamster, rabbit, guinea pig, cow, swine, dog, horse, cat, goat, and sheep. Preferably, human stem cells are cultured. Still another specific embodiment of aspects one or two is one in which the stem cells are totipotent, pluripotent or multipotent stem cells. In a particular embodiment, the stem cells are embryonic stem cells, fetal stem cells, extraembryonic stem cells or adult stem cells.

The compositions or cell culture media supplemented with the compositions of the present invention may also include one or more ingredients selected from the group consisting of one or more antioxidants, one or more albumins or albumin substitutes, one or more lipid agents, one or more insulins or insulin substitutes, one or more transferrins or transferrin substitutes, one or more trace elements, one or more glucocorticoids, N-acetyl-L cysteine, Human Ex-Cite®, ethanolamine, human zinc insulin, human iron saturated transferrin, selenium, hydrocortisone, D,L-tocopherol acetate, and 2-mercaptoethanol. For example, N-acetyl-L-cysteine can be solubilized in double-distilled water. The pH of the N-acetyl-L-cysteine at this point is approximately 2.0. To prevent protein denaturation, the pH of the N-acetyl-L-cysteine is adjusted to 7.0 with 5N sodium hydroxide and is added to the mixture. The entire mixture is then filtered through a 0.2 micron low protein binding filter.

The supplement or the medium of the present invention can be in liquid form or can be maintained in dry form. The type of liquid carrier and the method used to dissolve the ingredients into solution vary and can be determined by one of ordinary skill in the art with no more than routine experimentation. In general, the liquid carrier is water.

The supplement or the medium or concentrated formulation of the present invention (both aqueous and dry forms) are typically sterilized to prevent unwanted contamination. Sterilization may be accomplished, for example, by ultraviolet light, filtration, or heat.

All of the ingredients of the supplement of the present invention which are of human origin (e.g., human serum albumin, transferrin) are heat treated, prior to use, by heating at 60° C. for 10 hours.

Those of ordinary skill in the art are familiar with methods for culturing hematopoietic cells. For example, guidelines for hematopoietic cell culture are outlined in Freshney, R. I. et al., Eds., Culture of Hematopoietic Cells, Wiley-Liss, New York, 1994, pp. 81-98.

The present invention also provides a kit comprising a carrier means such as a box or carton being compartmentalized to receive in close confinement therein one or more container means such as vials, tubes, ampules, jars, and the like, wherein a first container means contains the compositions or cell culture media supplemented with the compositions of the present invention. Optionally, a second container means contains a basal medium. Preferably, the container containing the supplement of the present invention can be stored from about −135 to about 4° C., preferably from about −5 to about −80° C., most preferably from about −5 to about −20° C., and still more preferably at about −20° C. A container containing the medium of the invention is preferably stored at about 2 to about 8° C., and most preferably at about 4° C.

The present invention also provides a composition comprising stem cells in a serum-free medium, wherein the serum-free medium, which is supplemented with compositions of the present invention, which is capable of supporting the growth of stem cells in serum-free culture. Aliquots of this composition can be frozen at about −80° C. and below. Aliquots of this composition can be stored indefinitely at less than or equal to about −135° C. After an aliquot of the composition has been thawed and opened, using sterile cell culture technique, the stem cells can be cultivated in serum-free culture.

Another embodiment is the use of a composition of the invention in storage and transportation of stem cells in order to maintain viability, mobility and stem cell function. A composition of the invention may be used alone or added to a variety of agents known in the art to allow transportation of stem cells. This is particularly important in situations of bone marrow stem cell transportation in which cell freezing and thawing is not performed in numerous situations. The ability to adequately store stem cells during transportation would allow for tissue extraction at separate physical locations from the stem cell processing facility.

Another embodiment of the invention is a pharmaceutical preparation comprising a composition of the invention generated in a Good Manufacturing Practices/Good Tissue Practices environment such that it is suitable for clinical use. Subsequent to concentration and quantification of units of activity, the composition of the invention can be diluted into an excipient or carrier. It may be advantageous to formulate compositions in dosage unit form for ease of administration and uniformity of dosage. Dosage unit form as used herein refers to physically discrete units suited as unitary dosages for an individual to be treated; each unit containing a predetermined quantity of active compounds of the compositions of the invention calculated to produce the desired therapeutic effect in association with the required pharmaceutical carrier. The dosage unit forms of the invention are dependent upon the amount of a composition necessary to stimulate proliferation of the respective stem cells whose proliferation and/or differentiation is being sought. The amount of composition necessary to stimulate proliferation and/or differentiation of the desired stem cells can be formulated in a single dose, or can be formulated in multiple dosage units. Treatment can require a one-time dose, or can require repeated doses.

Actual formulation of the compositions of the invention will be performed in agreement with standard practices that are known to one skilled in the art. These are well known in the art and the one chosen is based upon the route of administration that will be used, as well as specific pharmacokinetic properties that are desired. For example, the preferred embodiment of therapy utilizing a composition of the invention is an injectable dosage, and more preferably, an injection formulated for administration into the specific area requiring regeneration of stem cells. However, several embodiments are possible. For example, routes of administration can include parenteral, e.g, intra-articular injection, intravenously, intradermally, intraspinally, intraperitoneally, subcutaneously, or intramuscularly, oral (e.g., ingestion or inhalation), transdermal (topical), transmucosal, and rectal administration. Solutions or suspensions for formulating therapeutic compositions of the invention can include: sterile diluent such as water for injection, saline solution (e.g., phosphate buffered saline (PBS, UPS)), fixed oils, glycerine, or other synthetic solvents; antibacterial and antifungal agents such as parabens, a polyol (for example, glycerol, propylene glycol, and liquid polyetheylene glycol, and the like), chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The desired fluidity can be maintained, for example, by the use of a coating such as lecithin, by the maintenance of the required particle size in the case of dispersion and by the use of surfactants. In many cases, it will be preferable to include isotonic agents, for example, sugars, sodium chloride, polyalcohols such as mannitol or sorbitol, and in the composition. Prolonged administration of the injectable compositions can be brought about by including an agent that delays absorption. Such agents include, for example, aluminum monostearate and gelatin. The parenteral preparation can be enclosed in ampules, disposable syringes, or multiple dose vials made of glass or plastic. It is known in the art, and common practice for oral compositions to generally include an inert diluent or an edible carrier. Oral compositions can be liquid, or can be enclosed in gelatin capsules or compressed into tablets. Tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; colloidal silicon dioxide. Transmucosal administration can be accomplished through the use of nasal sprays or suppositories. For transdermal administration, the active compounds are formulated into ointments, salves, gels, or creams as generally known in the art.

In Vivo Methods of Treatment

Embodiments of the invention include the use of the compositions of the invention to effect the mobilization, homing, differentiation and/or expansion of stem cells within a living organism. Clinical situations where administration of the compositions of the invention is desirable include conditions where an increase in the number of stem cells is sought due to disease or senescence of endogenous stem cells or conditions benefiting from reparative function on the surrounding tissues or elsewhere in the organism. Such stem cells can be present in pancreatic tissue, liver tissue, smooth muscle tissue, striated muscle tissue, cardiac muscle tissue, bone tissue, bone marrow tissue, bone spongy tissue, cartilage tissue, liver tissue, pancreas tissue, pancreatic ductal tissue, spleen tissue, thymus tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue (including retinal tissue), lung tissue, testicular tissue, ovarian tissue, prostate tissue, connective tissue, endocrine tissue, and mesentery tissue.

Administration of the compositions of the invention can be performed systemically, or in a localized environment in the subject. For example, a site of local administration can be any site in the body in which the development of tissue is desired or beneficial, such as a joint, a surgical site, a site of a segmented skeletal gap or non-union fracture, a wound, an ulcer, or an inflammatory skin rash. The compositions of the invention can also be administered systemically, such as by an oral dosage formulation. Further, compositions of the invention can be administered to a subject in, on or as part of an implantable device. For example, such a device can be a sponge, biocompatible polymer, bioerodible polymer, putty, gel, bone matrix, artificial bone matrix, bolt, screw, endotracheal tube, stent, contact lens, pacemaker, central IV tube, foley catheter, or intracranial device.

The invention includes a method to cause an effect selected from stem cell mobilization, stem cell homing, stem cell expansion, and stem cell differentiation in a subject by administering DA-DKP to a subject that has a need therefor. In this method, the step of administering DA-DKP can have an effect of increasing the production of one or more of CXCR4, CXCL12, MMP13, MMP14, aggrecan, SDF1, and collagen 2A1. In addition, the step of administering DA-DKP can have an effect of decreasing production of one or more proteins selected from MAPK-activated protein kinase 3, beta-adrenergic receptor kinase 1, ADAM metallopeptidase with thrombodpondin type I motif, MAPK-activated protein kinase 2, C-Src kinase, Macrophage Scavenger Receptor, Noggin, Tyrosine kinase Bruton, Glycogen synthase kinase-3 alpha/beta, Glycogen synthase kinase-3 alpha/beta, HSP 90 alpha/beta, HSP 90 alpha/beta, Phosphoinositide-3-kinase, catalytic subunit alpha, and Eukaryotic translation initiation factor 4A, and Fibroblast Growth Factor 17, and in particular, one or more proteins selected from MAPK-activated protein kinase 3, Noggin, and Phosphoinositide-3-kinase, catalytic subunit alpha. Further, the step of administering DA-DKP can have an effect of increasing production of one or more proteins selected from Clusterin (Apolipoprotein J), Prothrombin, C1QBP (Hyaluronan binding protein 1), TNF SF 15 (VEGF inhibitor), Mammaglobin 2, MIP3b (CCL 19), MCP 1 (CCL 2), PTHrP, Spondin 1, Elafin (elastase inhibitor), IL 11, NPS-PLA2, CFC 1 (cryptic protein), Testican 1 (SPOCK 1), Angiogenin, URB, MMP-3, IP10 (cxcl 10), BSSP 4, IL 8 (cxcl 8), RSPO2, Cystatin C, bFGF, Factor H, Coagulation Factor IX, SDF-1 (cxcl 12), CATC (Dipeptidyl peptidase 1), PIGR, Ck-b-8-1 (MPIF 1 splice variant), Cls, EMR2, ART, DPP 2, SAA, TIMP-1, and Semaphorin 3A, and in particular, one or more proteins selected from Clusterin (Apolipoprotein J), C1QBP (Hyaluronan binding protein 1), MCP 1 (CCL 2), PTHrP, Elafin (elastase inhibitor), IL 11, MMP-3, bFGF, SAA, TIMP-1, Semaphorin 3A, and combinations thereof. In a more particular embodiment, the administration of DA-DKP can decrease the production of a protein selected from MAPK-activated protein kinase 3, Noggin, Phosphoinositide-3-kinase, catalytic subunit alpha, and combinations thereof and increase the production of a protein selected from Clusterin (Apolipoprotein J), C1QBP (Hyaluronan binding protein 1), MCP 1 (CCL 2), PTHrP, Elafin (elastase inhibitor), IL 11, MMP-3, bFGF, SAA, TIMP-1, Semaphorin 3A, and combinations thereof. The administration of DA-DKP can also down regulate Akt pathways in the subject. Methods of the invention include methods for stimulating development of tissue in a subject by administering DA-DKP to a subject. These methods are suitable for the development of any tissue in the subject, including one or more of nervous system tissue, adipose tissue, liver tissue, smooth muscle tissue, striated muscle tissue, cardiac muscle tissue, bone tissue, bone spongy tissue, cartilage tissue, pancreatic ductal tissue, spleen tissue, thymus tissue, tonsil tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue.

A specific in vivo method of treatment includes conditions in which a higher number and/or more rapid recovery of stem cells is needed in a subject after a medical procedure. For example, after a bone marrow transplant, expansion of hematopoietic cells is desirable in order for the patient not to succumb to bacterial or viral infections. Such expansion of granulocytic and monocytic precursors would be useful in enhancing immunological defenses subsequent to a bone marrow transplant. Accordingly, this invention provides methods and compositions that can be administered to a patient having undergone a bone marrow transplant.

Another embodiment of an in vivo method is supporting the expansion of endogenous stem cells after an injury has occurred and the endogenous stem cells are mobilized or begin to differentiate, but do not do so at high enough levels to stimulate a beneficial response. Thus, a further embodiment of the invention is the administration of compositions of the invention to patients having an injury in a tissue selected from pancreatic tissue, liver tissue, smooth muscle tissue, striated muscle tissue, cardiac muscle tissue, bone tissue, bone marrow tissue, bone spongy tissue, cartilage tissue, liver tissue, pancreas tissue, pancreatic ductal tissue, spleen tissue, thymus tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue (including retinal tissue), lung tissue, testicular tissue, ovarian tissue, prostate tissue, connective tissue, endocrine tissue, and mesentery tissue.

Another embodiment of the invention is the administration of a composition of the invention alone or in combination with growth factors to promote healing.

Another embodiment of the invention is a method of treatment for diabetes by administering compositions of the invention to a subject with diabetes to induce islet regeneration. This method can further include administration of other factors capable of inducing islet regeneration. Such factors can be, for example, soluble proteins, membrane bound proteins, or intracellular acting transcription factors. For example, it is known that administration into mice combinations of GLP-1, EGF and gastrin leads to regeneration of islets or islet-like cells that are functionally effective in models like NOD or streptozocin induced diabetes. Compositions of the invention can be added to cultures of differentiating islets in vitro to expand the stem cell numbers, but can also be administered directly to the pancreas of a patient in vivo in order to restore islet cell function or to amplify the effect of administered hormones.

Another embodiment of an in vivo method of the invention is a treatment for multiple sclerosis by administering a composition of the invention to a patient having multiple sclerosis for expanding neuronal progenitor cells. Alternatively, a composition of the invention can be administered to patients suffering from multiple sclerosis alone or in combination with agents capable of inhibiting the autoimmune process. Synergy in therapeutic effects is anticipated through the concurrent induction of tissue healing and immune system repair.

Another embodiment of the invention is the treatment of an immunological disorder, such as an autoimmune disorder, by extracting stem cells from an autologous patient, treating the cells with a composition of the invention and/or other combinations of stem cell-expanding compounds, ablating the immune system of the patient, and subsequent reintroduction of stem cells into the host for reconstitution. A composition of the invention may be subsequently provided directly to the host in order to accelerate reconstitution of hematopoiesis. Autoimmune diseases treatable by these procedures include, but are not limited to, Type 1 diabetes, multiple sclerosis, rheumatoid arthritis, systemic sclerosis, Hashimoto's thyroiditis, myasthenia gravis, scleroderma, systemic lupus erythromatosis, graft versus host disease, and the like.

Another embodiment of the invention is a treatment for an autoimmune disorder such as Type 1 diabetes, multiple sclerosis, rheumatoid arthritis, Hashimoto's thyroiditis, myasthenia gravis, scleroderma, and the like comprising administering a composition of the invention to a relevant location within the organism in need of such treatment to enhance the production of stem cells, such as administration into a joint or into the pancreas of an organism to enhance chondrogenesis or islet cell production.

Another embodiment of the invention includes the use of a composition of the invention for expansion of antigen-specific and/or non-specific immune regulatory cells within an organism. Expansion of such cells is use for controlling pathological immune responses. For example, it is known that Th2 cells, TR1 cells, CD4+CD25+FoxP3+ cells, and CD3+ double negative cells, are capable of suppressing immune responses in an antigen specific manner, whereas NKT cells, myeloid suppressor cells, M2 cells, and immature dendritic cells are capable of suppressing immune responses in an antigen non-specific manner. A composition of the invention may be used for ex vivo culture and expansion of immune regulatory cells derived from a patient in need thereof. A composition of the invention may be used either alone or in combination with factors known to be involved in the development of said cells for administration to an organism to enhance proliferation of these cells without loss of function.

Another embodiment of the invention is a treatment for stroke by administration of a composition of the present invention to a stroke patient to cause the in vivo mobilization, homing, expansion and/or differentiation of endogenous neural cells. This method can further include administration of a composition of the invention in combination with polypeptides and proteins known in the art to expand neural cells.

Another embodiment of the invention is the use of a composition of the invention as an adjuvant to treatment for a degenerative condition by the application of a combination of a composition of the invention with known therapies in order to enhance the beneficial effects of known therapies.

Another embodiment of the invention relates to the use of a composition of the invention described herein in the preparation of a medicament for enhancing the expansion of stem cells in vivo or ex vivo.

A further embodiment of the invention is an in vivo method for the treatment of a degenerative joint disease by administration of a composition of the invention to cause stem cell mobilization, homing, expansion and/or differentiation in the subject. A degenerative joint disease is a gradual deterioration of the articular cartilage that covers joints. A degenerative joint disease (osteoarthritis) is a noninfectious progressive disorder of the weightbearing joints. The normal articular joint cartilage is smooth, white, and translucent. It is composed of cartilage cells (chondrocytes) imbedded in a sponge-like matrix made of collagen, protein polysaccharides, and water. With early primary arthritis, the cartilage becomes yellow and opaque with localized areas of softening and roughening of the surfaces. As degeneration progresses, the soft areas become cracked and worn, exposing bone under the cartilage. The bone then begins to remodel and increase in density while any remaining cartilage begins to fray. Eventually, osteophytes (spurs of new bone) covered by cartilage form at the edge of the joint. As mechanical wear increases, the cartilage needs repairing. The cartilage cells are unable to produce enough of the sponge-like matrix and therefore the damaged cartilage cannot repair itself. The cartilage has no blood supply to enhance healing. The majority of degenerative joint disease is the result of mechanical instabilities or aging changes within the joint. This includes old age degenerative arthritis and, in younger individuals, may be the result of injuries, bruises, abnormal joint configuration (i.e. hip dysplasia), or mechanical wear from anterior cruciate ligament rupture, patellar luxation, or osteochondritis dissecans, for example. Degenerative joint disease can occur at any joint in the body, including without limitation, knee, hip, shoulder, hand and spine.

Conventional pharmaceutical therapies for degenerative joint disease include administration of acetaminophen, non-steroidal anti-inflammatory drugs (NSAIDS), narcotics, and corticosteroids.

A particular embodiment of the invention is a method of stimulating chondrogenesis in a subject by administering a pharmaceutical composition that includes DA-DKP. The pharmaceutical composition can include any pharmaceutical composition described herein and therefore, can also include a component selected from N-acetyl tryptophan, caprylate, caprylic acid, and combinations. In this method, chondrogenesis can be stimulated in a stem cell, and the stem cell can be a progenitor cell or a mesenchymal stem call (MSC). The stimulation of chondrogenesis in this method can promote cartilage, bone, and/or ligament repair or induce repair or regeneration of chondral tissue in the subject. Thus, the method is useful for treating or ameliorating a chondrogenic disease, such as a congenital cartilage disease, degenerative or fibrotic joint, rheumatoid arthritis or osteoarthritis, in the subject. Also, the chondrogenesis can be useful to treat or repair a condition selected from a cartilage defect, a skeletal defect, and a fracture arising from trauma or surgery. For example, a skeletal defect can be a large segmental skeletal gap, and the cartilage defect can be an articular cartilage tear, a congenital cartilage defect or cartilage damage induced by bone fractures.

This method can be conducted by stimulating stem cells ex vivo and then administering the stimulated stem cells to the subject. For example, the stem cells can be stimulated ex vivo by culturing a population of stem cells of chondrocyte lineage with DA-DKP, or composition comprising a DA-DKP, for a time sufficient to stimulate chondrogenesis, and then, be implanted into a desired site in the subject.

This method can result in increased production of collagen, including type 2A1 collagen and/or type 1A1 collagen. Specifically, the chondrogenesis can result in at least a 2-fold, 4-fold, 10-fold, 20-fold, 25-fold increase in the production of collagen. A further embodiment of the present invention includes a method of stimulating development of nervous tissue in a subject by administering a pharmaceutical composition that includes DA-DKP. The pharmaceutical composition can include any pharmaceutical composition described herein and therefore, can also include a component selected from N-acetyl tryptophan, caprylate, caprylic acid, and combinations thereof to a subject. In this method, the development of nervous tissue can be stimulated in a stem cell, which can be selected from a progenitor cell and mesenchymal stem call (MSC). The stimulation of development of nervous tissue can promote brain, spinal cord, and/or peripheral nerve repair or induces repair or regeneration of neurons, neuroglia, and/or astrocytes in the subject. Further, the development of nervous tissue can treat or ameliorate a disease of the central nervous system and/or a disease of the peripheral nervous system in the subject. Such diseases can be selected from neurodegenerative diseases. The development of nervous tissue can also treat or repair a condition selected from an injury arising from trauma or surgery.

This method can be conducted by stimulating stem cells ex vivo and then administering the stimulated stem cells to the subject. For example, the stem cells can be stimulated ex vivo by culturing a population of stem cells of neuron, neuroglia, and/or astrocyte lineage with the pharmaceutical composition, for a time sufficient to stimulate development of nervous tissue and then, be implanted into a desired site in the subject.

Ex Vivo Treatment Methods

Ex vivo expansion of stem cells for systemic administration represents an effective treatment modality for disorders or diseases susceptible to stem cell treatment. For example, in vitro expanded mesenchymal stem cells reduced both acute and chronic graft versus host disease in a patient suffering severe, grade IV graft versus host disease in the liver and gut subsequent to bone marrow transplant. Administration of 2 million cells/kg on day 73 after bone marrow transplant lead to a long term remission of graft versus host disease (Le Blanc, et al., 2004, Lancet 363:1439-1441).

The present invention further provides methods of increasing the expansion of stem cells ex vivo. The method involves contacting the stem cells with a composition of the invention or mixing or incubating the stem cells with a growth medium that includes a composition of the invention to expand the stem cell population for subsequent administration, either locally at a needed site or systemically. Such methods make possible the use of stem cell populations, such as mesenchymal stem cells, that expand relatively slowly and are therefore often not practical for widespread clinical use.

The compositions of the invention, in addition to increasing the rate of stem cell proliferation, may also maintain the stem cells in an undifferentiated state. Stem cells reside in unique physiological niches, and while growing cells within mimics of such niches has been performed, the mimics of the stem cell niche are often unusable in clinical situations. An example of this is the fact that early hematopoietic stem cells require feeder cell lines to be expanded in high quantities, or the fact that optimal growth of embryonic stem cells is still primarily achieved using murine feeders. The current invention provides compositions for enhancing the expansion of stem cells that may recreate conditions similar to stem cell niches using approaches that are translatable into the clinical situation.

As discussed above, methods of extracting, expanding and identifying specific phenotypes of stem cells is important for clinical implementation. For example, bone marrow is commonly used as a source of therapeutic stem cells for myocardial disease, angina, and hematopoietic cell transplant. However, bone marrow in general contains a wide number of different stem cells in addition to the standard, well known, hematopoietic, CD34+ stem cell. CD34− hematopoietic stem cells, mesenchymal stem cells, and myogenic precursor cells have all been found in bone marrow, in addition to T cells, B cells, and relatively high levels of CD4+CD25+T regulatory cells. Given the heterogeneity of bone marrow as a starting material for stem cell therapy, it is apparent that understanding of particular cell populations, as well as ability to isolate and expand them, would substantially advance the field of stem cell therapeutics.

Accordingly, whether a stem cell population is derived from adult or embryonic sources, the stem cells can be grown in a culture medium containing a composition of the invention to increase the population of a heterogeneous mixture of cells, or a purified stem cell population, in order to increase the rate of expansion or growth of the stem cells when grown in culture.

Several methods of growing stem cells outside of the body have been developed and are known in the art. Originally, the majority of work in the area of stem cell growth and expansion was performed in the hematopoietic system using bone marrow cells. The ability of either freshly isolated or cultured bone marrow cells to form colonies on methylcellulose or agar was used as an output.

The development of stem cell expansion techniques began with work aimed at increasing the number of colonies formed on semisolid media. Early experiments used a variety of uncharacterized sera and conditioned media. For example, trophoblast cell line conditioned media, xenogeneic stromal cell conditioned media, supernatants from tumor cells, and healthy lymphocytes were used. Work was also performed towards designing serum free systems, using ingredients such as human transferrin and bovine insulin. The specific advantage of such systems is that hematopoietic stem cells could be expanded without concurrent differentiation. The initial long term culture systems required the use of murine feeder (stromal) cells since human lines had certain disadvantages in terms of hematopoietic promoting activity. Numerous drawbacks existed to the use of murine feeder cell lines to maintain stem cell viability and proliferative potential. Due to this, an effort was made to overcome difficulties in growth of human derived feeder cells, and a variety of such cells have been developed.

Stem cells to be expanded by methods of the present invention can be isolated from any organ of any mammalian organism, by any means known to one of skill in the art. The stem cells can be derived from embryonic or adult tissue. One of skill of the art can determine how to isolate the stem cells from the particular organ or tissue of interest, using methods known in the art. The stem cell populations can also be enriched using antibodies to other stem cell surface markers. Such markers include, but are not limited to, FLK-1, AC133, CD34, c-kit, CXCR-4, Oct-4, Rex-1, CD9, CD13, CD29, CD44, CD166, CD90, CD105, SH-3, SH-4, TRA-1-60, TRA-1-81, SSEA-4, Sox-2, and the like. One of skill in the art will be able to determine the specific cell marker useful for isolating stem cells from the desired tissue.

One of skill in the art will be able to determine a suitable growth medium for initial preparation of stem cells. Commonly used growth media for stem cells includes, but is not limited to, Iscove's modified Dulbecco's Media (IMDM) media, DMEM, KO-DMEM, DMEM/F12, RPMI 1640 medium, McCoy's 5A medium, minimum essential medium alpha medium (α-MEM), F-12K nutrient mixture medium (Kaighn's modification, F-12K), X-vivo 20, Stemline, CC100, H2000, Stemspan, MCDB 131 Medium, Basal Media Eagle (BME), Glasgow Minimum Essential Media, Modified Eagle Medium (MEM), Opti-MEM I Reduced Serum Media, Waymouth's MB 752/1 Media, Williams Media E, Medium NCTC-109, neuroplasma medium, BGJb Medium, Brinster's BMOC-3 Medium, CMRL Medium, $CO_2$-Independent Medium, Leibovitz's L-15 Media, and the like.

If desired, other components, such as growth factors, can be added as desired. Exemplary growth factors and other components that can be added include but are not limited to thrombopoietin (TPO), stem cell factor (SCF), IL-1, IL-3, IL-7, flt-3 ligand (flt-3L), G-CSF, GM-CSF, Epo, FGF-1, FGF-2, FGF-4, FGF-20, IGF, EGF, NGF, LIF, PDGF, bone morphogenic proteins (BMP), activin-A, VEGF, forskolin, glucocorticords, and the like. Furthermore, the initial isolation media can contain either serum such as fetal calf, horse, or human serum, or more preferably, serum substitution components. Numerous agents have been introduced into media to alleviate the need for serum. For example, serum substitutes have included bovine serum albumin (BSA), insulin, 2-mercaptoethanol and transferrin (TF).

The stem cells can then be stored for a desired period of time, if needed. Stem cell storage methods are known to those of skill in the art. Typically, the stem cells are treated to a cryoprotection process, then stored frozen until needed.

The stem cells can be purified prior to contact with a composition of the invention by methods known in the art, using, for example, antibody technology such as panning of cells, through the use of fluorescence activated cell sorting (FACS) methods, or magnet activated cell sorting methods such as that MACS apparatus, to isolate cells having the desired stem cell markers, or to remove unwanted, contaminating cell types having unwanted cell markers prior to contacting with compositions of the invention. Other methods of stem cell purification or concentration can include the use of techniques such as counterflow centrifugal elutriation, equilibrium density centrifugation, velocity sedimentation at unit gravity, immune rosetting and immune adherence, T lymphocyte depletion. Examples of stem cell markers that can be useful in purification include, but are not limited to, FLK-1, AC133, CD34, c-kit, CXCR-4, Oct-4, Rex-1, CD9, CD13, CD29, CD44, CD166, CD90, CD105, SH-3, SH-4, TRA-1-60, TRA-1-81, SSEA-4, Sox-2, and the like. Examples of cell surface markers that can be used as markers of contaminating, unwanted cell types depends on the stem cell phenotype sought. For example, if collection of pluripotent hematopoietic cells is desired, contaminating cells will possess markers of commitment to the differentiated hematopoietic cells such as CD38 or CD33. Additionally, non-hematopoietic cell contamination would be detected by lack of CD45 expression. If selection of stromal mesenchymal cells is desired, then contaminating cells would be detected by expression of hematopoietic markers such as CD45. Additionally, stem cells can be purified based on properties such as size, density, adherence to certain substrates, or ability to efflux certain dyes such as Hoechst 33342 or Rhodamine 123.

The stem cells can be genetically modified at any stage of the preparation. For example, a gene encoding a selectable marker or other gene of interest can be introduced to the prepared stem cells.

To increase the growth of the stem cells, the stem cells are contacted with a composition of the invention or mixed or incubated with media that contains a composition of the invention.

Antibiotics, antifungals or other contamination preventive compounds can be added to the incubation media, if desired. Exemplary compounds include but are not limited to penicillin, streptomycin, gentamycin, fungizone or others known in the art.

Stem cells in contact with compositions of the invention may be expanded through multiple passages using techniques known to those of skill in the art. For example, the stem cells isolated from a subject are counted and the viable cell density determined using trypan blue dye exclusion methods. To subculture (or passage) cells, they are replated at a density of 5,000 cells/cm$^2$ into a culture medium containing a composition of the invention in new tissue culture flasks coated with protein such as gelatin or fibronectin, and allowed to grow in a humidified incubator at 37° C. and 5% $CO_2$. If necessary, culture medium is replenished. On reaching subconfluence (about 90%), the culture medium is removed and the adherent cells trypsinized with 0.25% trypsin and 1 mM EDTA for 3-5 min at 37° C. The adherent cells are rinsed twice with PBS prior to the trypsinization. The trypsin is neutralized, and the cells are pelleted by centrifugation at 300×g for 10 min and resuspended in warm culture medium that may also contain a composition of the invention. The cells are rinsed by centrifugation at 300×g for 10 min and resuspended in warm culture medium also containing a composition of the invention. Stem cells may be subcultured through multiple passages using the same passage protocol.

The stem cells can be contacted with compositions of the invention, for example, by simply mixing the composition(s) with the culture of stem cells. Mixing can be performed in a plethora of suitable vessels capable of maintaining viability of the stem cells. Said vessels can include but are not limited to tissue culture flasks, conical tubes, culture bags, bioreactors, or cultures that are continuously mixed. The stem cells can then be allowed to grow as desired. In some situations it will be desirable to use a combination culture system in which cells are first grown with one type of culture condition, then subsequently another culture condition is used. For example, when rapid expansion of hematopoietic stem cells is needed without differentiation, cells can be cultured initially in a high concentration of a composition of the invention for 48 hours, or a time period needed to induce cycling of the stem cells. Subsequently, media containing cytokines can be added into the culture for passages after the first 48 hours. One skilled in the art will understand that depending on stem cell type and level of differentiation desired, different concentrations of the compositions of the invention can be added at different time points of the culture. For example, in a particular culture situation, addition of compositions of the invention at the initiation of culture may not be optimum.

The desired ratio of stem cells to compositions of the invention can be determined by one of skill in the art. For example, a ratio of less than about 1:1,000 to 1,000:1 or more (stem cell preparation to composition of the invention) can be used. For example, a ratio of stem cell preparation to composition of the invention from about 1:750, 1:500, 1:250, or 1:100 to about 100:1, 250:1, 500:1, or 750:1 can be used. This ratio can vary, for example, depending on temperature, incubation time, number of stem cells, the desired activity sought in the stem cells, the type of stem cells, the purity of stem cells, the amount of placental tissue used as a starting point, and the like. The stem cells can be isolated from their growth media prior to contacting with a composition of the invention, or the stem cells can remain in their growth medium, with a composition of the invention added.

The length of time the stem cell is in contact with a composition of the invention can be determined by one of skill in the art. Generally, the contacting step can range from less than about 1 second, 30 seconds, or 60 seconds to about 2 or 3 weeks or more. Preferably, the contacting step is between about 2, 5, 10, 30, or 45 minutes to about 12, 14, 16, 18, or 20 days. More preferably, the contacting step is between about 1, 3, 5, 8, or 24 hours to about 3, 5, 7, or 10 days.

Furthermore, conditions promoting certain types of cellular proliferation or differentiation can be used during the culture. These conditions include but are not limited to, alteration in temperature, alteration in oxygen/carbon dioxide content, alterations in turbidity of said media, or exposure to small molecules modifiers of cell cultures such as nutrients, inhibitors of certain enzymes, stimulators of certain enzymes, inhibitors of histone deacetylase activity such as valproic acid, trichostatin-A, trapoxin A, or depsipeptide, inhibitors of DNA methyltransferase activity such as 5-azacytidine, inhibitors of the enzyme GSK-3, and the like.

The role of oxygen tension in stem cell self-renewal and viability is also an important issue that is contemplated in the current invention. It is known that hematopoietic stem cells tend to reside in hypoxia niches of the bone marrow and that as cells differentiate into more mature progeny, they progressively migrate to areas of the bone marrow with higher oxygen tension (Ivanovic, et al., 2002, *Exp Hematol* 30:67-73, which is incorporated by reference herein in its entirety). This important variable in tissue culture was exploited in studies showing that superior expansion of human CD34 stem cells capable of full hematopoietic reconstitution of NOD-SCID mice were obtained in hypoxic conditions using oxygen tension as low as 1.5%. Additionally, other stem cells such as neuronal stem cells also appear to be localized in hypoxic niches and expand preferential in low oxygen in vitro conditions as opposed to normal oxygen tension. Furthermore, embryonic stem cells, which grow at similar proliferative rates between normoxia and hypoxia, retain superior ability to form teratomas in vivo and embryoid bodies in vitro when grown under hypoxic conditions. Accordingly, one embodiment of the invention is the use of hypoxic conditions during some or all of the incubation of the stem cells in specialized incubators with an oxygen tension ranging from 0.1% to 7.5%, preferably 0.5% to 5%, more preferably 3%-5%. Additionally, another embodiment of the invention is the use of hypoxic conditions in combination with compositions of the invention in order to enhance proliferation without differentiation of stem cells being grown in culture.

In terms of enhancing the ability of a composition of the invention to stimulate proliferation of stem cells without differentiation, one adjuvant approach that is considered an embodiment of the invention is the use of enzymatic inhibitors in conjunction with a composition of the invention. For example, histone deacetylases are a class of enzymes involved in epigenetically opening parts of chromatin to transcription factors, thus allowing expression of genes that under normal adult conditions would not be expressed. For example, the telomerase gene (catalytic subunit hTERT) is involved in the process of cellular immortalization and is expressed under physiological conditions only in embryonic stem cells, as well as some bone marrow hematopoietic cells, abnormally. The functional role of the telomerase enzyme is to repair the shortened telomeric ends of chromosomes so that cells can escape replicative senescence. Pathologically, telomerase is the enzyme responsible for the ability of cancer cells to proliferate indefinitely in cell culture. Under normal physiological conditions fibroblasts do not express telomerase and undergo replicative senescence. A variety of reports have been published describing that treatment of fibroblasts with histone deacetylase inhibitors such as trichostatin A reinduces expression of functional telomerase (Mukhopadhyay, et al., 2005, *J Cell Mol Med* 9:662-669; Hou, et al., 2002, *Exp Cell Res* 274:25-34; Cong, et al., 2000, *J Biol Chem* 275:35665-35668, each of which is incorporated by reference herein in its entirety). This is suggestive that manipulating the histone deacetylase pathway can be used as a method of de-differentiating cells or offering the possibility of "rejuvenating" progenitors that are nearing replicative exhaustion. Indeed, it was demonstrated that the life extension effect observed due to caloric restriction is connected to the histone deacetylase pathway (Howitz, et al., 2003, *Nature* 425:191-196, which is incorporated by reference herein in its entirety). The clinical relevance of manipulating this pathway is illustrated in experiments with valproic acid, an antidepressant that is in clinical use is a histone deacetylase inhibitor with similar potency to trichostatin A in some models. It was demonstrated that treatment of bone marrow derived hematopoietic stem cells with valproic acid increases both proliferation and self-renewal through accelerating cell cycle progression (Bug, supra). Said acceleration was accompanied by a down-regulation of inhibitor factor p21(cip-1/waf-1). Furthermore, valproic acid treatment suppressed GSK3 activity and activated the Wnt signaling pathway, both of which are associated with self renewal in both hematopoietic (Gotoh, et al., 1997, *Cell Growth Differ* 8:721-729; Baba, et al., 2005, *Immunity* 23:599-609, each of which is incorporated by reference herein in its entirety), but also embryonic (Sato, et al., 2004, *Nat Med* 10:55-63; He, et al., 2005, *Clin Lung Cancer* 7:54-60, each of which is incorporated by reference herein in its entirety) stem cells. The potency of valproic acid to synergize with known hematopoietic stem cell stimulatory cytokines such as Flt3L, TPO, SCF and IL-3 was demonstrated (De Felice, et al., 2005, *Cancer Res* 65:1505-1513, which is incorporated by reference herein in its entirety).

By contact with a composition of the invention, the stem cells are able to increase their growth rate and expand rapidly. When desired, culture conditions are used that allow the compositions of the invention to augment the proliferation of stem cells without induction of differentiation. Any suitable method of determining the growth rate and differentiation of the stem cells can be used to determine the growth rate and cell count of the stem cells so produced. For example, flow cytometry analysis of markers associated with stem cell retention, semisolid media assays for quantification of early and committed progenitors, and in vivo NOD-SCID Repopulating Activity Assays to quantify the number of in vivo stem cells with reconstituting activity. These assays can be modified and altered in order to allow detection of specific stem cell subtypes. Assays can also be developed in immune compromised mice, such as the NOD-SCID strain, by induction of a pathology to which the human stem cells is anticipated to be therapeutic. For example, human stem cells have been demonstrated to possess therapeutic activity in a variety of non-hematopoietic settings in the NOD-SCID, as well as the NUDE mouse. The cell growth rate can also depend on other factors, such as, for example, temperature, type of stem cell, contents of the medium, and the time allowed for the placental incubation step and contacting step. One of skill in the art will be able to alter these variables to adjust the growth rate as needed.

Another embodiment of the invention is the use of compositions, or cell culture media supplemented with the compositions of the present invention, to stimulate proliferation of stem cells, including, for example:

human embryonic stem cells characterized by expression of markers such as SSEA-4, GCTM-2 antigen, TRA 1-60, Cripto, gastrin-releasing peptide (GRP) receptor, podocalyxin-like protein (PODXL), or human telomerase reverse transcriptase (hTERT);

human oocyte producing stem cells characterized by expression of markers such Vasa, Oct-4, Dazl, Stella, Fragilis, Nobox, c-Kit and Sca-1;

parthenogenetically generated stem cells characterized by expression of markers such Oct-4, alkaline phosphatase, telomerase, SSEA-4, TRA 1-60 and TRA 1-81;

spermatogonial stem cells reprogrammed to pluripotent germ-line stem cells characterized by expression of markers such Oct-4, Nanog, Dppa5 and Rex1;

hematopoietic stem cells characterized by markers such as Stem Cell Antigen (SCA+), lineage negative (lin−), c-kit+, CD34+, CD38−, CD33−;

mesenchymal stem cells characterized by markers such as LFA-3, ICAM-1, PECAM-1, P-selectin, L-selectin, CD49b/CD29, CD49c/CD29, CD49d/CD29, CD61, CD18, CD29, 6-19, thrombomodulin, telomerase, CD10, CD13, STRO-1, STRO-2, VCAM-1, CD146, THY-1;

placentally derived multipotent cells characterized by markers such as Oct-4, Rex-1, CD9, CD13, CD29, CD44, CD166, CD90, CD105, SH-3, SH-4, TRA-1-60, TRA-1-81, SSEA-4 and Sox-2;

adipose-derived stem cells characterized by markers such as CD13, CD29, CD44, CD63, CD73, CD90, CD166, Aldehyde dehydrogenase (ALDH), and ABCG2;

cord blood stem cells characterized by markers such as CD34, c-kit, and CXCR-4;

deciduous tooth stem cells characterized by markers such as STRO-1, CD146 (MUC18), alkaline phosphatase, MEPE, and bFGF;

neural stem cells characterized by markers such as RC-2, 3CB2, BLB, Sox-2hh, GLAST, Pax 6, nesting, Muashi-1, and prominin;

stomach epithelial stem cell characterized by markers such as Musashi-1, c-hairy-1 and HES-5;

skeletal muscle stem cell characterized by markers such as desmin positive, SCA-1+, CD45− and possessing a side population profile on flow cytometry by dye exclusion;

mammary gland stem cell characterized by markers such as SCA-1 positive, CD45− and keratin-6;

dermal stem cell characterized by markers such as SCA-1 positive, CD34+, CD45− and positive for alpha6-integrin, beta1-integrin, keratin 14, and keratin 19;

myocardial stem cell characterized by markers such as SCA-1 positive, c-kit positive, and possessing a side population profile on flow cytometry by dye exclusion;

mesangial stem cell characterized by markers such as SCA-1 positive, c-kit positive, and possessing a side population profile on flow cytometry by dye exclusion;

hepatic oval stem cell characterized by markers such as SCA-1 positive, c-kit positive, and CD34 positive; or, pancreatic stem cell characterized by markers such as nestin, CK-8, CK-18, Isl-1, Pdx-1, Pax-4, and Ngn-3.

The compositions of the invention can be used as a stimulator of proliferation alone or as an additive to media known to be useful for culturing said cells. An example of such a tissue culture media is Dulbecco's modified Eagle's medium (DMEM).

Another embodiment of the invention is the use of compositions or cell culture media supplemented with the compositions of the present invention to stimulate proliferation of totipotent stem cells generated by cloning through the use of nuclear transfer technologies.

The methods of administering stem cells to a mammal comprise contacting stem cells with a composition of the invention, cultivating the stem cells under conditions suitable to facilitate the expansion of the stem cells, and introducing the expanded cells into a mammal.

Thus, the serum-free supplement of the present invention can also be used to prepare a stem cell type of interest for explanation into a mammal. In this embodiment, cells which have been caused to differentiate ex vivo are introduced into a mammal. For example, hematopoietic cells which have been caused to differentiate into a hematopoietic stem, precursor, or progenitor cell can be introduced into the bone marrow or the bloodstream of the mammal. The differentiated cells can be introduced into, for example, the bone marrow or bloodstream of the mammal by well-known techniques.

In some embodiments of the invention a method for the expansion or growth of stem cells is provided that includes contacting a stem cell with the a growth medium containing a composition of the invention. The stem cell can be a) a totipotent cell such as an embryonic stem cell, an extra-embryonic stem cell, a cloned stem cell, a parthenogenesis derived cell;

b) a pluripotent cell such as a hematopoietic stem cell, an adipose derived stem cell, a mesenchymal stem cell, a cord blood stem cell, a placentally derived stem cell, an exfoliated tooth derived stem cells, a hair follicle stem cell or a neural stem cell; or c) a tissue specific progenitor cell such as a precursor cell for the neuronal, hepatic, nephrogenic, adipogenic, osteoblastic, osteoclastic, alveolar, cardiac, intestinal, or endothelial lineage.

The incubating step can occur, for example, at a suitable temperature range such as from about 32° C. to about 40° C.

Within these methods, the stem cells can be manipulated during their isolation or production or during their expansion or immediately prior to their administration to a mammal. Such manipulation may tailor the stem cells to perform a therapeutic function following administration to the mammal. For example, mesenchymal bone marrow cells treated with the DNA methyltransferase inhibitor 5-aza-cytidine have been shown to transdifferentiate into myocardial tissue and to improve left ventricular ejection fraction and inhibit cardiac remodeling. Other types of stem cells have been utilized for improvement in myocardial activity, perfusion, and decreasing ventricular remodeling, including mesenchymal stem cells, endothelial stem cells, and skeletal myoblasts. A limiting factor in these studies is the lack of reproducible methods for expanding sufficient numbers of semi-differentiated progenitor stem cells that possess a high proclivity for repairing the heart. This drawback is in part due to lack of proper culture mediums for expansion of such unique cell populations. The compositions and methods of this invention overcome these drawbacks by providing reproducible means of expanding and maintaining stem cell populations for subsequent therapeutic administration to a mammal.

Each publication or patent cited herein is incorporated herein by reference in its entirety.

Mechanism of Action

DA-DKP and in particular, low molecular weight fractions of commercial human serum albumin, such as Ampion™ (Ampio Pharmaceuticals, Greenwood Village, Colo.) has multiple activities that can be categorized as anti-inflammatory and remodeling/healing. The anti-inflammatory properties of Ampion™ involve the inhibition of vascular permeability through cytoskeletal rearrangement in endothelial cells (cortical actin ring formation), inhibition of activation of memory T cells (not Naive) by antiCD3/CD28 or APC and reducing the amount of pro inflammatory cytokines (TNFa) produced by PBMC in response to a strong pro-inflammatory stimulus (LPS). The remodeling/healing effects are through mobilization and differentiation of stem cells into tissue specific cells (such as differentiation into chondrocytes in the case of the knee).

Ampion™ activates the ligand activated transcription factor (TF) Peroxisome Proliferator Activator Receptor (PPAR), possibly through binding to the co-activator site of the molecule in both mesenchymal stem cells and PBMC. TF arrays have demonstrated activation of PPAR and its binding partner Retinoid X Receptor (RXR). PPAR belongs to the nuclear hormone receptor superfamily, expressed in inflammatory and immune cells. PPAR heterodimerizes with the retinoid X receptor (RXR) in the nucleus and together, the dimer binds to the peroxisome proliferation response element (PPRE) in the promoter of the target gene. The genes involved are anti inflammatory, involved in protection of stem cells and differentiation. Four functional domains were identified on PPAR: A/B, C, D and E/F. The N terminal A/B domain contains ligand independent activation function (AF-1), which is responsible for phosphorylation of PPAR. The C domain or DNA binding domain (DBD) promotes the binding of PPAR to the PPRE in the promoter region of the target genes. The D domain is the site of co-factors binding. The E/F domain is the ligand binding domain (LBD) is responsible for ligand specificity and activation of PPAR binding to the PPRE which increases the expression of target genes.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

EXAMPLES

Example 1

A clinical trial was performed to investigate the effect of intra-articular knee injection of the <5000 MW Fraction (also referred to herein as "Ampion™") for improving joint function and reducing the pain of osteoarthritis of the knee in adults with symptomatic primary knee osteoarthritis. A randomized, placebo-controlled, double-blind, parallel study with 43 evaluable subjects was chosen as the appropriate design to estimate the treatment effect and safety of the <5000 MW Fraction when it was injected into the study knee.

Study Drug 2 arms; each subject received a single 4 ml injection in one knee with one of either Amipon™ or saline.

Study Population

The study population was 43 patient, male or female 40-83 years old (average 63.0, standard deviation (SD) 9.6) 28 were male and 15 were female. All subjects were Caucasian. The subjects' height ranged from 162 to 192 cm (average 175.3, SD 8.1) with weight at screening ranging from 56 to 117 kg (average 88.8, SD 13.89). The subjects were fully ambulatory, with symptomatic primary knee osteoarthritis for more than 6 months prior to screening with Kellgren Lawrence Grade II or III (indicating mild or moderate osteoarthritis). Grade II for 6 subjects and Grade III for 36 subjects. One subject did have Grade IV. If both knees of a subject were osteroarthritic, one knee was selected for study while the other knee received standard of care.

Exclusion Criteria:

The following is the exclusion criteria for the study population:
1. Unfit as a result of medical review and screening investigation
2. A history of allergic reactions to albumin
3. A history of allergic reactions to excipients in 5% human albumin
4. Any intra-articular or local periarticular injection, injection or surgery to the index knee (previous 6 months)
5. Operative arthroscopy (previous 3 months)
6. Surgical procedure to the index knee other than arthroscopy (previous 12 months)
7. Any investigational knee products (previous 12 months)
8. Kellgren Lawrence Grade I or IV (doubtful or severe) osteoarthritis of the knee.
9. Inflammatory or crystal arthropathies, acute fractures, severe loss of bone density, bone necrosis.
10. Isolated patella-femoral syndrome or chondromalacia.
11. Any other disease or condition interfering with the free use and evaluation of the index knee
12. Major injury to the index (previous 12 months)
13. Severe hip osteoarthritis ipsilateral to the index knee.
14. Any pain that could interfere with the assessment of index knee pain
15. Any pharmacological or non-pharmacological treatment started or changed (previous 4 weeks)
16. Use of a. any topical treatment (previous 48 h) b. All analgesics and NSAIDs except paracetamol (previous 48 h), c. Anticoagulant therapy (previous 48 h) d. Any systemic steroid treatments (previous 14 days), e. All immunosuppressives within a period of 5 times the drug's half life prior to randomization, f corticosteroids >10 mg prednisolone equivalent per day (previous 30 days), g. Any albumin treatment (previous 3 months)
17. Female subjects who are pregnant or lactating.
18. Female subjects of childbearing potential who have a positive pregnancy test on Day 1 prior to treatment.

Study Assessment

The study consisted of a three week screening period and an 84 day study participation period. Follow-up assessments were performed at 6 hours, 24 hours and 72 hours post injection. Subjects were contact by telephone at Day 8, Day 30 and Day 84 to evaluate overall pain and mobility and to monitor adverse events. The subjects were offered the option of intra-articular betamethasone injection to the investigative knee for pain relief after Day 8, if deemed necessary following an assessment by the investigator.

Primary Outcome

The pain numerical rating scale (NRS) in the study knee was completed at pre-dose (pre-injection baseline), 6 hours post-dose on Day 1, 24 hours post-dose on Day 2, 72 hours post-dose on Day 4, and at Day 8, Day 30 and Day 84 post-dose (EOS or End-of-study). The pain NRS is a numerical rating of 0-10, with 0 being no pain, 5 being moderate pain and 10 being worst possible pain.

Safety Endpoints

The safety endpoints of the study were incidence of adverse events, vital signs at pre-dose and study Day 4, twelve lead ECG readings at screening and 24 hours post-dose, and clinical blood safety tests (biochemical and hematology) assessed at screening and 24 hours post-dose.

Secondary Endpoints

The secondary endpoints of the study were percent responders at Day 30 and Day 84, defined as an improvement in pain NRS of 2 or more points, the change from pre-injection baseline in WOMAC Osteoarthritis Index 3.1 (complete scale, pain subscore, stiffness subscore and function subscore) at 24 and 72 hours after intra-articular injection, the change from pre-injection baseline for requirement for rescue medications (paracetamol) to 24 hours and 72 hours after intra-articular injection and changes over time in mobility at Day 8, Day 30 and Day 84 post-dose compared with pre-dose and the immediate post-dose period.

Intent to Treat (ITT) and Safety Population

Study participants who were randomized and received at least one dose of the study medication. ITT refers to subjects that met inclusion/exclusion criteria.

Per Protocol Population

Study participants in the ITT set whose pre-dose pain score did not violate inclusion/exclusion criteria.

Efficacy Population

Study participants in the pre-protocol population who did not receive rescue medication between 8 and 30 days.

Statistical Analyses

Primary: Analysis of covariance (ANCOVA) model to examine the mean (SD) difference between treatment groups for mean change in pain at Day 30 and Day 84 (EOS), adjusted for baseline pain NRS.

Additional: $X^2$ test for differences in percent responders. Cochran-armitage trend test for differences in clinically significant improvements. Student's t-test: mean (SD) difference in pain NRS at 30 days.

Safety Analysis:

Adverse events and serious adverse events were listed by subject. Summaries were presented by treatment of adverse events classified by MedDRA System Organ Class and Preferred Term, for overall incidence and by severity and relationship to study medication. Incidence of treatment-emergent adverse events were compared between treatment groups. All clinical safety and tolerability data was listed for each subject and summarized by treatment. Vital signs and ECG parameters were tabulated and summarized by treatment. Laboratory values were listed, along with comments as to clinical significance for values outside the laboratory's normal ranges. Changes from screening were assessed for clinical significance.

Results:

TABLE 4

| Analysis Set | Population | | |
|---|---|---|---|
| | Study Size (n) | Ampion ™ (n) | Saline (n) |
| Safety Set | 43 | 22 | 21 |
| ITT Set | 43 | 22 | 21 |
| Per-protocol Set[a] | 41 | 20 | 21 |
| Efficacy evaluable Set[b] | 32 | 17 | 15 |

[a]2 subjects in the Ampion ™ group had baseline pain NRS <4 points
[b]5 subjects in the Ampion ™ group and 6 subjects in the saline group required rescue medication Use of Rescue Medications Betamethasone injection: there was no apparent difference between the use of betamethasone injections between subjects who received Ampion™ (5 of 22 subjects, 23%) compared with subjects who received saline (6 of 21 subjects, 29%).

Rescue medications (paracetamol): rescue medication for pain relief in the study knee within 24 hours of injection occurred in a similar number of subjects receiving Ampion™ (6 of 22 subjects) compared with subjects receiving saline (6 of 21 subjects), with similar mean doses of paracetamol used in each of the treatment groups.

Efficacy Results:

TABLE 5

Pain NRS by treatment, mean (SD) pre-protocol population:

| | Treatment | | | | | | |
|---|---|---|---|---|---|---|---|
| | Pre-dose | 6 h Post dose | 24 h Post dose | 72 h Post dose | Day 8 Post dose | Day 30 Post dose | Day 84 Post dose |
| Ampion ™ | 4.70 (0.7) | 2.00 (1.3) | 3.20 (1.5) | 2.60 (2.1) | 2.90 (2.1) | 2.90 (1.8) | 3.21 (1.8) |
| Saline | 5.29 (1.4) | 2.67 (1.9) | 3.00 (1.7) | 2.86 (2.1) | 3.33 (1.9) | 3.86 (2.2) | 4.81 (2.3) |

TABLE 6

Least Squares (LS) Mean Change in Pain NRS: per-protocol population

| | Treatment | | | | | |
|---|---|---|---|---|---|---|
| | 6 h Post dose | 24 h Post dose | 72 h Post dose | Day 8 Post dose | Day 30 Post dose | Day 84 Post dose |
| D (Ampion ™) | −3.06 | −1.69 | −2.31 | −2.00 | −2.16 | −1.60 |
| E (Saline) | −2.28 | −2.11 | −2.22 | −1.76 | −1.09 | −0.36 |
| P value | 0.15 | 0.42 | 0.89 | 0.71 | 0.12 | 0.07 |

Scale: −10 = largest possible improvement in pain from baseline, 10 = smallest possible improvement (largest increase) in pain from baseline.
Day 1: 6 hours post-dose
*adjusted for baseline pain NRS

TABLE 7

LS Mean Change in Pain NRS: efficacy evaluable population

| | Treatment | | | | | |
|---|---|---|---|---|---|---|
| | 6 h Post dose | 24 h Post dose | 72 h Post dose | Day 8 Post dose | Day 30 Post dose | Day 84 Post dose |
| D (Ampion ™) | −2.91 | −1.99 | −2.94 | −2.45 | −2.29 | −2.22 |
| E (Saline) | −2.62 | −2.61 | −2.79 | −2.22 | −1.17 | −0.46 |
| P value | 0.62 | 0.19 | 0.79 | 0.71 | 0.19 | 0.04 |

Scale: −10 = largest possible improvement in pain from baseline 10 = smallest possible improvement (largest increase) in pain from baseline.
Day 1: 6 hours post-dose
*adjusted for baseline pain NRS Percent responders at Day 84 (EOS): per-protocol population (see Table 8)
Responder: decrease in Day 84 pain NRS of −2 to −10 points (with −10 being the largest possible improvement in pain).
Non-responder: decrease in pain at Day 84 of −1 to 10 (with 10 being the largest possible increase in pain).

TABLE 8

Trends in pain at 30 days from baseline, by treatment group:

| Treatment | Non-Responder | Responder | P value |
|---|---|---|---|
| Ampion ™ | 47.4% | 52.6% | 0.06 |
| Saline | 76.2% | 23.8% | |

Percent responders at Day 84 (EOS): efficacy evaluable population (see Table 9)
Responder: decrease in Day 84 pain NRS of −2 to −10 points (with −10 being the largest possible improvement in pain).
Non-responder: decrease in pain at Day 84 of −1 to 10 points (with 10 being the largest possible increase in pain).

TABLE 9

Trends in pain at 30 days from baseline, by treatment group:

| Treatment | Non-Responder | Responder | P value |
|---|---|---|---|
| Ampion ™ | 35.7% | 64.3% | 0.10 |
| Saline | 66.7% | 33.3% | |

Summary of Findings: Efficacy:

Overall pain (as assessed by the pain numerical rating score) and WOMAC scores were reduced post-dose for each of the treatment groups for the duration of the study (p<0.05), except placebo at Day 84. In addition, there was a trend in a significant difference between changes from baseline at Day 30 and at Day 84 for subjects who received Ampion™ compared to subjects who received saline placebo (Day 30: p=0.12; Day 84: p=0.07). This trend became statistically significant in subjects who did not receive rescue medication (p=0.04). There was a trend towards a higher percentage of responders at the end of the study (Day 84) for subjects receiving Ampion™ vs. Placebo (p=0.06). Use of paracetamol rescue medication up to 72 hours post-dose was highest in the Treatment E group (saline). See FIG. 1.

Adverse Events (AEs)

Treatment-emergent AEs were reported for 20 of the 43 subjects (47%) following dose administration, with a total of 27 AEs. Commonly occurring AEs were headache and joint swelling and stiffness in the knee. Most subjects reported AEs classified as mild only (16 of 43 subjects, 37%). Only 4 subjects (9%) reported AEs of moderate severity:

Ampion™: Joint injury and hypertension

Saline: Back pain and vessel puncture site haematoma

There were no apparent differences in the incidence of moderate AEs between subjects who received Ampion™ (2 subjects, 9%) compared with subjects who received saline (2 subjects, 10%). These AEs were all deemed to be probably not or definitely not related to study drug.

There were no AEs classified as severe.

AEs deemed to be related to study drug administration (possibly) were reported in 3 of 43 subjects (7%). There were no apparent differences in the incidence of related AEs between subjects who received Ampion™ (1 subject, 5%) compared with subjects who received saline (2 subjects, 10%):

a. Headache of mild severity which commenced 5 minutes after treatment administration and resolved 1.8 hours later (Ampion™)

b. Headache of mild severity which commenced 5 hours after treatment administration and resolved 0.5 hours later (saline)

c. Joint swelling of right knee (study knee) of mild severity which commenced 2.4 days after treatment administration and resolved 21 hours later (saline)

Overall, a higher proportion of treatment-emergent AEs were reported in subjects who received saline (12 subjects, 57%) compared with subjects who received Ampion™ (8 subjects, 36%). AEs deemed to be related to study drug administration (possibly) were reported in 3 of 43 subjects (7%) and included headache and joint swelling of the knee. There were no deaths or other serious AEs. There were no clear differences in safety as assessed by biochemistry clinical laboratory tests, vital signs, and ECG assessments between treatments.

Conclusions of Study:

Pain (as assessed by the pain numerical rating score) and WOMAC scores were reduced post-dose for each of the treatment groups for the duration of the study, except placebo at Day 84, with no significant differences between treatment groups. Despite a higher baseline pain NRS for the saline group compared to the Ampion™ group, there was a trend towards a long-term effect of study drug, with a higher percentage of subjects who responded at Day 84 for Ampion™ compared to saline. In subjects receiving Ampion™, overall pain was reduced post-dose for the duration of the study, whereas subjects receiving saline did not have a reduction in pain post-dose at Day 84. Use of paracetamol rescue medication up to 72 hours post-dose was highest in the Treatment E group (saline). Ampion™ was considered safe and well tolerated at the dose used in the study. Improvement in pain in this study at day 84 is consistent with regeneration of tissue caused by the administration of Ampion™.

Example 2

This example demonstrates the enhancement of stem cell chondrogenesis by DADKP and other drug treatments.

The inventors investigated the possibility that DADKP directly enhances chondrogenesis or has an additive or synergistic effect on the transcription and/or translation of genes important for the chondrocyte lineage.

Materials:

Stem Cells: Bone marrow derived human mesenchymal stem cells: Passage 5 Bone marrow derived human mesenchymal stem cells (HUXMA-01001, Cyagen Biosciences, Sunnyvale Calif.)

Mesenchymal Stem Cell Chondrogenic Differentiation medium (GUXMX-90041, Cyagen Biosciences, Sunnyvale Calif.)

TheraPEAK MSCGM chemically defined Stem cell medium (190632 Lonza)

1 mM Dexamethasone acetate and mifepristone in absolute ethanol (Sigma)

Saline or 0.9% Sodium chloride for injection ZR Flush (Excelsior Medical, Neptune N.J.)

Sterile filtered 0.6 mM sodium caprylate in saline (sigma)

Sterile filtered 3 mM NAT in saline (sigma); To prepare, heat at 60° C. for 30 minutes then sonicate for 5 minutes.

Sterile filtered 10 mM DADKP in saline 0.2 µM syringe filters

Hepes buffered saline, Trypsin/EDTA, Trypsin neutralizing solution (Lonza reagent pack)

182 cm2 tissue culture flasks pipettes and sterile tips

Tissue culture hood, humidified CO2 incubator, water or bead bath 24 well tissue culture plates Qiagen RNeasy plus spin columns (Qiagen 74134)

Qiagen RT2 qPCR primer pairs for Collagen 2A1, MMP13, TIMP1, Aggrecan, GAPDH, and Actin B Roche Sybr green I master mix and Invitrogen Superscript VILO master mix.

Roche 480 lightcycler

The following stock drug treatment solutions were prepared in saline for injection and warmed to 37° C. in bath:

4 µM dexamethasone

4 µM mifepristone 3 mM NAT 0.6 mM caprylate

80 µM DADKP

Mix of 3 mM NAT, 0.6 mM caprylate, 80 µM DADKP ("Ampion" mix)

Cyagen Chondrogenic Differentiation medium was prepared by manufacturer protocols but excluding dexamethasone and TGF beta 3 supplements, and warmed to 37° C. in bath.

The treatment protocol included expanding 5 HUXMA stem cells in 182 cm$^2$ flasks containing 40 mls Thera-PEAK™ MSCGM to 80-90% confluence. Cells were trypsinized from the flasks and a 1.0×10$^7$ cell suspension of HUXMA stem cells was warmed in Cyagen Chondrogenic Differentiation medium. 20 µl of warmed cell suspension was spotted in the middle of each well of a 24-well tissue culture plate (200,000 cells per spot), and incubated at 37° C. and 5% $CO_2$ for one hour.

The plates were removed from the incubator and an additional 720 µl chondrogenic medium was added to each well. 250 µl saline, or drug solutions were added to the appropriate wells in triplicate (bringing the final drug dilution to one-quarter of the stock drug treatment solution concentrations). 10 µl of TGF beta 3 solution (supplied by Cyagen) was added to each well, and the plates were returned to the incubator.

Medium exchanges were performed every 3-4 days by aspirating the medium from the wells and replacing with fresh chondrogenic medium, diluted stocks, and TGF beta 3, as described above.

RNA isolation and analysis was conducted for all plates as follows at days 7, 14, and 22 post treatment (with the described medium exchanges). Medium from the wells was removed and saved for further protein analysis. Qiagen RNeasy plus lysis buffer (with 2mercaptoethanol) was added to each well and gently shaken for 10 minutes. The lysed cell suspensions from each well were transferred to Qiashredder columns and spun at 14,000 rpm for 2 minutes. RNA isolation proceeded by RNeasy™ plus manufacturer's protocol. RNA was eluted from the Qiagen columns using 25 µl RNase free water.

cDNA synthesis and real time PCR was conducted as follows. First strand synthesis of cDNA from all samples was performed in 20 µl total volume using 10 µl isolated RNA. All cDNA reactions were then diluted with 30 µl nuclease free water. Real time PCR was then performed using 5 µl diluted cDNA, Roche Syber green master mix, and Qiagen RT$^2$ gPCR™ primer pairs in 20 µl total reaction volume. Relative gene expression was determined by delta deta Ct method.

Data/Results:

TABLE 10

Day 7 results:
130515 Gene expression RTPCR

| Sample | Cp Coll | Cp Actin | ΔCp | Mean ΔCp | ΔΔCp vs saline | $2^{-\Delta\Delta Cp}$ vs saline | regulation | Mean regulation | std regulation |
|---|---|---|---|---|---|---|---|---|---|
| Collagen 2A1 Saline | 35.5 | 28.71 | 6.79 | 6.733 | | | | | |
| | 35.82 | 28.35 | 7.47 | | | | | | |
| | 34.62 | 28.68 | 5.94 | | | | | | |
| Collagen 2A1 Dexamethasone | 32.42 | 25.67 | 6.75 | 5.797 | 0.017 | 0.9885 | −1.01 | 1.44 | 2.1229 |
| | 32.42 | 27.07 | 5.35 | | −1.38 | 2.6087 | 2.61 | | |
| | 33.41 | 28.12 | 5.29 | | −1.44 | 2.7195 | 2.72 | | |
| Collagen 2A1 Mifepristone | 33.67 | 26.77 | 6.9 | 7.433 | 0.167 | 0.8909 | −1.12 | −1.82 | 1.1179 |
| | 32.73 | 24.36 | 8.37 | | 1.637 | 0.3216 | −3.11 | | |
| | 34.82 | 27.79 | 7.03 | | 0.297 | 0.8141 | −1.23 | | |
| Collagen 2A1 Ampion | 31.34 | 27.08 | 4.26 | 4.15 | −2.47 | 5.5533 | 5.55 | 6.46 | 3.1219 |
| | 33.5 | 28.73 | 4.77 | | −1.96 | 3.8996 | 3.90 | | |
| | 31.94 | 28.52 | 3.42 | | −3.31 | 9.9406 | 9.94 | | |
| Collagen 2A1 NAT | 34.84 | 27.62 | 7.22 | 7.063 | 0.487 | 0.7137 | −1.40 | −0.61 | 1.4003 |
| | 33.83 | 27.11 | 6.72 | | −0.01 | 1.0093 | 1.01 | | |
| | 34.09 | 26.84 | 7.25 | | 0.517 | 0.699 | −1.43 | | |
| Collagen 2A1 Caprylate | 33.77 | 27.74 | 6.03 | 6.573 | −0.7 | 1.6283 | 1.63 | −0.18 | 1.5643 |
| | 33.95 | 27.14 | 6.81 | | 0.077 | 0.9482 | −1.05 | | |
| | 33.94 | 27.06 | 6.88 | | 0.147 | 0.9033 | −1.11 | | |
| Collagen 2A1 DADKP | 32.82 | 26.81 | 6.01 | 6.993 | −0.72 | 1.651 | 1.65 | −0.62 | 2.0361 |
| | 34.44 | 26.52 | 7.92 | | 1.187 | 0.4393 | −2.28 | | |
| | 32.87 | 25.82 | 7.05 | | 0.317 | 0.8029 | −1.25 | | |
| Collagen 2A1 Mix | 32.57 | 26.67 | 5.9 | 6.6 | −0.83 | 1.7818 | 1.78 | −0.18 | 1.7056 |
| | 33.8 | 26.98 | 6.82 | | 0.087 | 0.9417 | −1.06 | | |
| | 33.45 | 26.37 | 7.08 | 7.08 | 0.347 | 0.7864 | −1.27 | | |
| MMP13 Saline | 32.64 | 28.71 | 3.93 | 4.637 | | | | | |
| | 33.19 | 28.35 | 4.84 | | | | | | |
| | 33.82 | 28.68 | 5.14 | | | | | | |
| MMP13 Dexamethasone | 31 | 25.67 | 5.33 | 4.493 | 0.693 | 0.6184 | −1.62 | 0.45 | 1.7977 |
| | 30.99 | 27.07 | 3.92 | | −0.72 | 1.6434 | 1.64 | | |
| | 32.35 | 28.12 | 4.23 | | −0.41 | 1.3256 | 1.33 | | |
| MMP13 Mifepristone | 31.98 | 26.77 | 5.21 | 5.7 | 0.573 | 0.6721 | −1.49 | −2.47 | 1.8254 |
| | 31.19 | 24.36 | 6.83 | | 2.193 | 0.2186 | | | |
| | 32.85 | 27.79 | 5.06 | | 0.423 | 0.7457 | −1.34 | | |
| MMP13 Ampion | 30.53 | 27.08 | 3.45 | 3.36 | −1.19 | 2.2763 | 2.28 | 2.59 | 1.1875 |
| | 32.69 | 28.73 | 3.96 | | −0.68 | 1.5984 | 1.60 | | |
| | 31.19 | 28.52 | 2.67 | | −1.97 | 3.9086 | 3.91 | | |
| MMP13 NAT | 32.77 | 27.62 | 5.15 | 5.523 | 0.513 | 0.7006 | −1.43 | −1.89 | 0.5175 |
| | 32.6 | 27.11 | 5.49 | | 0.853 | 0.5535 | −1.81 | | |
| | 32.77 | 26.84 | 5.93 | | 1.293 | 0.408 | −2.45 | | |
| MMP13 Caprylate | 33.77 | 27.74 | 6.03 | 5.623 | 1.393 | 0.3807 | −2.63 | −1.55 | 2.2483 |
| | 31.73 | 27.14 | 4.59 | | −0.05 | 1.0329 | 1.03 | | |
| | 33.31 | 27.06 | 6.25 | | 1.613 | 0.3268 | −3.06 | | |

TABLE 10-continued

Day 7 results:
130515 Gene expression RTPCR

| Sample | Cp Coll | Cp Actin | ΔCp | Mean ΔCp | ΔΔCp vs saline | $2^{-\Delta\Delta Cp}$ vs saline | regulation | Mean regulation | std regulation |
|---|---|---|---|---|---|---|---|---|---|
| MMP13 DADKP | 31.81 | 26.81 | 5 | 5.017 | 0.363 | 0.7774 | −1.29 | −0.67 | 1.4896 |
| | 31.12 | 26.52 | 4.6 | | −0.04 | 1.0257 | 1.03 | | |
| | 31.27 | 25.82 | 5.45 | | 0.813 | 0.5691 | −1.76 | | |
| MMP13 Mix | 31.21 | 26.67 | 4.54 | 5.323 | −0.1 | 1.0693 | 1.07 | −1.10 | 1.9647 |
| | 32.31 | 26.98 | 5.33 | | 0.693 | 0.6184 | −1.62 | | |
| | 32.47 | 26.37 | 6.1 | | 1.463 | 0.3627 | −2.76 | | |

At day seven, the inventors observed elevated collagen type 2A1 and MMP13 expression. All cultures were in discs except the DADKP-treated wells are pulled into loose pellets. Pictures of cell aggregates were taken at day 8 post treatment (See FIG. 2).

TABLE 11

Day 14 results:
130521 Gene expression RTPCR

| Sample | Cp Coll | Cp Actin | ΔCp | Mean ΔCp | ΔΔCp vs saline | $2^{-\Delta\Delta Cp}$ vs saline | regulation | Mean regulation | std regulation |
|---|---|---|---|---|---|---|---|---|---|
| Collagen 2A1 Saline | 29.3 | 16.51 | 12.79 | 11.06 | | | | | |
| | 27.99 | 17.59 | 10.4 | | | | | | |
| | 27.35 | 17.37 | 9.98 | | | | | | |
| Collagen 2A1 Dexamethasone | 22.58 | 14.39 | 8.19 | 8.07 | −2.87 | 7.2938 | 7.29 | 8.08 | 2.0259 |
| | 22.58 | 14.9 | 7.68 | | −3.38 | 10.387 | 10.39 | | |
| | 22.85 | 14.51 | 8.34 | | −2.72 | 6.5735 | 6.57 | | |
| Collagen 2A1 Mifepristone | 27.52 | 16.74 | 10.78 | 10.72 | −0.28 | 1.2114 | 1.21 | 1.28 | 0.2556 |
| | 26.77 | 15.81 | 10.96 | | −0.1 | 1.0693 | 1.07 | | |
| | 27.31 | 16.9 | 10.41 | | −0.65 | 1.5655 | 1.57 | | |
| Collagen 2A1 Ampion | 26.87 | 16.58 | 10.29 | 10.91 | −0.77 | 1.7013 | 1.70 | 0.40 | 2.4416 |
| | 26.7 | 16.58 | 10.12 | | −0.94 | 1.9141 | 1.91 | | |
| | 28.7 | 16.37 | 12.33 | | 1.273 | 0.4137 | −2.42 | | |
| Collagen 2A1 NAT | 29.41 | 16.58 | 12.83 | 9.72 | 1.773 | 0.2925 | −3.42 | 3.81 | 6.2716 |
| | 25.69 | 17.46 | 8.23 | | −2.83 | 7.0943 | 7.09 | | |
| | 24.51 | 16.41 | 8.1 | | −2.96 | 7.7633 | 7.76 | | |
| Collagen 2A1 Caprylate | 25.88 | 17.67 | 8.21 | 8.477 | −2.85 | 7.1934 | 7.19 | 6.14 | 1.6176 |
| | 24.6 | 16.34 | 8.26 | | −2.8 | 6.9483 | 6.95 | | |
| | 25.75 | 16.79 | 8.96 | | −2.1 | 4.2772 | 4.28 | | |
| Collagen 2A1 DADKP | 28.86 | 18.37 | 10.49 | 10.43 | −0.57 | 1.4811 | 1.48 | 1.01 | 1.8387 |
| | 27.3 | 17.6 | 9.7 | | −1.36 | 2.5609 | 2.56 | | |
| | 27.64 | 16.55 | 11.09 | | 0.033 | 0.9772 | −1.02 | | |
| Collagen 2A1 Mix | 28.5 | 16.47 | 12.03 | 10.05 | 0.973 | 0.5093 | −1.96 | 2.00 | 3.4307 |
| | 24.97 | 15.93 | 9.04 | | −2.02 | 4.0465 | 4.05 | | |
| | 27.33 | 18.24 | 9.09 | 9.09 | −1.97 | 3.9086 | 3.91 | | |
| cells in pellet | | | | | | | | | |
| cells with nodules | | | | | | | | | |
| SOX9 Saline | 24.94 | 16.51 | 8.43 | 7.18 | | | | | |
| | 24.31 | 17.59 | 6.72 | | | | | | |
| | 23.76 | 17.37 | 6.39 | | | | | | |
| SOX9 Dexamethasone | 22.6 | 14.39 | 8.21 | 7.91 | 1.03 | 0.4897 | −2.04 | −1.69 | 0.4119 |
| | 22.39 | 14.9 | 7.49 | | 0.31 | 0.8066 | −1.24 | | |
| | 22.54 | 14.51 | 8.03 | | 0.85 | 0.5548 | −1.80 | | |
| SOX9 Mifepristone | 23.61 | 16.74 | 6.87 | 6.927 | −0.31 | 1.2397 | 1.24 | 1.19 | 0.0411 |
| | 22.76 | 15.81 | 6.95 | | −0.23 | 1.1728 | 1.17 | | |
| | 23.86 | 16.9 | 6.96 | | −0.22 | 1.1647 | 1.16 | | |
| SOX9 Ampion | 24.87 | 16.58 | 8.29 | 8.357 | 1.11 | 0.4633 | −2.16 | −2.30 | 0.5316 |
| | 25.29 | 16.58 | 8.71 | | 1.53 | 0.3463 | −2.89 | | |
| | 24.44 | 16.37 | 8.07 | | 0.89 | 0.5396 | −1.85 | | |
| SOX9 NAT | 24.96 | 16.58 | 8.38 | 6.877 | 1.2 | 0.4353 | −2.30 | 0.62 | 2.5264 |
| | 23.56 | 17.46 | 6.1 | | −1.08 | 2.114 | 2.11 | | |
| | 22.56 | 16.41 | 6.15 | | −1.03 | 2.042 | 2.04 | | |
| SOX9 Caprylate | 24.64 | 17.67 | 6.97 | 6.383 | −0.21 | 1.1567 | 1.16 | 1.81 | 0.5832 |
| | 22.53 | 16.34 | 6.19 | | −0.99 | 1.9862 | 1.99 | | |
| | 22.78 | 16.79 | 5.99 | | −1.19 | 2.2815 | 2.28 | | |
| SOX9 DADKP | 26.22 | 18.37 | 7.85 | 7.323 | 0.67 | 0.6285 | −1.59 | 0.19 | 1.5462 |
| | 24.68 | 17.6 | 7.08 | | −0.1 | 1.0718 | 1.07 | | |
| | 23.59 | 16.55 | 7.04 | | −0.14 | 1.1019 | 1.10 | | |

TABLE 11-continued

Day 14 results:
130521 Gene expression RTPCR

| Sample | Cp Coll | Cp Actin | ΔCp | Mean ΔCp | ΔΔCp vs saline | $2^{-\Delta\Delta Cp}$ vs saline | regulation | Mean regulation | std regulation |
|---|---|---|---|---|---|---|---|---|---|
| SOX9 Mix | 24.4 | 16.47 | 7.93 | 7.053 | 0.75 | 0.5946 | −1.68 | 0.43 | 1.8251 |
| | 22.54 | 15.93 | 6.61 | | −0.57 | 1.4845 | 1.48 | | |
| | 24.86 | 18.24 | 6.62 | | −0.56 | 1.4743 | 1.47 | | |

At day fourteen, the inventors observed some cultures exhibiting different phenotypes. Comparison of the DADKP-treated wells with the control in a pellet indicated that transcription was still elevated. Additional drug treatments appear to have an effect on collagen transcription.

TABLE 12

Day 22 results:
130529 Gene expression RTPCR

| Sample | Cp Coll | Cp GAPDH | ΔCp | Mean ΔCp | ΔΔCp vs saline | $2^{-\Delta\Delta CP}$ vs saline | regulation | Mean regulation | std regulation |
|---|---|---|---|---|---|---|---|---|---|
| Collagen 2A1 Saline | 31.83 | 18.36 | 13.47 | 13.15 | | | | | |
| | 32.21 | 18.54 | 13.67 | | | | | | |
| | 30.25 | 17.95 | 12.3 | | | | | | |
| Collagen 2A1 Dexamethasone | 22.42 | 16.42 | 6 | 5.76 | −7.15 | 141.7 | 141.70 | 168.82 | 27.286 |
| | 21.94 | 16.41 | 5.53 | | −7.62 | 196.27 | 196.27 | | |
| | 21.42 | 15.67 | 5.75 | | −7.4 | 168.51 | 168.51 | | |
| Collagen 2A1 Mifepristone | 25.99 | 17.47 | 8.52 | 9.22 | −4.63 | 24.704 | 24.70 | 16.82 | 8.3693 |
| | 27.6 | 17.46 | 10.14 | | −3.01 | 8.0371 | 8.04 | | |
| | 26.84 | 17.84 | 9 | | −4.15 | 17.712 | 17.71 | | |
| Collagen 2A1 Ampion | 21.42 | 18.45 | 2.97 | 2.233 | −10.2 | 1157.4 | 1157.40 | 2077.99 | 938.43 |
| | 21.3 | 19.15 | 2.15 | | −11 | 2043.3 | 2043.27 | | |
| | 20.57 | 18.99 | 1.58 | | −11.6 | 3033.3 | 3033.29 | | |
| Collagen 2A1 NAT | 24.2 | 19.45 | 4.75 | 5.207 | −8.4 | 337.01 | 337.01 | 262.94 | 105.86 |
| | 23.63 | 18.76 | 4.87 | | −8.28 | 310.12 | 310.12 | | |
| | 24.67 | 18.67 | 6 | | −7.15 | 141.7 | 141.70 | | |
| Collagen 2A1 Caprylate | 22.93 | 16.85 | 6.08 | 6.557 | −7.07 | 134.05 | 134.05 | 101.18 | 36.373 |
| | 25.6 | 18.41 | 7.19 | | −5.96 | 62.106 | 62.11 | | |
| | 24.26 | 17.86 | 6.4 | | −6.75 | 107.39 | 107.39 | | |
| Collagen 2A1 DADKP | 27.41 | 17.52 | 9.89 | 7.223 | −3.26 | 9.5577 | 9.56 | 136.83 | 170.14 |
| | 25.44 | 18.44 | 7 | | −6.15 | 70.849 | 70.85 | | |
| | 22.94 | 18.16 | 4.78 | | −8.37 | 330.08 | 330.08 | | |
| Collagen 2A1 Mix | 20.54 | 17.93 | 2.61 | 4.03 | −10.5 | 1485.4 | 1485.43 | 723.78 | 661.47 |
| | 22.61 | 17.66 | 4.95 | | −8.2 | 293.39 | 293.39 | | |
| | 21.87 | 17.34 | 4.53 | 4.53 | −8.62 | 392.53 | 392.53 | | | cells in pellet
cells with nodules

| Sample | Cp Coll | Cp GAPDH | ΔCp | Mean ΔCp | ΔΔCp vs saline | 2-ΔΔCP vs saline | regulation | Mean regulation | std regulation |
|---|---|---|---|---|---|---|---|---|---|
| MMP13 Saline | 21.77 | 18.36 | 3.41 | 2.993 | | | | | |
| | 21.37 | 18.54 | 2.83 | | | | | | |
| | 20.69 | 17.95 | 2.74 | | | | | | |
| MMP13 Dexamethasone | 20.77 | 16.42 | 4.35 | 4.433 | 1.357 | 0.3905 | −2.56 | −2.73 | 0.4255 |
| | 20.68 | 16.41 | 4.27 | | 1.277 | 0.4121 | −2.42 | | |
| | 20.35 | 15.67 | 4.68 | | 1.687 | 0.3106 | −3.22 | | |
| MMP13 Mifepristone | 20.98 | 17.47 | 3.51 | 3.633 | 0.517 | 0.699 | −1.43 | −1.57 | 0.2212 |
| | 21.32 | 17.46 | 3.86 | | 0.867 | 0.5484 | −1.82 | | |
| | 21.37 | 17.84 | 3.53 | | 0.537 | 0.6894 | −1.45 | | |
| MMP13 Ampion | 21.18 | 18.45 | 2.73 | 2.96 | −0.26 | 1.2002 | 1.20 | 0.35 | 1.5169 |
| | 21.82 | 19.15 | 2.67 | | −0.32 | 1.2512 | 1.25 | | |
| | 22.47 | 18.99 | 3.48 | | 0.487 | 0.7137 | −1.40 | | |
| MMP13 NAT | 22.68 | 19.45 | 3.23 | 3.053 | 0.237 | 0.8487 | −1.18 | 0.29 | 1.2691 |
| | 21.71 | 18.76 | 2.95 | | −0.04 | 1.0305 | 1.03 | | |
| | 21.65 | 18.67 | 2.98 | | −0.01 | 1.0093 | 1.01 | | |
| MMP13 Caprylate | 20.28 | 16.85 | 3.43 | 2.733 | 0.437 | 0.7388 | −1.35 | 0.62 | 1.7897 |
| | 20.31 | 18.41 | 1.9 | | −1.09 | 2.1337 | 2.13 | | |
| | 20.73 | 17.86 | 2.87 | | −0.12 | 1.0892 | 1.09 | | |
| MMP13 DADKP | 20.34 | 17.52 | 2.82 | 2.96 | −0.17 | 1.1277 | 1.13 | 0.36 | 1.2375 |
| | 21.41 | 18.44 | 2.97 | | −0.02 | 1.0163 | 1.02 | | |
| | 21.25 | 18.16 | 3.09 | | 0.097 | 0.9352 | −1.07 | | |

TABLE 12-continued

Day 22 results:
130529 Gene expression RTPCR

| | | | | | | | | | |
|---|---|---|---|---|---|---|---|---|---|
| MMP13 Mix | 20.78 | 17.93 | 2.85 | 3.287 | −0.14 | 1.1045 | 1.10 | −0.58 | 1.463 |
| | 21.23 | 17.66 | 3.57 | | 0.577 | 0.6705 | −1.49 | | |
| | 20.78 | 17.34 | 3.44 | | 0.447 | 0.7337 | −1.36 | | |

| Sample | Cp Agg | Cp Actin | ΔCp | Mean ΔCp | ΔCp vs saline | 2-ΔΔCp vs saline | regulation | Mean regulation | std regulation |
|---|---|---|---|---|---|---|---|---|---|
| Aggrecan Saline | 27.57 | 16.69 | 10.88 | 10.22 | | | | | |
| | 26.34 | 16.4 | 9.94 | | | | | | |
| | 25.55 | 15.72 | 9.83 | | | | | | |
| Aggrecan Dexamethasone | 20.48 | 14.2 | 6.28 | 6.523 | −3.94 | 15.313 | 15.31 | 13.03 | 2.0074 |
| | 20.68 | 13.99 | 6.69 | | −3.53 | 11.525 | 11.52 | | |
| | 20.44 | 13.84 | 6.6 | | −3.62 | 12.267 | 12.27 | | |
| Aggrecan Mifepristone | 25.97 | 15.68 | 10.29 | 9.247 | 0.073 | 0.9504 | −1.05 | 1.55 | 2.3111 |
| | 24.4 | 15.42 | 8.98 | | −1.24 | 2.3565 | 2.36 | | |
| | 23.94 | 15.47 | 8.47 | | −1.75 | 3.3558 | 3.36 | | |
| Aggrecan Ampion | 23.54 | 16.68 | 6.86 | 6.067 | −3.36 | 10.244 | 10.24 | 19.16 | 8.4434 |
| | 23.28 | 17.4 | 5.88 | | −4.34 | 20.205 | 20.21 | | |
| | 22.66 | 17.2 | 5.46 | | −4.76 | 27.033 | 27.03 | | |
| Aggrecan NAT | 25.43 | 17.19 | 8.24 | 7.1 | −1.98 | 3.9358 | 3.94 | 11.66 | 10.952 |
| | 23.3 | 17.68 | 5.62 | | −4.6 | 24.195 | 24.20 | | |
| | 24.4 | 16.96 | 7.44 | | −2.78 | 6.8527 | 6.85 | | |
| Aggrecan Caprylate | 21.64 | 15.53 | 6.11 | 7.42 | −4.11 | 17.228 | 17.23 | 10.81 | 8.3209 |
| | 25.43 | 15.71 | 9.72 | | −0.5 | 1.4109 | 1.41 | | |
| | 21.95 | 15.52 | 6.43 | | −3.79 | 13.801 | 13.80 | | |
| Aggrecan DADKP | 24.7 | 15.64 | 9.06 | 7.28 | −1.16 | 2.2294 | 2.23 | 10.65 | 8.511 |
| | 23.56 | 16.73 | 6.83 | | −3.39 | 10.459 | 10.46 | | |
| | 22.36 | 16.41 | 5.95 | | −4.27 | 19.248 | 19.25 | | |
| Aggrecan Mix | 21.47 | 16.62 | 4.85 | 5.023 | −5.37 | 41.26 | 41.26 | 37.33 | 8.649 |
| | 21.36 | 15.92 | 5.44 | | −4.78 | 27.411 | 27.41 | | |
| | 20.34 | 15.56 | 4.78 | | −5.44 | 43.311 | 43.31 | | | cells in pellet
cells with nodules

| Sample | Cp TIMP1 | Cp Actin | ΔCp | Mean ΔCp | ΔΔCp vs saline | 2-ΔΔCp vs saline | regulation | Mean regulation | std regulation |
|---|---|---|---|---|---|---|---|---|---|
| TIMP1 Saline | 21.32 | 16.69 | 4.63 | 3.767 | | | | | |
| | 19.91 | 16.4 | 3.51 | | | | | | |
| | 18.88 | 15.72 | 3.16 | | | | | | |
| TIMP1 Dexamethasone | 17.35 | 14.2 | 3.15 | 3.16 | −0.62 | 1.5333 | 1.53 | 1.53 | 0.2057 |
| | 17.35 | 13.99 | 3.36 | | −0.41 | 1.3256 | 1.33 | | |
| | 16.81 | 13.84 | 2.97 | | −0.8 | 1.7371 | 1.74 | | |
| TIMP1 Mifepristone | 19.69 | 15.68 | 4.01 | 4.227 | 0.243 | 0.8448 | −1.18 | −1.38 | 0.1792 |
| | 19.8 | 15.42 | 4.38 | | 0.613 | 0.6537 | −1.53 | | |
| | 19.76 | 15.47 | 4.29 | | 0.523 | 0.6958 | −1.44 | | |
| TIMP1 Ampion | 19.44 | 16.68 | 2.76 | 2.993 | −1.01 | 2.0093 | 2.01 | 1.72 | 0.2669 |
| | 20.42 | 17.4 | 3.02 | | −0.75 | 1.6779 | 1.68 | | |
| | 20.4 | 17.2 | 3.2 | | −0.57 | 1.4811 | 1.48 | | |
| TIMP1 NAT | 20.59 | 17.19 | 3.4 | 3.537 | −0.37 | 1.2894 | 1.29 | 1.18 | 0.0987 |
| | 21.28 | 17.68 | 3.6 | | −0.17 | 1.1225 | 1.12 | | |
| | 20.57 | 16.96 | 3.61 | | −0.16 | 1.1147 | 1.11 | | |
| TIMP1 Caprylate | 17.65 | 15.53 | 2.12 | 3.143 | −1.65 | 3.1311 | 3.13 | 1.12 | 2.3073 |
| | 18.77 | 15.71 | 3.06 | | −0.71 | 1.632 | 1.63 | | |
| | 19.77 | 15.52 | 4.25 | | 0.483 | 0.7153 | −1.40 | | |
| TIMP1 DADKP | 18.64 | 15.64 | 3 | 3.04 | −0.77 | 1.7013 | 1.70 | 1.66 | 0.13 |
| | 19.9 | 16.73 | 3.17 | | −0.6 | 1.5122 | 1.51 | | |
| | 19.36 | 16.41 | 2.95 | | −0.82 | 1.7613 | 1.76 | | |
| TIMP1 Mix | 19.61 | 16.62 | 2.99 | 3.56 | −0.78 | 1.7132 | 1.71 | 0.53 | 1.5754 |
| | 19.51 | 15.92 | 3.59 | | −0.18 | 1.1303 | 1.13 | | |
| | 19.66 | 15.56 | 4.1 | | 0.333 | 0.7937 | −1.26 | | |

Figure 3A:
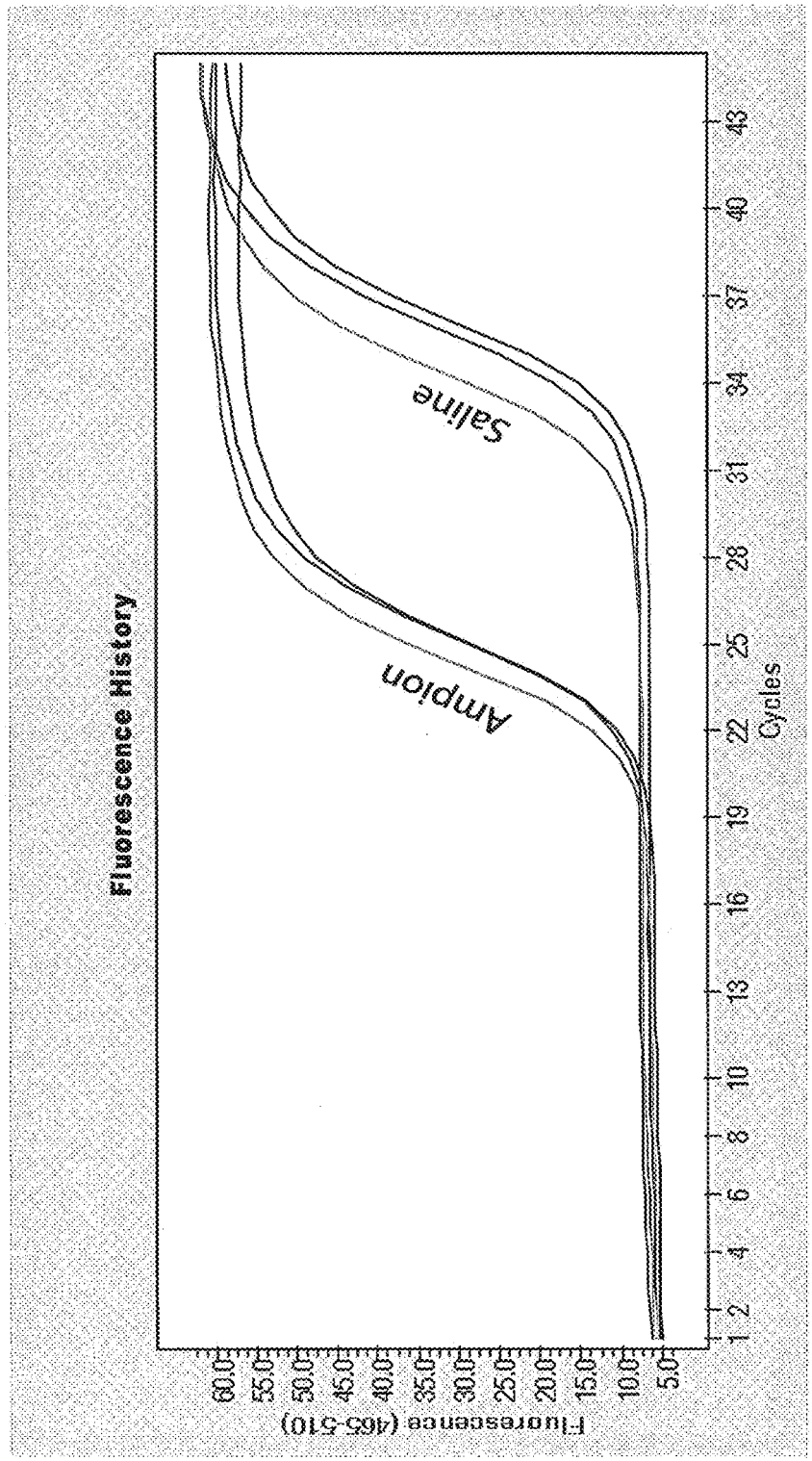
FIGS. 3A, 3B and 3C illustrate the enhancement of collagen (FIG. 3A) and aggrecan (FIG. 3B) and GAPDH (FIG. 3C) transcription by stem cells treated with DA-DKP as compared to saline.
Figure 3B:
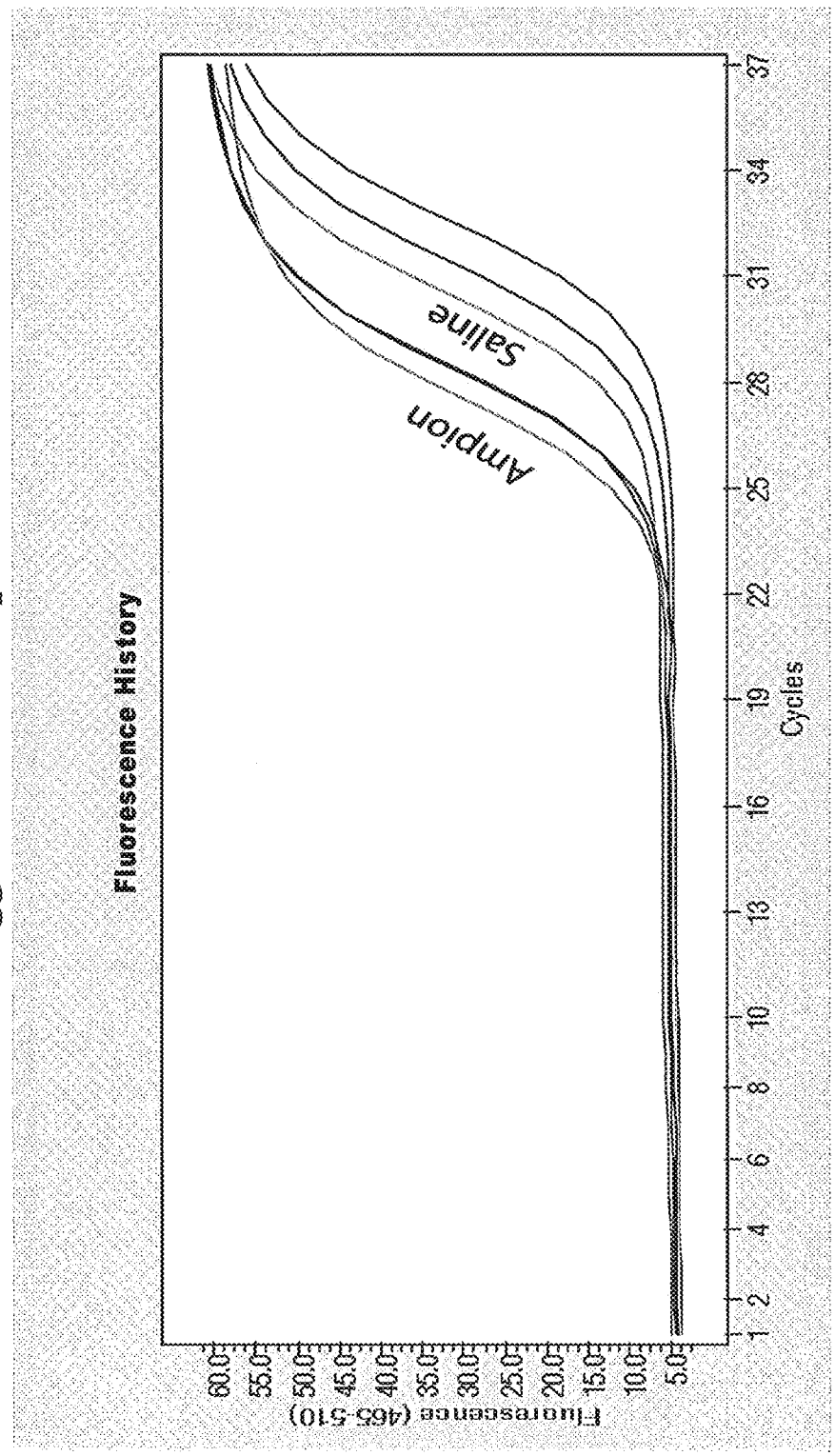
Figure 3C:
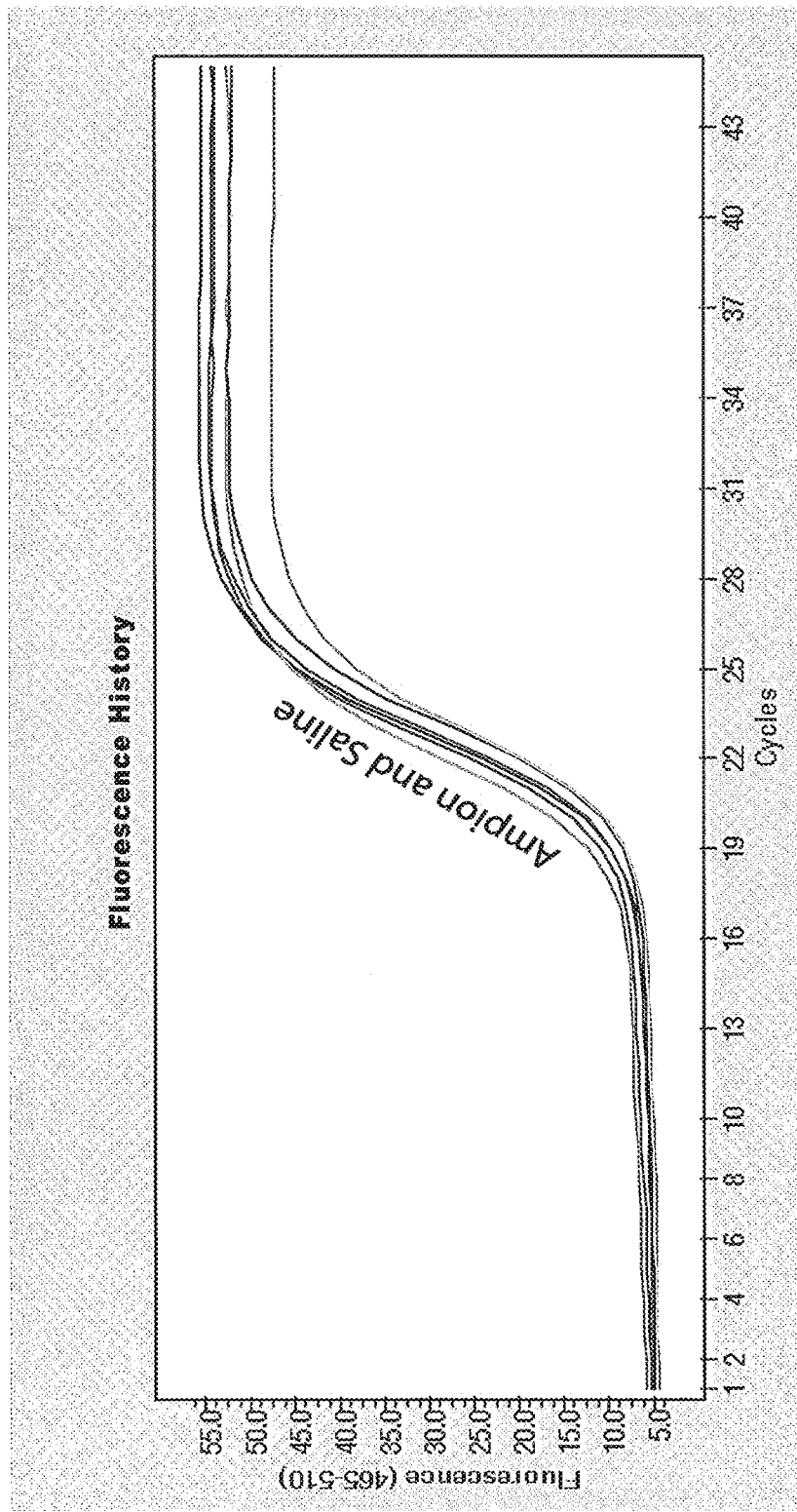

At day 22, the inventors observed greatly enhanced collagen transcription following DADKP treatment. Additionally, drug treatments also showed some activity, but not nearly as pronounced as DADKP. Transcription of Collagen 2a1 and aggrecan showed a 2000-fold and 20-fold increase, respectively, at day 22 following treatment with DADKP and, similarly, following at day 22 following Ampion treatment (see FIG. 3).

Discussion/Conclusion:

DADKP treatment exhibited increased transcription of Collagen 2A1 and possibly Aggrecan. Visual observations suggest that the architecture of the culture may also effect the collagen transcription.

Example 3

Following the experiments described in Example 2, a standard procedure for testing Mesenchymal chondrogenesis protocol is developed. This examples sets forth the standardized chondrogenic testing protocol and expected results.

Materials/Equipment:

Materials:
- Passage 5 Bone marrow derived human mesenchymal stem cells (HUXMA-01001, Cyagen Biosciences, Sunnyvale Calif.)
- Mesenchymal Stem Cell Chondrogenic Differentiation medium (GUXMX-90041, Cyagen Biosciences, Sunnyvale Calif.)
- TheraPEAK MSCGM chemically defined Stem cell medium (190632 Lonza)
- 1 mM dexamethasone acetate and mifepristone in absolute ethanol
- Saline or 0.9% Sodium chloride for injection ZR Flush
- Sterile filtered 0.6 mM sodium caprylate in saline
- Sterile filtered 3 mM NAT in saline; To prepare, heat at 60° C. for 30 minutes then sonicate for 5 minutes.
- Sterile filtered 10 mM DADKP in saline
- 0.2 µM syringe filters
- Hepes buffered saline, Trypsin/EDTA, Trypsin neutralizing solution (Lonza reagent pack)
- 75 and 182 cm2 tissue culture flasks
- pipettes and sterile tips
- Tissue culture hood, humidified CO2 incubator, water or bead bath
- 24 well tissue culture plates
- Qiagen RNeasy plus spin columns (Qiagen 74134)
- Qiagen RT2 qPCR primer pairs for Collagen 2A1, MMP13, TIMP1, Aggrecan, GAPDH, and Actin B
- Roche Sybr green I master mix and Invitrogen Superscript VILO master mix.
- Roche 480 lightcycler Procedure/Methodologies:

Cell expansion from frozen stocks:
- Passage 4 HUXMA cells were cryo-preserved using standard procedures and stored in liquid nitrogen prior to use.
- Remove one vial from liquid nitrogen storage and place up in three 75 cm2 tissue culture flasks containing 15 mls TheraPEAK MSCGM each.
- Incubate cells at 37° C. and 5% CO2 in humidified incubator until 60-70% confluence is achieved. (approximately 3 days)
- Trypsinize cells from flasks using standard protocol and place cells from one 75 cm2 into one 182 cm2 flask containing 40 mls TheraPEAK MSCGM.
- Incubate cells until 80-90% confluence is observed. (approximately 4 days)
- Trypsinize cells again and proceed to next step.

Plating and treatment of cells:
- Prepare the following working dilutions in saline for injection from the stocks listed above and warm to 37° C. in bath. (Controls and solutions designed to mimic final concentrations of some known Ampion components)
- 4 uM Dexamethasone and mifepristone
- 3 mM NAT
- 0.6 mM caprylate
- 80 µM DADKP
- Mix of 3 mM NAT, 0.6 mM caprylate, 80 µM DADKP
- In addition, warm saline and Ampion stock to 37° C. in bath.
- Mix Cyagen Chondrogenic Differentiation medium following instructions but EXCLUDE dexamethasone and TGF beta 3 supplements. Warm to 37° C. in bath.
- Prepare a 1.0×107 cell suspension of HUXMA stem cells in warmed chondrogenic medium then spot 20 µl in the middle of each well to be used in 24 well tissue culture plates. (200,000 cells per spot)
- Incubate at 37° C. and 5% CO2 for one hour.
- Remove plates from incubator and gently add 720 µl chondrogenic medium to each well.
- Add 250 µl saline, Ampion, or control solutions to the appropriate wells in triplicate.
- Then add 10 µl of the TGF beta 3 solution supplied by Cyagen to each well.
- Place plates back in to incubator.
- Medium exchanges were performed every 3-4 days by aspirating the medium from the wells and replacing with fresh chondrogenic medium, diluted stocks, and TGF beta 3 as described above.

RNA isolations and analysis:
- Plates were processed as follows at day 7, 14, and 22 post treatment (with the described medium exchanges).
- Remove the medium from the wells and save for further protein analysis.
- To each well add Qiagen RNeasy plus lysis buffer (with 2ME) and gently shake for 10 minutes.
- Transfer solution to Qiashredder columns and spin at 14,000 rpm for 2 minutes.
- Proceed with RNeasy plus protocol following manufacturers recommendations.
- Elute RNA from columns using 25 µl RNase free water.

cDNA synthesis and real time PCR:
- First strand synthesis of cDNA from all samples was then performed following the recommended 20 µl total volume protocol using 10 µl isolated RNA.
- All cDNA reactions were then diluted with 30 µl nuclease free water.
- Real time PCR was then performed using 5 µl diluted cDNA, Roche Syber green master mix, and Qiagen RT2 qPCR primer pairs (20 µl total volume).

Expected Results:

Treatment of bone marrow mesenchymal stem/stromal cells (MSCs) stem cells with DADKP significantly increases chondrogenesis, at least as measured by transcription of collagen 2a1 and aggrecan. Following the treatment of these cells with a composition containing N-acetyl tryptophan (NAT), caprylate and DADKP, transcription of collagen 2a1 may be observed to increase by greater than 1000-fold, and may be observed to increase by greater than 2000-fold.

Treatment of the same cells with dexamethasone and mifepristone shows a mild increase in markers of chondrogenesis, substantially below the 1000-fold increase in transcription of collagen 2a1 observed following treatment with DADKP or the composition containing N-acetyl tryptophan, caprylate and DADKP. Similarly, treatment with N-acetyl tryptophan or caprylate also results in moderate increase in markers of chondrogenesis.

Example 4

This example demonstrated the effect that Ampion™ has on the transcription of CXCR4 or CXCL12 by mesenchymal stem cells (MSC) grown in 3D culture. Several groups have demonstrated that CXCR4 transcription and expression is lost when stem cells are cultured. This effect is more pronounced if the cells are grown directly on plastic in a 2D conformation. In this example, MSCs are cultured in hanging drop cultures in the presence of Ampion™ and then mRNA is evaluated by RTPCR.

Materials:
  Passage 5 Bone marrow derived human mesenchymal stem cells (HUXMA-01001, Cyagen Biosciences, Sunnyvale Calif.)
  Mesenchymal Stem Cell Chondrogenic Differentiation medium (GUXMX-90041, Cyagen Biosciences, Sunnyvale Calif.)
  TheraPEAK MSCGM chemically defined Stem cell medium (190632 Lonza)
  Lonza MSGM (contains serum)
  10 mM Cobalt chloride in saline, sterile filtered (Sigma)
  Saline or 0.9% Sodium chloride for injection ZR Flush (Excelsior Medical, Neptune N.J.)
  0.2 µM syringe filters
  Hepes buffered saline, Trypsin/EDTA, Trypsin neutralizing solution (Lonza reagent pack)
  182 $cm^2$ tissue culture flasks
  pipettes and sterile tips
  Tissue culture hood, humidified $CO_2$ incubator, water or bead bath
  10 $cm^2$ petri dishes
  Qiagen RNeasy plus spin columns (Qiagen 74134)
  Qiagen $RT^2$ qPCR primer pairs for CXCR4, CXCL12, Collagen 2A1, MMP14, MMP13, Aggrecan, IGA4, GAPDH, and Actin B
  Roche Sybr green I master mix and Invitrogen Superscript VILO master mix.
  Roche 480 lightcycler
Cell Expansion:
  Passage 5 HUXMA cells were removed from liquid nitrogen storage and expanded in 182 $cm^2$ flasks containing 40 mls TheraPEAK MSCGM until 80-90% confluence.
  Trypsinize cells using standard protocol and proceed to the next step.
Preparation of Hanging Drop Cultures:
  Prepare the following working dilutions in saline for injection from the stocks listed above.
    Saline
    800 uM Cobalt Chloride in saline
    Neat Ampion
  Warm dilutions and Lonza MSGM to 37° C. in bead bath.
  Prepare a 1.0×$10^6$ cell suspension of HUXMA stem cells in warmed MSCGM medium.
  In a sterile tube mix 250 µl appropriate working dilution, 250 µl cell suspension (250,000 cells per reaction), 500 µl warmed MSCGM.
  Carefully place 40 µl "spots" of the resulting solution on the underneath surface of a petri dish lid. (Should result in 40 total spots).
  Place 20 mls sterile PBS in the bottom reservoir of the petri dish then invert the lid over the PBS.
  Incubate at 37° C. and 5% $CO_2$.
RNA Isolations and Analysis:
  After 4 days, remove the plates from the incubator.
  Wash spheroids from the lid with 5 mls of the warm PBS in the bottom of each plate and transfer to 15 ml conical centrifuge tubes.
  Spin cells at 1000 RPM for 5 minutes and aspirate the solution.
  To each tube, add 350 µl Qiagen RNeasy plus lysis buffer (with 2ME).
  Transfer solution to Qiashredder columns and spin at 14,000 rpm for 2 minutes.
  Proceed with RNeasy plus protocol following manufacturers recommendations.
  Elute RNA from columns using 30 µl RNase free water.
cDNA Synthesis and Real Time PCR:
  First strand synthesis of cDNA from all samples was then performed following the recommended 20 µl total volume protocol using 10 µl isolated RNA.
  All cDNA reactions were then diluted with 30 µl nuclease free water.
  Real time PCR was then performed using 5 µl diluted cDNA, Roche Syber green master mix, and Qiagen $RT^2$ qPCR primer pairs (20 µl total volume).
  Relative gene expression determined by delta deta Ct method.

Cobalt treatment appeared to greatly affect the GAPDH expression of these cells. The cp calls were pushed very early and exhibit multiple bands. As a result, actin B was used as well to evaluate the relative expression by the delta delta method. The results are shown below in Tables 13 and 14.

TABLE 13

Effect on CXCR4

Actin normalization

| Sample | Cp CXC | Cp Actin | ΔCp | ΔΔCp vs saline | $2^{-\Delta\Delta Cp}$ vs saline | regulation |
|---|---|---|---|---|---|---|
| CXCR4 Saline | 32.93 | 18.43 | 14.25 | | | |
| | 32.47 | 18.47 | | | | |
| Average | 32.7 | 18.45 | | | | |
| CXCR4 Cobalt | 29.88 | 18.6 | 11.19 | −3.065 | 8.369 | 8.37 |
| | 29.6 | 18.51 | | | | |
| Average | 29.74 | 18.555 | | | | |
| CXCR4 Ampion 007 | 31.61 | 20.31 | 11.43 | −2.825 | 7.086 | 7.09 |
| | 31.83 | 20.28 | | | | |
| Average | 31.72 | 20.295 | | | | |

TABLE 13-continued

Effect on CXCR4

GAPDH normalization

| Sample | Cp CXC | Cp GAPDH | ΔCp | ΔΔCp vs saline | $2^{-\Delta\Delta Cp}$ vs saline | regulation |
|---|---|---|---|---|---|---|
| CXCR4 Saline | 32.93 | 19.27 | 13.47 | | | |
|  | 32.47 | 19.19 | | | | |
| Average | 32.7 | 19.23 | | | | |
| CXCR4 Ampion 007 | 31.61 | 20.13 | 11.59 | −1.88 | 3.681 | 3.68 |
|  | 31.83 | 20.13 | | | | |
| Average | 31.72 | 20.13 | | | | |

Actin/GAPDH average normalization

| Sample | Av Cp CXC | Av Cp Act/Gap | ΔCp | ΔΔCp vs saline | $2^{-\Delta\Delta Cp}$ vs saline | regulation |
|---|---|---|---|---|---|---|
| CXCR4 Saline | 32.7 | 18.84 | 13.86 | | | |
| CXCR4 Ampion 007 | 31.72 | 20.2125 | 11.51 | −2.353 | 5.107 | 5.11 |

TABLE 14

Effect on CXCl12

Actin normalization

| Sample | Cp CXC | Cp Actin | ΔCp | ΔΔCp vs saline | $2^{-\Delta\Delta Cp}$ vs saline | regulation |
|---|---|---|---|---|---|---|
| CXCL12 Saline | 25.57 | 18.43 | 7.13 | | | |
|  | 25.59 | 18.47 | | | | |
| Average | 25.58 | 18.45 | | | | |
| CXCL12 Cobalt | 33.29 | 18.6 | 14.91 | 7.78 | 0.005 | −219.79 |
|  | 33.64 | 18.51 | | | | |
| Average | 33.47 | 18.555 | | | | |
| CXCL12 Ampion 007 | 31.61 | 20.31 | 11.43 | 4.295 | 0.051 | −19.63 |
|  | 31.83 | 20.28 | | | | |
| Average | 31.72 | 20.295 | | | | |

GAPDH normalization

| Sample | Cp CXC | Cp GAPDH | ΔCp | ΔΔCp vs saline | $2^{-\Delta\Delta Cp}$ vs saline | regulation |
|---|---|---|---|---|---|---|
| CXCL12 Saline | 25.57 | 19.27 | 6.35 | | | |
|  | 25.59 | 19.19 | | | | |
| Average | 25.58 | 19.23 | | | | |
| CXCL12 Ampion 007 | 31.61 | 20.13 | 11.59 | 5.24 | 0.026 | −37.79 |
|  | 31.83 | 20.13 | | | | |
| Average | 31.72 | 20.13 | | | | |

Actin/GAPDH average normalization

| Sample | Av Cp CXC | Av Cp Act/Gap | ΔCp | ΔΔCp vs saline | $2^{-\Delta\Delta Cp}$ vs saline | regulation |
|---|---|---|---|---|---|---|
| CXCL12 Saline | 25.58 | 18.84 | 6.74 | | | |
| CXCL12 Ampion 007 | 31.72 | 20.2125 | 11.51 | 4.768 | 0.037 | −27.24 |

Figure 5:
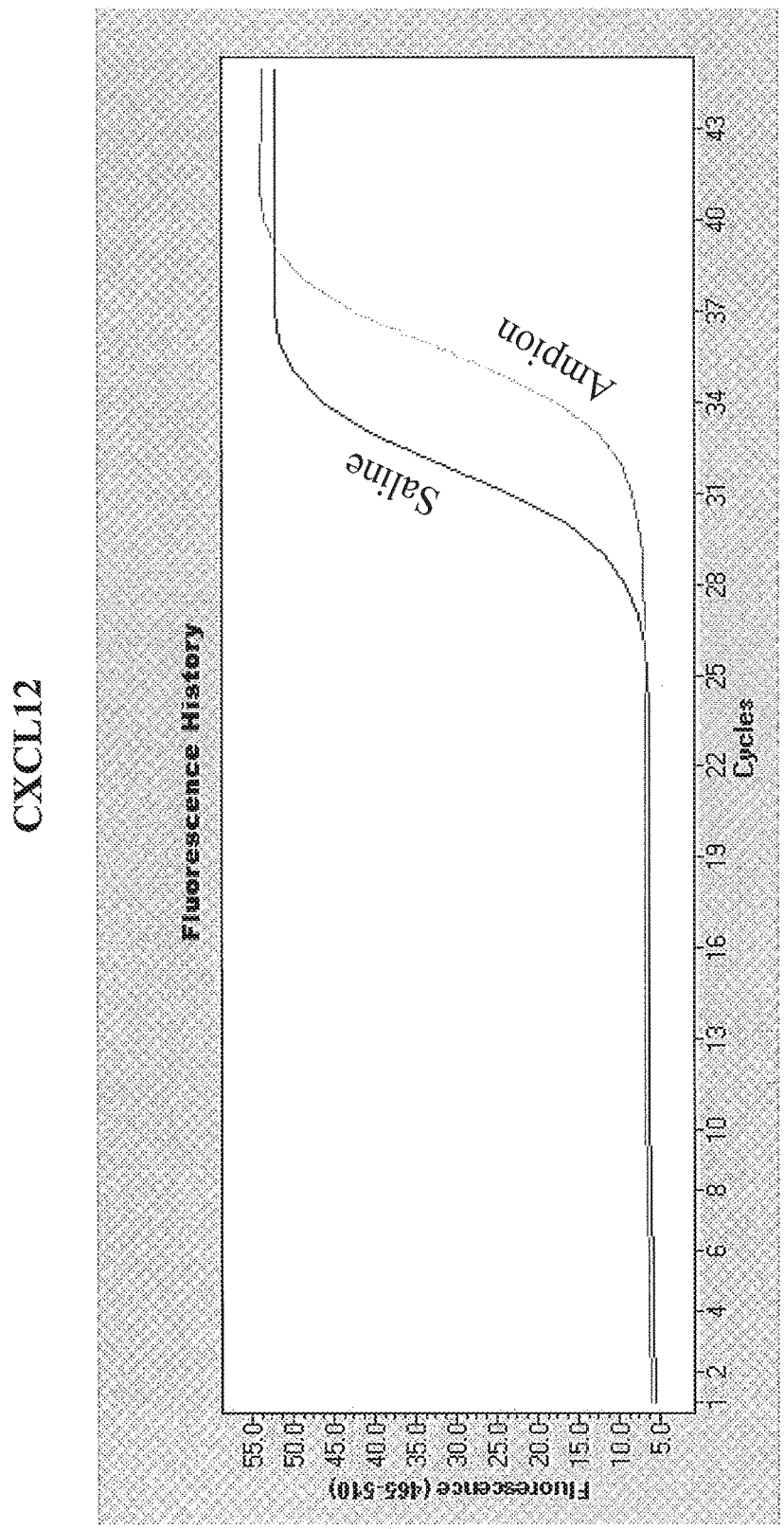
FIG. 5 illustrates the decrease in production of CXCL12 by mesenchymal stem cells grown in 3D culture by Ampion™ compared to saline.

These results are further shown in FIGS. 4 and 5.

The results of this experiment demonstrate that Ampion affects CXCR4 and CXCL12. More particularly, Ampion caused a 3-7 fold increase in CXCR4 while reducing CXCL12 by 19-37 times.

Example 5

This example will demonstrate the effect that Ampion™ has on the migration of stem cells in vitro. Previous data suggested that transcription of CXCR4 or CXCL12 were both effected by treatment with Ampion. This experiment will be designed to establish if migration of MSC is altered as well.

Materials:
  Passage 5 Bone marrow derived human mesenchymal stem cells (HUXMA-01001, Cyagen Biosciences, Sunnyvale Calif.)
  TheraPEAK MSCGM chemically defined Stem cell medium (190632 Lonza)

Lonza MSGM, Gibco RPMI, Gibco Defined fetal bovine serum.
10 mM Cobalt chloride in saline, sterile filtered (Sigma)
Saline or 0.9% Sodium chloride for injection ZR Flush (Excelsior Medical, Neptune N.J.)
0.2 µM syringe filters
Hepes buffered saline, Trypsin/EDTA, Trypsin neutralizing solution (Lonza reagent pack)
25 and 175 $cm^2$ tissue culture flasks
pipettes and sterile tips
Tissue culture hood, humidified $CO_2$ incubator, water or bead bath
8.0 um Thincert tissue culture inserts and 24 well tissue culture plates (Greiner)
50 µg Calcein AM vials (BD Biosciences)
DMSO (Sigma)

Cell Expansion:
Passage 5 HUXMA cells were removed from liquid nitrogen storage and expanded in 175 $cm^2$ flasks containing 40 mls TheraPEAK MSCGM until 80-90% confluence.
Trypsinize cells using standard protocol and proceed to the next step.

Treatment of Cells:
Prepare the following working dilutions in saline for injection from the stocks listed above.
Saline
800 uM Cobalt Chloride in saline
Neat Ampion
Warm dilutions and Lonza MSCGM to 37° C. in bead bath.
Prepare a cell suspension of HUXMA stem cells in warmed MSCGM medium.
Count and then bring up 250,000 from the cell suspension in 4 mls warmed MSCGM.
Add the diluted cell solution to a 25 $cm^2$ tissue culture flasks.
Add 1 ml of the appropriate working dilution to the flask.
Incubate at 37° C. and 5% $CO_2$ for 72 hours.

Invasion Assay:
Remove the cells from the flask with trypsin and place in 600 µl RPMI+0.5% FBS.
Add 200 µl of the resulting cell suspension to the upper chamber of thinserts (3 inserts per treatment group) resting in a 24 well tissue culture plate.
Add 600 µl RPMI+0.5% FBS to the bottom chamber of the transwell system.
Add 66 µl of one of the following solutions to the bottom chamber for each treatment group.

550 ng/ml SDF (final 50 ng/ml)
110 ng/ml TGF beta3 (final 10 ng/ml)
Serum (final 10%)
Incubate the plate for 24 hours at 37° C. and 5% $CO_2$.

Labeling and Cell Detection.
Remove two calcein AM vials and add 20 µl DMSO.
Transfer the contents of both vials to 12.5 ml RPMI containing 0.2% BSA.
Place 450 µl of the calcein AM solution (8 µM) in each well of a 24 well tissue culture plate.
Transfer the inserts from above to the wells containing calcein AM and incubate 45 minutes at 37° C. and 5% $CO_2$.
After loading the cells with calcein AM, transfer the inserts to 24 well tissue culture plate wells containing 450 µl trypsin EDTA and incubate for another 10 minutes.
Discard inserts then add 450 µl trypsin neutralizing solution to each well.
Transfer 250 µl of the resulting solution to a 96 well black, flat bottom plate well (each reaction in triplicate).
Read fluorescence at 485 nm excitation and 530 nm emission.

Figure 6:
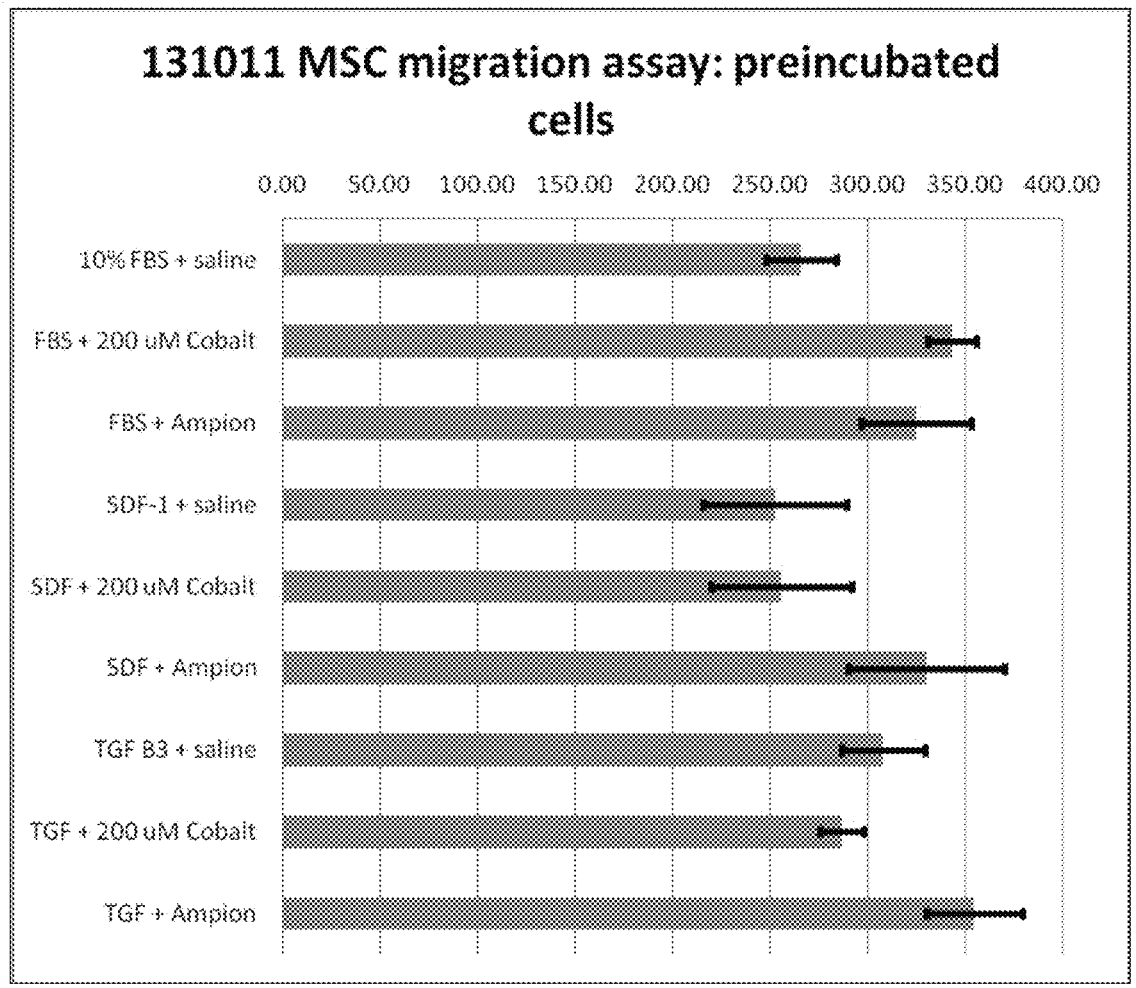
FIG. 6 illustrates the effect of Ampion™ on the migration of stem cells in vitro.

The results of this experiment are shown below in Table 15 and FIG. 6.

TABLE 15

Migration Assay
Assay using pretreated cells

| Sample | mean FU | std FU | FU 1 | FU 2 | FU 3 | pvalue vs saline | % increase |
|---|---|---|---|---|---|---|---|
| 10% FBS + saline | 265.79 | 17.95 | 284.62 | 248.87 | 263.89 | | |
| FBS + 200 uM Cobalt | 343.27 | 12.69 | 346.49 | 329.28 | 354.03 | 0.005 | 29.1% |
| FBS + Ampion | 324.99 | 28.29 | 292.35 | 342.54 | 340.07 | 0.047 | 22.3% |
| SDF-1 + saline | 252.74 | 36.85 | 210.41 | 270.2 | 277.61 | | |
| SDF + 200 uM Cobalt | 255.86 | 36.34 | 215.24 | 267.07 | 285.27 | 0.922 | 1.2% |
| SDF + Ampion | 329.89 | 40.14 | 310.92 | 302.75 | 376 | 0.071 | 30.5% |
| TGF B3 + saline | 307.86 | 21.33 | 295.48 | 295.6 | 332.49 | | |
| TGF + 200 uM Cobalt | 286.77 | 11.06 | 274.97 | 288.44 | 296.9 | 0.226 | −6.8% |
| TGF + Ampion | 354.67 | 24.38 | 360.25 | 327.99 | 375.78 | 0.068 | 16.3% |

For all the chemotactic signals tested, pretreatment of MSC with Ampion™ increased the detectable amount of cells in the bottom chamber after 24 hours. Ampion increased FBS migration by 22%, SDF-1 by 31%, and TGF beta3 by 15%.

Example 6

This example demonstrates that Ampion™ expedites chondrogenesis. Also, Ampion™ has an additive or synergistic effect on the transcription or translation of genes important for the chondrocyte lineage.

Materials:
Passage 5 Bone marrow derived human mesenchymal stem cells (HUXMA-01001, Cyagen Biosciences, Sunnyvale Calif.)
Mesenchymal Stem Cell Chondrogenic Differentiation medium (GUXMX-90041, Cyagen Biosciences, Sunnyvale Calif.)
TheraPEAK MSCGM chemically defined Stem cell medium (190632 Lonza)
1 mM Dexamethasone acetate and mifepristone in absolute ethanol (Sigma)

Saline or 0.9% Sodium chloride for injection ZR Flush (Excelsior Medical, Neptune N.J.)
Sterile filtered 0.6 mM sodium caprylate in saline (sigma)
Sterile filtered 3 mM NAT in saline (sigma); To prepare, heat at 60° C. for 30 minutes then sonicate for 5 minutes.
Sterile filtered 10 mM DADKP in saline
0.2 µM syringe filters
Hepes buffered saline, Trypsin/EDTA, Trypsin neutralizing solution (Lonza reagent pack)
182 cm² tissue culture flasks
pipettes and sterile tips
Tissue culture hood, humidified $CO_2$ incubator, water or bead bath
24 well tissue culture plates
Qiagen RNeasy plus spin columns (Qiagen 74134)
Qiagen $RT^2$ qPCR primer pairs for Collagen 2A1, MMP13, TIMP1, Aggrecan, GAPDH, and Actin B
Roche Sybr green I master mix and Invitrogen Superscript VILO master mix.
Roche 480 lightcycler Cell Expansion:
Passage 5 HUXMA cells were expanded in 175 cm² flasks containing 40 mls TheraPEAK MSCGM until 80-90% confluence.
Trypsinize cells from flasks using standard protocol and proceed to the next step.

Plating and Treatment of Cells:
Prepare the following working dilutions in saline for injection from the stocks listed above and warm to 37° C. in bath. (Controls and solutions designed to mimic final concentrations of some known Ampion components)
4 uM Dexamethasone and mifepristone
3 mM NAT
0.6 mM caprylate
80 µM DADKP
Mix of 3 mM NAT, 0.6 mM caprylate, 80 µM DADKP
In addition, warm saline and Ampion stock to 37° C. in bath.
Mix Cyagen Chondrogenic Differentiation medium following instructions but EXCLUDE dexamethasone and TGF beta 3 supplements. Warm to 37° C. in bath.
Prepare a $1.0 \times 10^7$ cell suspension of HUXMA stem cells in warmed chondrogenic medium then spot 20 µl in the middle of each well to be used in 24 well tissue culture plates. (200,000 cells per spot)
Incubate at 37° C. and 5% $CO_2$ for one hour.
Remove plates from incubator and gently add 720 µl chondrogenic medium to each well.
Add 250 µl saline, Ampion, or control solutions to the appropriate wells in triplicate.
Then add 10 µl of the TGF beta 3 solution supplied by Cyagen to each well.
Place plates back in to incubator.
Medium exchanges were performed every 3-4 days by aspirating the medium from the wells and replacing with fresh chondrogenic medium, diluted stocks, and TGF beta 3 as described above.

RNA Isolations and Analysis:
Plates were processed as follows at day 7, 14, and 22 post treatment (with the described medium exchanges).
Remove the medium from the wells and save for further protein analysis.
To each well add Qiagen RNeasy plus lysis buffer (with 2ME) and gently shake for 10 minutes.
Transfer solution to Qiashredder columns and spin at 14,000 rpm for 2 minutes.
Proceed with RNeasy plus protocol following manufacturers recommendations.
Elute RNA from columns using 25 µl RNase free water.

cDNA Synthesis and Real Time PCR:
First strand synthesis of cDNA from all samples was then performed following the recommended 20 µl total volume protocol using 10 µl isolated RNA.
All cDNA reactions were then diluted with 30 µl nuclease free water.
Real time PCR was then performed using 5 µl diluted cDNA, Roche Syber green master mix, and Qiagen $RT^2$ qPCR primer pairs (20 µl total volume).
Relative gene expression determined by delta deta Ct method.

Figure 7:
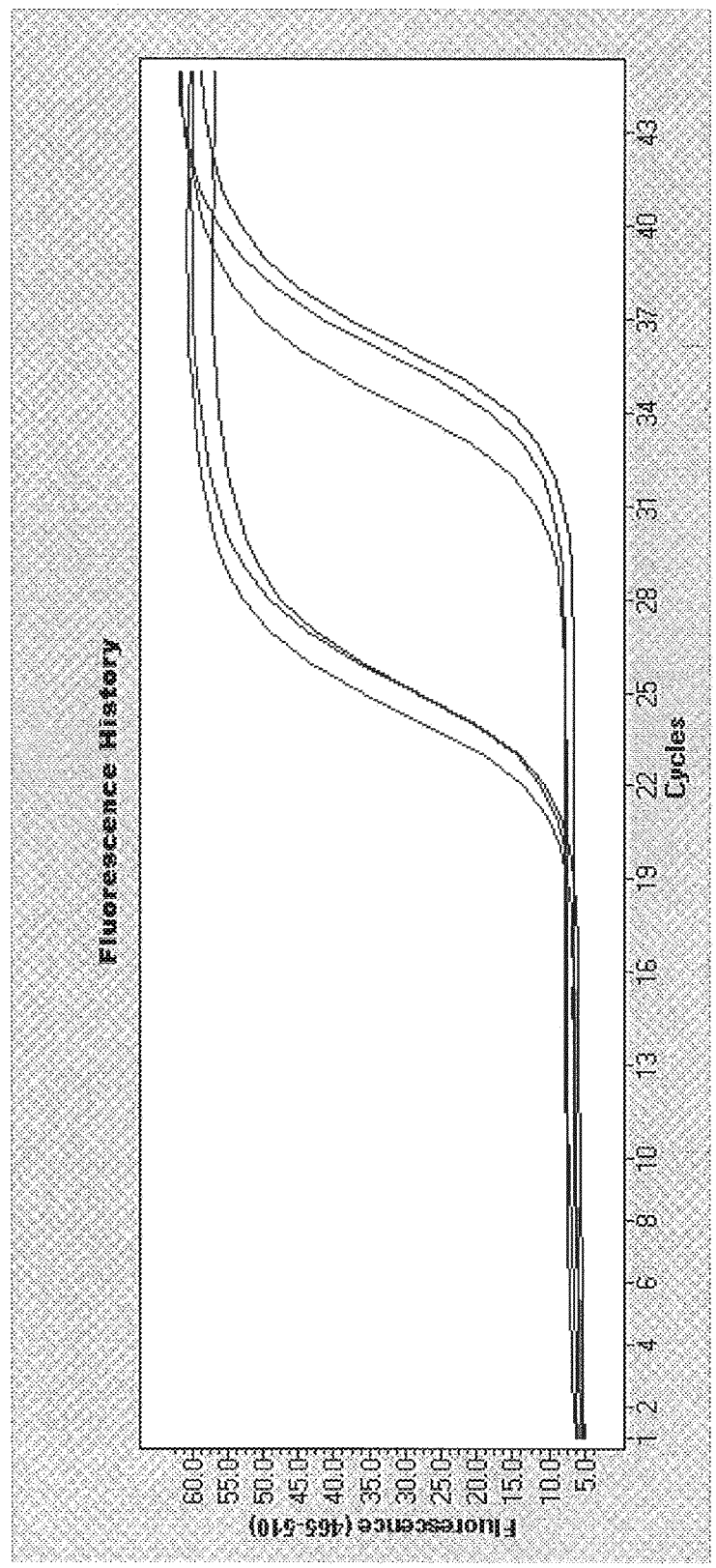
FIG. 7 demonstrates the effect of Ampion™ on the transcription of Collagen 2A1 by bone marrow derived human mesenchymal stem cells.
Figure 8:
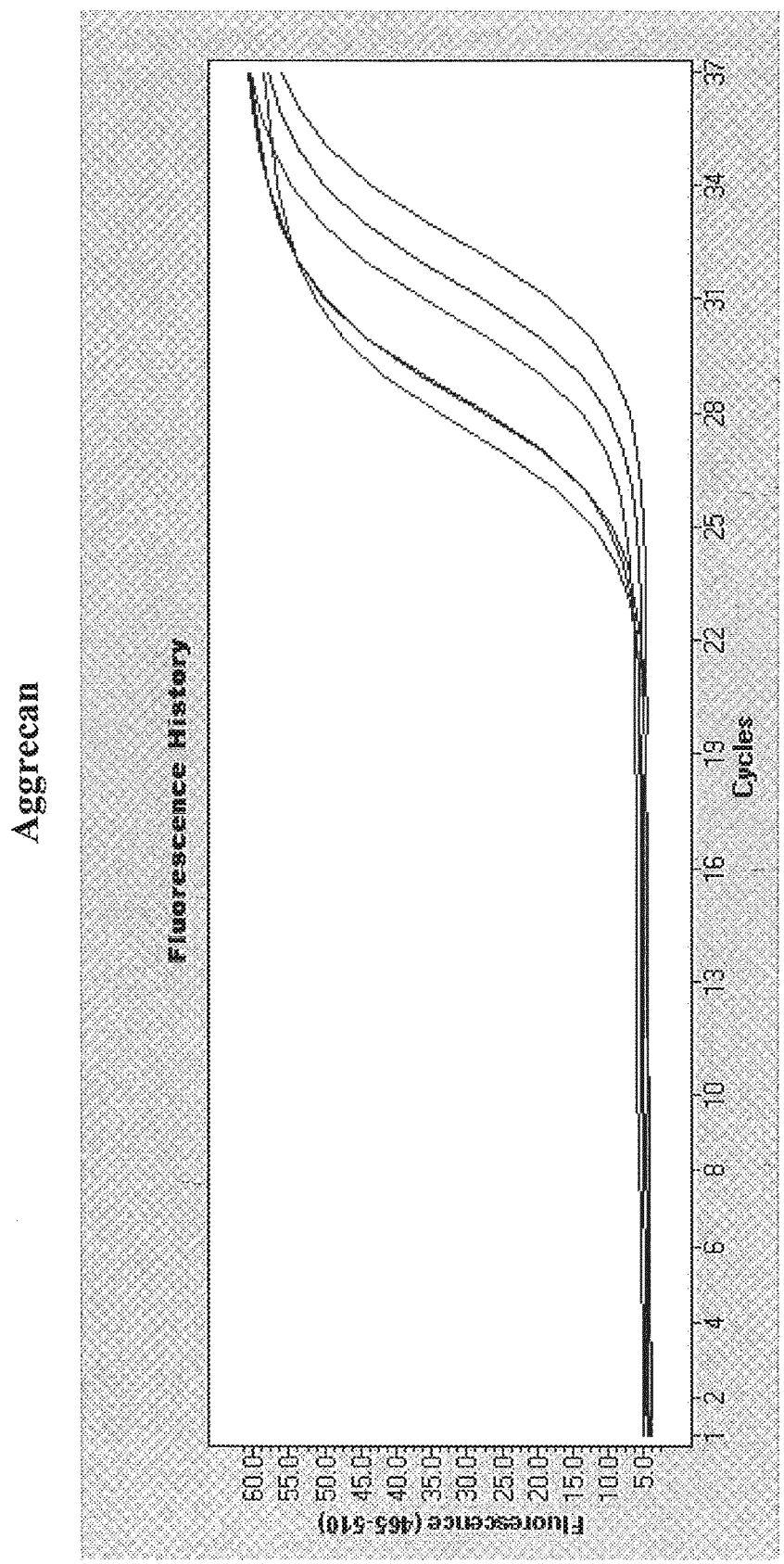
FIG. 8 demonstrates the effect of Ampion™ on the transcription of Aggrecan by bone marrow derived human mesenchymal stem cells.
Figure 9:
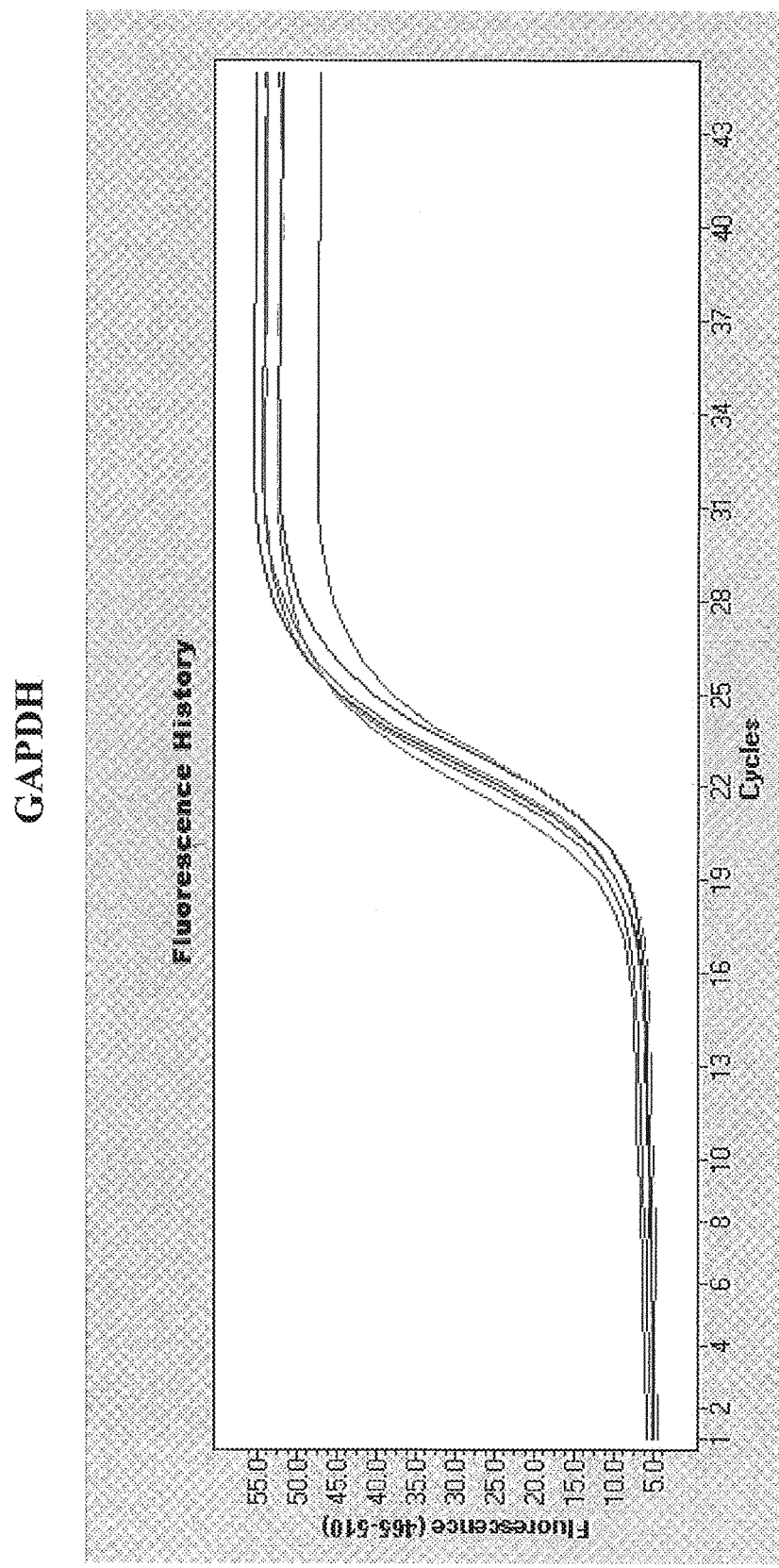
FIG. 9 demonstrates the effect of Ampion™ on the transcription of GAPDH by bone marrow derived human mesenchymal stem cells.

Results
The results of this experiment at Days 7 and 22 are shown below in Tables 15-16 and in FIGS. 7-9.

TABLE 15

Day 7 results
130515 Gene expression RTPCR

| Sample | Cp Coll | Cp Actin | ΔCp | Mean ΔCp | ΔΔCp vs saline | $2^{-\Delta\Delta Cp}$ vs saline | regulation | Mean regulation | std regulation |
|---|---|---|---|---|---|---|---|---|---|
| Collagen 2A1 Saline | 35.5 | 28.71 | 6.79 | 6.733 | | | | | |
| | 35.82 | 28.35 | 7.47 | | | | | | |
| | 34.62 | 28.68 | 5.94 | | | | | | |
| Collagen 2A1 Dexamethasone | 32.42 | 25.67 | 6.75 | 5.797 | 0.017 | 0.9885 | −1.01 | 1.44 | 2.1229 |
| | 32.42 | 27.07 | 5.35 | | −1.38 | 2.6087 | 2.61 | | |
| | 33.41 | 28.12 | 5.29 | | −1.44 | 2.7195 | 2.72 | | |
| Collagen 2A1 Mifepristone | 33.67 | 26.77 | 6.9 | 7.433 | 0.167 | 0.8909 | −1.12 | −1.82 | 1.1179 |
| | 32.73 | 24.36 | 8.37 | | 1.637 | 0.3216 | | | |
| | 34.82 | 27.79 | 7.03 | | 0.297 | 0.8141 | −1.23 | | |
| Collagen 2A1 Ampion | 31.34 | 27.08 | 4.26 | 4.15 | −2.47 | 5.5533 | 5.55 | 6.46 | 3.1219 |
| | 33.5 | 28.73 | 4.77 | | −1.96 | 3.8996 | 3.90 | | |
| | 31.94 | 28.52 | 3.42 | | −3.31 | 9.9406 | 9.94 | | |
| Collagen 2A1 NAT | 34.84 | 27.62 | 7.22 | 7.063 | 0.487 | 0.7137 | −1.40 | −0.61 | 1.4003 |
| | 33.83 | 27.11 | 6.72 | | −0.01 | 1.0093 | 1.01 | | |
| | 34.09 | 26.84 | 7.25 | | 0.517 | 0.699 | −1.43 | | |
| Collagen 2A1 Caprylate | 33.77 | 27.74 | 6.03 | 6.573 | −0.7 | 1.6283 | 1.63 | −0.18 | 1.5643 |
| | 33.95 | 27.14 | 6.81 | | 0.077 | 0.9482 | −1.05 | | |
| | 33.94 | 27.06 | 6.88 | | 0.147 | 0.9033 | −1.11 | | |

TABLE 15-continued

Day 7 results
130515 Gene expression RTPCR

| Sample | Cp Coll | Cp Actin | ΔCp | Mean ΔCp | ΔΔCp vs saline | $2^{-\Delta\Delta Cp}$ vs saline | regulation | Mean regulation | std regulation |
|---|---|---|---|---|---|---|---|---|---|
| Collagen 2A1 DADKP | 32.82 | 26.81 | 6.01 | 6.993 | −0.72 | 1.651 | 1.65 | −0.62 | 2.0361 |
| | 34.44 | 26.52 | 7.92 | | 1.187 | 0.4393 | −2.28 | | |
| | 32.87 | 25.82 | 7.05 | | 0.317 | 0.8029 | −1.25 | | |
| Collagen 2A1 Mix | 32.57 | 26.67 | 5.9 | 6.6 | −0.83 | 1.7818 | 1.78 | −0.18 | 1.7056 |
| | 33.8 | 26.98 | 6.82 | | 0.087 | 0.9417 | −1.06 | | |
| | 33.45 | 26.37 | 7.08 | 7.08 | 0.347 | 0.7864 | −1.27 | | |
| MMP13 Saline | 32.64 | 28.71 | 3.93 | 4.637 | | | | | |
| | 33.19 | 28.35 | 4.84 | | | | | | |
| | 33.82 | 28.68 | 5.14 | | | | | | |
| MMP13 Dexamethasone | 31 | 25.67 | 5.33 | 4.493 | 0.693 | 0.6184 | −1.62 | 0.45 | 1.7977 |
| | 30.99 | 27.07 | 3.92 | | −0.72 | 1.6434 | 1.64 | | |
| | 32.35 | 28.12 | 4.23 | | −0.41 | 1.3256 | 1.33 | | |
| MMP13 Mifepristone | 31.98 | 26.77 | 5.21 | 5.7 | 0.573 | 0.6721 | −1.49 | −2.47 | 1.8254 |
| | 31.19 | 24.36 | 6.83 | | 2.193 | 0.2186 | | | |
| | 32.85 | 27.79 | 5.06 | | 0.423 | 0.7457 | −1.34 | | |
| MMP13 Ampion | 30.53 | 27.08 | 3.45 | 3.36 | −1.19 | 2.2763 | 2.28 | 2.59 | 1.1875 |
| | 32.69 | 28.73 | 3.96 | | −0.68 | 1.5984 | 1.60 | | |
| | 31.19 | 28.52 | 2.67 | | −1.97 | 3.9086 | 3.91 | | |
| MMP13 NAT | 32.77 | 27.62 | 5.15 | 5.523 | 0.513 | 0.7006 | −1.43 | −1.89 | 0.5175 |
| | 32.6 | 27.11 | 5.49 | | 0.853 | 0.5535 | −1.81 | | |
| | 32.77 | 26.84 | 5.93 | | 1.293 | 0.408 | −2.45 | | |
| MMP13 Caprylate | 33.77 | 27.74 | 6.03 | 5.623 | 1.393 | 0.3807 | −2.63 | −1.55 | 2.2483 |
| | 31.73 | 27.14 | 4.59 | | −0.05 | 1.0329 | 1.03 | | |
| | 33.31 | 27.06 | 6.25 | | 1.613 | 0.3268 | −3.06 | | |
| MMP13 DADKP | 31.81 | 26.81 | 5 | 5.017 | 0.363 | 0.7774 | −1.29 | −0.67 | 1.4896 |
| | 31.12 | 26.52 | 4.6 | | −0.04 | 1.0257 | 1.03 | | |
| | 31.27 | 25.82 | 5.45 | | 0.813 | 0.5691 | −1.76 | | |
| MMP13 Mix | 31.21 | 26.67 | 4.54 | 5.323 | −0.1 | 1.0693 | 1.07 | −1.10 | 1.9647 |
| | 32.31 | 26.98 | 5.33 | | 0.693 | 0.6184 | −1.62 | | |
| | 32.47 | 26.37 | 6.1 | | 1.463 | 0.3627 | −2.76 | | |

At day seven, elevated collagen type 2A1 and MMP13 expression were observed. All cultures were in discs except the Ampion™ treated wells which were pulled into loose pellets.

TABLE 16

Day 22
130529 Gene expression RTPCR

| Sample | Cp Coll | Cp GAPDH | ΔCp | Mean ΔCp | ΔΔCp vs saline | $2^{-\Delta\Delta Cp}$ vs saline | regulation | Mean regulation | std regulation |
|---|---|---|---|---|---|---|---|---|---|
| Collagen 2A1 Saline | 31.83 | 18.36 | 13.47 | 13.15 | | | | | |
| | 32.21 | 18.54 | 13.67 | | | | | | |
| | 30.25 | 17.95 | 12.3 | | | | | | |
| Collagen 2A1 Dexamethasone | 22.42 | 16.42 | 6 | 5.76 | −7.15 | 141.7 | 141.70 | 168.82 | 27.286 |
| | 21.94 | 16.41 | 5.53 | | −7.62 | 196.27 | 196.27 | | |
| | 21.42 | 15.67 | 5.75 | | −7.4 | 168.51 | 168.51 | | |
| Collagen 2A1 Mifepristone | 25.99 | 17.47 | 8.52 | 9.22 | −4.63 | 24.704 | 24.70 | 16.82 | 8.3693 |
| | 27.6 | 17.46 | 10.14 | | −3.01 | 8.0371 | 8.04 | | |
| | 26.84 | 17.84 | 9 | | −4.15 | 17.712 | 17.71 | | |
| Collagen 2A1 Ampion | 21.42 | 18.45 | 2.97 | 2.233 | −10.2 | 1157.4 | 1157.40 | 2077.99 | 938.43 |
| | 21.3 | 19.15 | 2.15 | | −11 | 2043.3 | 2043.27 | | |
| | 20.57 | 18.99 | 1.58 | | −11.6 | 3033.3 | 3033.29 | | |
| Collagen 2A1 NAT | 24.2 | 19.45 | 4.75 | 5.207 | −8.4 | 337.01 | 337.01 | 262.94 | 105.86 |
| | 23.63 | 18.76 | 4.87 | | −8.28 | 310.12 | 310.12 | | |
| | 24.67 | 18.67 | 6 | | −7.15 | 141.7 | 141.70 | | |
| Collagen 2A1 Caprylate | 22.93 | 16.85 | 6.08 | 6.557 | −7.07 | 134.05 | 134.05 | 101.18 | 36.373 |
| | 25.6 | 18.41 | 7.19 | | −5.96 | 62.106 | 62.11 | | |
| | 24.26 | 17.86 | 6.4 | | −6.75 | 107.39 | 107.39 | | |
| Collagen 2A1 DADKP | 27.41 | 17.52 | 9.89 | 7.223 | −3.26 | 9.5577 | 9.56 | 136.83 | 170.14 |
| | 25.44 | 18.44 | 7 | | −6.15 | 70.849 | 70.85 | | |
| | 22.94 | 18.16 | 4.78 | | −8.37 | 330.08 | 330.08 | | |

TABLE 16-continued

Day 22
130529 Gene expression RTPCR

| Sample | Cp | Cp Actin | ΔCp | Mean ΔCp | ΔΔCp vs saline | $2^{-\Delta\Delta Cp}$ vs saline | regulation | Mean regulation | std regulation |
|---|---|---|---|---|---|---|---|---|---|
| Collagen 2A1 Mix | 20.54 | 17.93 | 2.61 | 4.03 | −10.5 | 1485.4 | 1485.43 | 723.78 | 661.47 |
|  | 22.61 | 17.66 | 4.95 |  | −8.2 | 293.39 | 293'39 |  |  |
|  | 21.87 | 17.34 | 4.53 | 4.53 | −8.62 | 392.53 | 392.53 |  |  |
| cells in pellet |  |  |  |  |  |  |  |  |  |
| cells with nodules |  |  |  |  |  |  |  |  |  |
| MMP13 Saline | 21.77 | 18.36 | 3.41 | 2.993 |  |  |  |  |  |
|  | 21.37 | 18.54 | 2.83 |  |  |  |  |  |  |
|  | 20.69 | 17.95 | 2.74 |  |  |  |  |  |  |
| MMP13 Dexamethasone | 20.77 | 16.42 | 4.35 | 4.433 | 1.357 | 0.3905 | −2.56 | −2.73 | 0.4255 |
|  | 20.68 | 16.41 | 4.27 |  | 1.277 | 0.4127 | −2.42 |  |  |
|  | 20.35 | 15.67 | 4.68 |  | 1.687 | 0.3106 | −3.22 |  |  |
| MMP13 Mifepristone | 20.98 | 17.47 | 3.51 | 3.633 | 0.517 | 0.699 | −1.43 | −1.57 | 0.2212 |
|  | 21.32 | 17.46 | 3.86 |  | 0.867 | 0.5484 | −1.82 |  |  |
|  | 21.37 | 17.84 | 3.53 |  | 0.537 | 0.6894 | −1.45 |  |  |
| MMP13 Ampion | 21.18 | 18.45 | 2.73 | 2.96 | −0.26 | 1.2002 | 1.20 | 0.35 | 1.5169 |
|  | 21.82 | 19.15 | 2.67 |  | −0.32 | 1.2512 | 1.25 |  |  |
|  | 22.47 | 18.99 | 3.48 |  | 0.487 | 0.7137 | −1.40 |  |  |
| MMP13 NAT | 22.68 | 19.45 | 3.23 | 3.053 | 0.237 | 0.8487 | −1.18 | 0.29 | 1.2691 |
|  | 21.71 | 18.76 | 2.95 |  | −0.04 | 1.0305 | 1.03 |  |  |
|  | 21.65 | 18.67 | 2.98 |  | −0.01 | 1.0093 | 1.01 |  |  |
| MMP13 Caprylate | 20.28 | 16.85 | 3.43 | 2.733 | 0.437 | 0.7388 | −1.35 | 0.62 | 1.7897 |
|  | 20.31 | 18.41 | 1.9 |  | −1.09 | 2.1337 | 2.13 |  |  |
|  | 20.73 | 17.86 | 2.87 |  | −0.12 | 1.0892 | 1.09 |  |  |
| MMP13 DADKP | 20.34 | 17.52 | 2.82 | 2.96 | −0.17 | 1.1277 | 1.13 | 0.36 | 1.2375 |
|  | 21.41 | 18.44 | 2.97 |  | −0.02 | 1.0163 | 1.02 |  |  |
|  | 21.25 | 18.16 | 3.09 |  | 0.097 | 0.9352 | −1.07 |  |  |
| MMP13 Mix | 20.78 | 17.93 | 2.85 | 3.287 | −0.14 | 1.1045 | 1.10 | −0.58 | 1.463 |
|  | 21.23 | 17.66 | 3.57 |  | 0.577 | 0.6705 | −1.49 |  |  |
|  | 20.78 | 17.34 | 3.44 |  | 0.447 | 0.7337 | −1.36 |  |  |

| Sample | Cp Agg | Cp Actin | ΔCp | Mean ΔCp | ΔΔCp vs saline | $2^{-\Delta\Delta Cp}$ vs saline | regulation | Mean regulation | std regulation |
|---|---|---|---|---|---|---|---|---|---|
| Aggrecan Saline | 27.57 | 16.69 | 10.88 | 10.22 |  |  |  |  |  |
|  | 26.34 | 16.4 | 9.94 |  |  |  |  |  |  |
|  | 25.55 | 15.72 | 9.83 |  |  |  |  |  |  |
| Aggrecan Dexamethasone | 20.48 | 14.2 | 6.28 | 6.523 | −3.94 | 15.313 | 15.31 | 13.03 | 2.0074 |
|  | 20.68 | 13.99 | 6.69 |  | −3.53 | 11.525 | 11.52 |  |  |
|  | 20.44 | 13.84 | 6.6 |  | −3.62 | 12.267 | 12.27 |  |  |
| Aggrecan Mifepristone | 25.97 | 15.68 | 10.29 | 9.247 | 0.073 | 0.9504 | −1.05 | 1.55 | 2.3111 |
|  | 24.4 | 15.42 | 8.98 |  | −1.24 | 2.3565 | 2.36 |  |  |
|  | 23.94 | 15.47 | 8.47 |  | −1.75 | 3.3558 | 3.36 |  |  |
| Aggrecan Ampion | 23.54 | 16.68 | 6.86 | 6.067 | −3.36 | 10.244 | 10.24 | 19.16 | 8.4434 |
|  | 23.28 | 17.4 | 5.88 |  | −4.34 | 20.205 | 20.21 |  |  |
|  | 22.66 | 17.2 | 5.46 |  | −4.76 | 27.033 | 27.03 |  |  |
| Aggrecan NAT | 25.43 | 17.19 | 8.24 | 7.1 | −1.98 | 3.9358 | 3.94 | 11.66 | 10.952 |
|  | 23.3 | 17.68 | 5.62 |  | −4.6 | 24.195 | 24.20 |  |  |
|  | 24.4 | 16.96 | 7.44 |  | −2.78 | 6.8527 | 6.85 |  |  |
| Aggrecan Caprylate | 21.64 | 15.53 | 6.11 | 7.42 | −4.11 | 17.228 | 17.23 | 10.81 | 8.3209 |
|  | 25.43 | 15.71 | 9.72 |  | −0.5 | 1.4109 | 1.41 |  |  |
|  | 21.95 | 15.52 | 6.43 |  | −3.79 | 13.801 | 13.80 |  |  |
| Aggrecan DADKP | 24.7 | 15.64 | 9.06 | 7.28 | −1.16 | 2.2294 | 2.23 | 10.65 | 8.511 |
|  | 23.56 | 16.73 | 6.83 |  | −3.39 | 10.459 | 10.46 |  |  |
|  | 22.36 | 16.41 | 5.95 |  | −4.27 | 19.248 | 19.25 |  |  |
| Aggrecan Mix | 21.47 | 16.62 | 4.85 | 5.023 | −5.37 | 41.26 | 41.26 | 37.33 | 8.649 |
|  | 21.36 | 15.92 | 5.44 |  | −4.78 | 27.411 | 27.41 |  |  |
|  | 20.34 | 15.56 | 4.78 |  | −5.44 | 43.311 | 43.31 |  |  |
| cells in pellet |  |  |  |  |  |  |  |  |  |
| cells with nodules |  |  |  |  |  |  |  |  |  |

| Sample | Cp TIMP1 | Cp Actin | ΔCp | Mean ΔCp | ΔΔCp vs saline | $2^{-\Delta\Delta Cp}$ vs saline | regulation | Mean Regulation | std regulation |
|---|---|---|---|---|---|---|---|---|---|
| TIMP1 Saline | 21.32 | 16.69 | 4.63 | 3.767 |  |  |  |  |  |
|  | 19.91 | 16.4 | 3.51 |  |  |  |  |  |  |
|  | 18.88 | 15.72 | 3.16 |  |  |  |  |  |  |
| TIMP1 Dexamethasone | 17.35 | 14.2 | 3.15 | 3.16 | −0.62 | 1.5333 | 1.53 | 1.53 | 0.2057 |
|  | 17.35 | 13.99 | 3.36 |  | −0.41 | 1.3256 | 1.33 |  |  |
|  | 16.81 | 13.84 | 2.97 |  | −0.8 | 1.7371 | 1.74 |  |  |
| TIMP1 Mifepristone | 19.69 | 15.68 | 4.01 | 4.227 | 0.243 | 0.8448 | −1.18 | −1.38 | 0.1792 |
|  | 19.8 | 15.42 | 4.38 |  | 0.613 | 0.6537 | −1.53 |  |  |
|  | 19.76 | 15.47 | 4.29 |  | 0.523 | 0.6958 | −1.44 |  |  |
| TIMP1 Ampion | 19.44 | 16.68 | 2.76 | 2.993 | −1.01 | 2.0093 | 2.01 | 1.72 | 0.2669 |
|  | 20.42 | 17.4 | 3.02 |  | −0.75 | 1.6779 | 1.68 |  |  |
|  | 20.4 | 17.2 | 3.2 |  | −0.57 | 1.4811 | 1.48 |  |  |

TABLE 16-continued

Day 22
130529 Gene expression RTPCR

| TIMP1 NAT | 20.59 | 17.19 | 3.4 | 3.537 | −0.37 | 1.2894 | 1.29 | 1.18 | 0.0987 |
|---|---|---|---|---|---|---|---|---|---|
| | 21.28 | 17.68 | 3.6 | −0.17 | 1.1225 | 1.12 | | | |
| | 20.57 | 16.96 | 3.61 | −0.16 | 1.1147 | 1.11 | | | |
| TIMP1 Caprylate | 17.65 | 15.53 | 2.12 | 3.143 | −1.65 | 3.1311 | 3.13 | 1.12 | 2.3073 |
| | 18.77 | 15.71 | 3.06 | | −0.71 | 1.632 | 1.63 | | |
| | 19.77 | 15.52 | 4.25 | | 0.483 | 0.7153 | −1.40 | | |
| TIMP1 DADKP | 18.64 | 15.64 | 3 | 3.04 | −0.77 | 1.7013 | 1.70 | 1.66 | 0.13 |
| | 19.9 | 16.73 | 3.17 | | −0.6 | 1.5122 | 1.51 | | |
| | 19.36 | 16.41 | 2.95 | | −0.82 | 1.7613 | 1.76 | | |
| TIMP1 Mix | 19.61 | 16.62 | 2.99 | 3.56 | −0.78 | 1.7132 | 1.71 | 0.53 | 1.5754 |
| | 19.51 | 15.92 | 3.59 | | −0.18 | 1.1303 | 1.13 | | |
| | 19.66 | 15.56 | 4.1 | | 0.333 | 0.7937 | −1.26 | | |

On Day 22, collagen transcription is greatly enhanced by Ampion™. The components are also showing some activity but not nearly as pronounced as Ampion™. Aggrecan is also elevated.

The results of this example show that Ampion has the ability to increase the transcription of Collagen 2A1 and Aggrecan.

Example 7

The following example is a proteomic analysis of synovial fluid from patients treated with Ampion™ compared to the synovial fluid from patients having received saline.

The synovial fluid was taken from knees of patients in a clinical trial for use of Ampion™ to treat osteoarthritis of the knee at baseline and at 12 weeks after treatment with 10 cc of either Ampion™ or saline. Baseline to 12 weeks were compared for both saline and Ampion.

The synovial fluid samples were analyzed by SomaLogic, Inc. of Boulder, Colo., USA using its proprietary SOMAscan™ technology.

The proteins shown below in Table 17 were down in the Ampion™ treated synovial fluid, compared to the saline treated synovial fluid.

TABLE 17

Proteins Down in Ampion ™ Treated Sample

MAPK-activated protein kinase 3
beta-adrenergic receptor kinase 1
ADAM metallopeptidase with thrombodpondin type I motif
MAPK-activated protein kinase 2
C-Src kinase
Macrophage Scavenger Receptor
Noggin
Tyrosine kinase Bruton
Glycogen synthase kinase-3 alpha/beta
Glycogen synthase kinase-3 alpha/beta
HSP 90 alpha/beta
HSP 90 alpha/beta
Phosphoinositide-3-kinase, catalytic subunit alpha
Phosphoinositide-3-kinase, catalytic subunit alpha
Eukaryotic translation initiation factor 4A
Fibroblast Growth Factor 17

The proteins shown below in Table 18 were up in the Ampion™ treated synovial fluid, compared to the saline treated synovial fluid.

TABLE 18

Proteins Up in Ampion ™ Treated Sample

Clusterin (Apolipoprotein J)
C1QBP (Hyaluronan binding protein 1)
Mammaglobin 2
MCP 1 (CCL 2)
Spondin 1
IL 11
CFC 1 (cryptic protein)
Angiogenin
MMP-3
BSSP 4
RSPO2
bFGF
Coagulation Factor IX
CATC (Dipeptidyl peptidase 1)
Ck-b-8-1 (MPIF 1 splice variant)
C1s
EMR2
ART
DPP 2
SAA
TIMP-1
Semaphorin 3A
Prothrombin
TNFSF 15 (VEGF inhibitor)
MIP3b (CCL 19)
PTHrP
Elafin (elastase inhibitor)
NPS-PLA2
Testican 1 (SPOCK 1)
URB
IP10 (cxcl 10)
IL 8 (cxcl 8)
Cystatin C
Factor H
SDF-1 (cxcl 12)
PIGR The proteins shown below in Table 19 were significantly different (up or down) in the Ampion™ treated synovial fluid, compared to the saline treated synovial fluid and are known to influence cartilage and synovial fluid production.

TABLE 19

Proteins Up in Ampion ™ Treated Sample

| Protein Name | Direction Compared to Saline | Protein Description |
|---|---|---|
| Clusterin | up | Known to stimulate proliferation and stability of different stem cells |
| C1QBP | up | A hyaluronic binding protein and inhibits C1, thus inhibiting complement induced apoptosis |

TABLE 19-continued

Proteins Up in Ampion ™ Treated Sample

| Protein Name | Direction Compared to Saline | Protein Description |
|---|---|---|
| MAPKAPK3 | down | Modulates polycomb mediated repression of gene expression (through Akt pathway), which is necessary for hematopoietic stem cell maintenance |
| MCP-1 | up | Recruits macrophages in inflammatory conditions |
| IL-11 | up | Stimulates production of hematopoietic stem cells and megakaryote precursor cells |
| MMP3 | up | A metalloproteinase which also breaks down proteoglycans |
| bFGF | up | Stimulates mesenchymal cell growth |
| Noggin | down | Essential for cartilage formation in embryos, inhibitor of bone morphogenetic proteins |
| PIK3CA | down | regulates Akt |
| SAA | up | Plays an important role in HDL metabolism, and is up regulated in many inflammatory diseases |
| TIMP 1 | up | A major inhibitor if MMPs and tissue extracellular matrix |
| PTHrP | up | Regulates epithelial-mesenchymal interactions |
| Elafin | up | Inhibits elastin (protease) |

The results of this example suggest that administration of Ampion™ down regulates Akt pathways. Akt, also known as Protein Kinase B (PKB) is a serine/threonine-specific protein kinase that plays a key role in multiple cellular processes such as cell proliferation, transcription and cell migration.

Example 8

This example demonstrates the effect of intra-articular injections of a low molecular weight fraction of 5% human serum albumin (LMWF-5A) for treatment of knee pain due to osteoarthritis.

This study was a multicenter randomized, vehicle-controlled, double-blind, parallel study designed to evaluate the safety and efficacy of two doses of an intra-articular injection of LMWF-5A. Patients with symptomatic knee osteoarthritis were randomized 1:1:1:1 to receive a single 4 mL or 10 mL intra-articular knee injection of either LMWF-5A or vehicle control (saline). The primary efficacy endpoint was the difference between treatment groups in the Western Ontario and McMaster Universities (WOMAC) pain change from baseline over 12 weeks. Safety was examined as the incidence and severity of adverse events (AEs).

Figure 10:
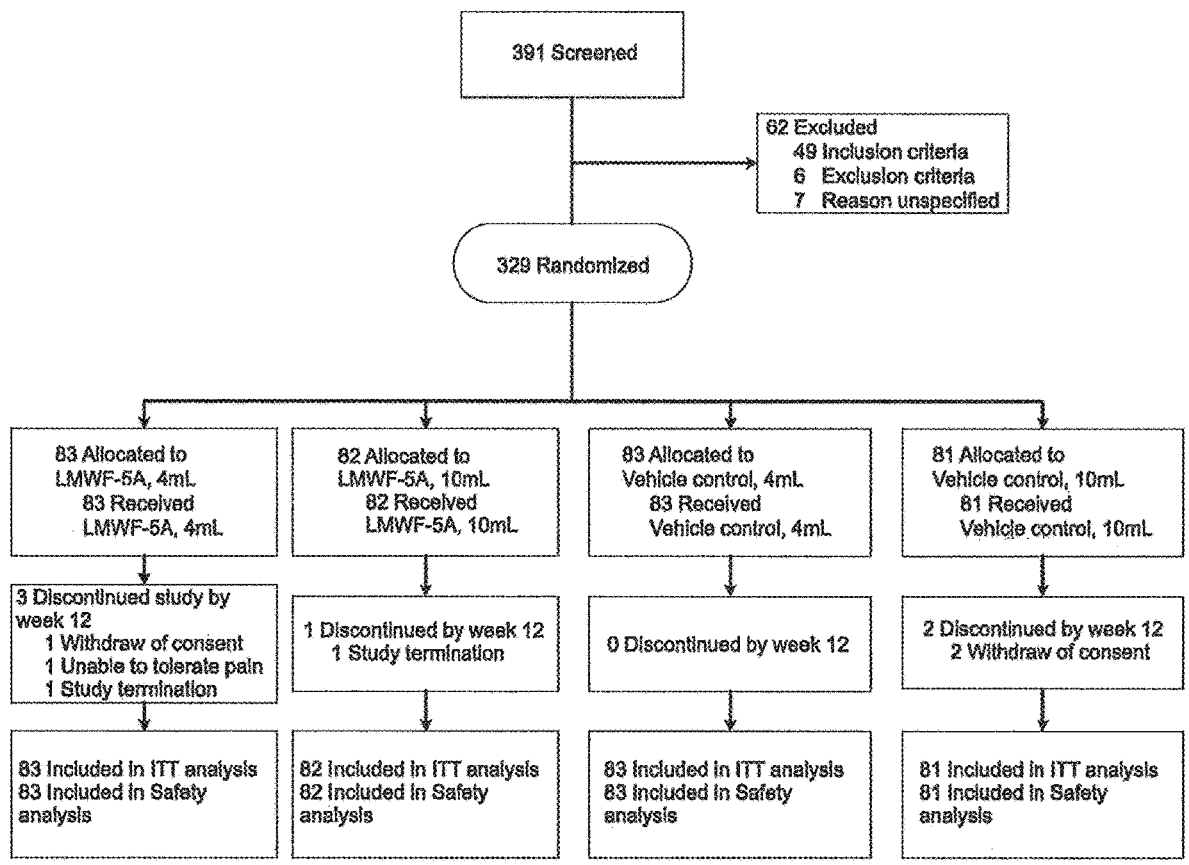
FIG. 10 illustrates the patient disposition of the clinical trial described in Example 8.

A total of 329 patients with OA knee pain were randomized 1:1:1:1 across 4 study arms: 4 mL LMWF-5A, 4 mL saline vehicle control, 10 mL LMWF-5A or 10 mL saline vehicle control. The patient disposition is shown in FIG. 10.

The starting material of LMWF-5A, HSA purchased from OctaPharma (Lachen, Switzerland), was subjected to centrifugation/ultrafiltration under sterile conditions and the ultrafiltrate, containing species with a MW less than 5000 Da, was separated. The ultrafiltrate contained DA-DKP (approximately 50-200 mM) and the excipients (i.e. sodium caprylate and sodiumacetyltryptophanate). The ultrafiltrate was transferred for aseptic filling, to afford sterile drug product.

The clinical effects of treatment on OA were evaluated during clinic visits at 6 and 12 weeks and telephone contacts at 2, 4, 8 and 10 weeks, using the WOMACH osteoarthritis Index 3.1 5-point Likert score, the Patient's Global Assessment of disease severity (PGA) using a 5-point Likert Score, and the amount of acetaminophen after intra-articular injection. Acetaminophen was supplied in 500 mg tablets at baseline as a rescue medication, and allowed as 1 tablet every 4 hours as needed. Safety was evaluated by recording adverse events (through 24 hours post-dose and at all follow-up contacts), vital signs and physical examination results (baseline, weeks 6 and 12).

Figure 11:
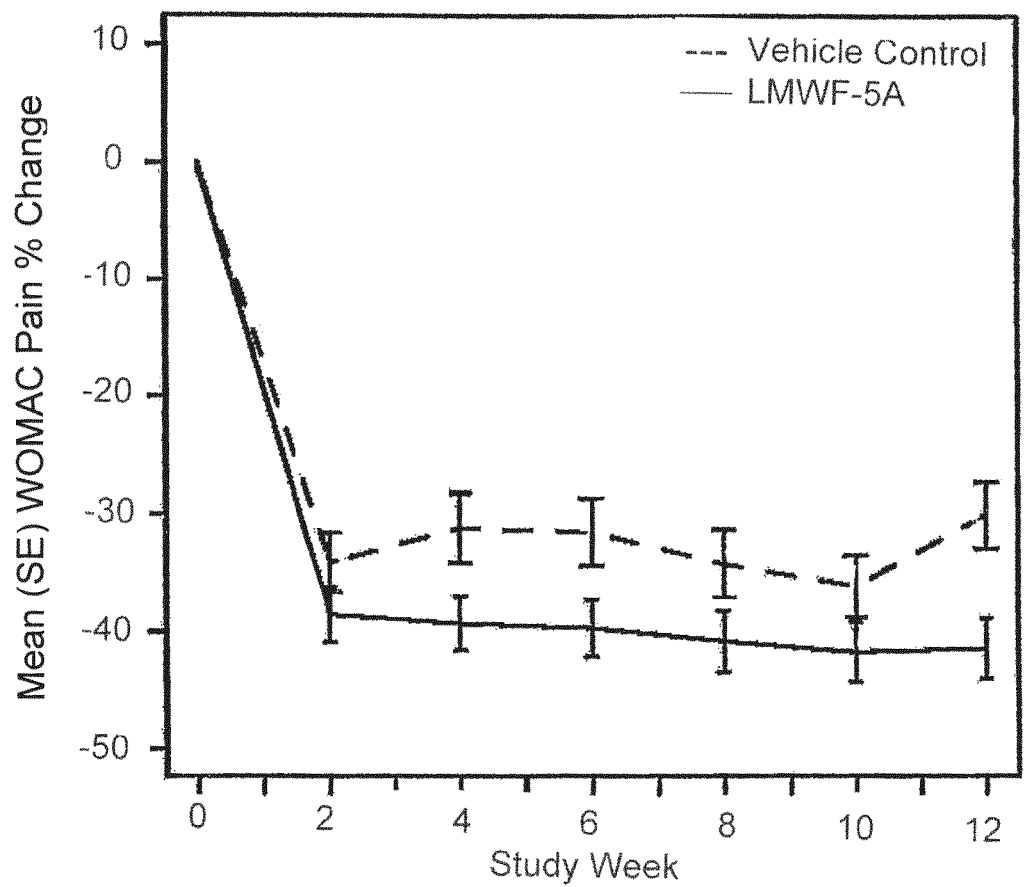
FIG. 11 illustrates the reduction in pain for osteoarthritis patients receiving injections of LMWF-5A as compared to vehicle control.

LMWF-5A resulted in a statistically significant improvement in pain as compared to vehicle control (20.93 vs 20.72, respectively). An injection volume effect was not observed (p=0.64). The estimated difference from control was 20.25 (95% CI: 20.08-20.41), p=0.004. The reduction in pain with LMWF-5A compared to vehicle control was observed as early as week 4 (p=0.03), and persisted to week 12 (p=0.004). The percent reduction in pain over time was significantly greater for LMWF-5A as compared to vehicle control (week 12: 42.3% and 31.7%, respectively) as shown in FIG. 11.

Patients treated with LMWF-5A demonstrated significant improvements in the following secondary endpoints, as compared to vehicle control: PGA (20.87 vs 20.65, p=0.01), physical function, (20.78 vs 20.64, p=0.04); pain at rest (20.91 vs 20.70, p=0.004); pain with movement (20.96 vs 20.75, p=0.01), Table 3. There were no differences in reduced stiffness between treatment groups. There was a trend towards a reduced number of acetaminophen pills used over the study period for LMWF-5A as compared to vehicle control (median (IQR)): 24.0 (0, 62) vs 34.0 (5, 85.5), p=0.09. Improvement in pain in this study is consistent with regeneration of tissue caused by the administration of Ampion™.

Example 9

This example is a twenty week extension of the clinical trial described in Example 8 demonstrating the effects of LMWF-5A for treatment of knee pain due to osteoarthritis.

This analysis is a 20-week extension of a multicenter, randomized, vehicle-controlled, double-blind study (NCT01839331) that evaluated the efficacy and safety of the low molecular weight fraction of 5% human serum albumin (LMWF-5A) for treatment of inflammation-associated pain in symptomatic OA of the knee (OAK).

Ninety-seven patients who received a 4-mL intra-articular injection of LMWF-5A or vehicle control were followed for an additional 8 weeks beyond the initial 12-week study endpoint. Efficacy measures included changes from baseline in Western Ontario and McMaster Universities Osteoarthritis (WOMAC) pain and function subscores. Patients were considered "responders" if they achieved ≥40% improvement in WOMAC pain and function. Differences between treatment groups were evaluated by chi-square test or ANCOVA, adjusted for baseline values.

In a subgroup of patients with moderate-to-severe OAK (Kellgren-Lawrence grades 3-4; n=64), there were statistically significant improvements in WOMAC pain (mean change from baseline −0.99 vs −0.65) and function scores (−0.85 vs −0.58) over 20 weeks for patients who received LMWF-5A compared with vehicle control, respectively. Treatment-versus-placebo-associated differences in pain (−0.95 vs −0.77) and function (−0.79 vs −0.63), respectively, were also observed in the per-protocol population. At 20 weeks, the percentage of pain responders in the moderate-to-severe subgroup was significantly higher for patients who received LMWF-5A (50%) relative to those who received vehicle control (25%). Similar rates and severity of adverse events were observed in the LMWF-5A and control groups.

This example demonstrates that a single injection of LMWF-5A was associated with sustained improvements in knee pain and can provide a therapeutic option for patients with moderate-to-severe OAK. These findings demonstrate significant benefit of LMWF-5A for patients with objective evidence of true OAK and high therapeutic need.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A composition, comprising:
   a low molecular weight fraction of a human serum albumin pharmaceutical composition comprising aspartyl-alanyl diketopiperazine (DA-DKP), N-acetyl tryptophan, and caprylate and/or caprylic acid, wherein:
   albumin has been removed by filtration;
   the molecular weight of the fraction is less than 5000;
   the fraction comprises DA-DKP; and
   a cell culture medium supplemented with said supplement is capable of supporting the expansion of stem cells.

2. The composition of claim 1, further comprising stem cells in a serum-free media.

3. The composition of claim 1, wherein the low molecular weight fraction of the human serum albumin pharmaceutical composition is prepared by heating human serum albumin under conditions effective to cause the formation of DA-DKP.

4. The composition of claim 1, wherein the low molecular weight fraction of the human serum albumin pharmaceutical composition is prepared by contacting human serum albumin with an enzyme that cleaves the two N-terminal amino acids of human albumin under conditions effective to produce DA-DKP.

5. The composition of claim 1, wherein the DA-DKP is synthetic.

6. The composition of claim 2, wherein the stem cells are selected from the group consisting of progenitor cells and mesenchymal stem cells.

* * * * *